US009084813B2

(12) United States Patent
Roberson et al.

(10) Patent No.: US 9,084,813 B2
(45) Date of Patent: Jul. 21, 2015

(54) AGENTS THAT REDUCE NEURONAL OVEREXCITATION

(71) Applicant: The J. David Gladstone Institutes, San Francisco, CA (US)

(72) Inventors: Erik D. Roberson, Vestavia Hills, AL (US); Lennart Mucke, San Francisco, CA (US)

(73) Assignee: THE J. DAVID GLADSTONE INSTITUTES, San Francisco, CA (US)

(*) Notice: Subject to any disclaimer, the term of this patent is extended or adjusted under 35 U.S.C. 154(b) by 0 days.

(21) Appl. No.: 14/029,604

(22) Filed: Sep. 17, 2013

(65) Prior Publication Data

US 2014/0065206 A1    Mar. 6, 2014

Related U.S. Application Data

(62) Division of application No. 13/082,170, filed on Apr. 7, 2011, which is a division of application No. 12/098,328, filed on Apr. 4, 2008, now abandoned.

(60) Provisional application No. 60/922,082, filed on Apr. 5, 2007.

(51) Int. Cl.
| A61K 48/00 | (2006.01) |
| G01N 33/50 | (2006.01) |
| C12N 15/113 | (2010.01) |
| G01N 33/68 | (2006.01) |

(52) U.S. Cl.
CPC ............ *A61K 48/005* (2013.01); *C12N 15/113* (2013.01); *G01N 33/5023* (2013.01); *G01N 33/5058* (2013.01); *G01N 33/5088* (2013.01); *G01N 33/6896* (2013.01); *C12N 2310/11* (2013.01); *C12N 2310/14* (2013.01); *G01N 2800/28* (2013.01); *G01N 2800/2821* (2013.01)

(58) Field of Classification Search
None
See application file for complete search history.

(56) References Cited

U.S. PATENT DOCUMENTS

| 5,492,812 | A | 2/1996 | Vooheis | |
| 5,994,084 | A | 11/1999 | Anderton et al. | |
| 6,027,721 | A | 2/2000 | Hammang et al. | |
| 6,420,122 | B1 | 7/2002 | Housman et al. | |
| 6,787,318 | B1 | 9/2004 | Tan et al. | |
| 2002/0018995 | A1* | 2/2002 | Ghetti et al. | 435/6 |
| 2003/0050221 | A1 | 3/2003 | Hock et al. | |
| 2003/0115621 | A1 | 6/2003 | Duff | |
| 2004/0077663 | A1 | 4/2004 | Benish et al. | |
| 2004/0110938 | A1* | 6/2004 | Parekh et al. | 536/23.5 |
| 2004/0241854 | A1 | 12/2004 | Davidson et al. | |
| 2005/0022256 | A1 | 1/2005 | Laferla | |
| 2005/0266420 | A1* | 12/2005 | Pusztai et al. | 435/6 |
| 2006/0063732 | A1* | 3/2006 | Vogel et al. | 514/44 |
| 2006/0154370 | A1 | 7/2006 | Chen et al. | |
| 2007/0271619 | A1* | 11/2007 | Von Der Kammer et al. | 800/3 |
| 2008/0003570 | A1* | 1/2008 | Rogers et al. | 435/6 |

FOREIGN PATENT DOCUMENTS

| EP | 1491889 A2 | 12/2004 |
| WO | WO 00/14546 | 3/2000 |
| WO | WO 2007/008586 | 1/2007 |

OTHER PUBLICATIONS

Andreadis 2005 "Tau gene alternative splicing: expression patterns, regulation and modulation of function in normal brain and neurodegenerative diseases" biochimica et biophysica acta 1739:91-103.*
aronov et al. 1999 "Identification of 3'utr region implicated in tau mRNA stabilization in neuronal cells" J Mol Neurosci 12:131-145.*
Chabot et al. 1997 "An intron element modulating 5' splice site selection in the hnRNP A1 Pre-mRNA Interacts with hnRNP A1" Mol Cell Bio 17(4):1776-1786.*
Del Gatto et al. 1996 "The exon sequence TAGG can inhibit splicing" Nucleic acids Res 24(11):2017-21 (abstract only).*
Gao et al. 2000 "Complex regulation of tau exon 10, whose missplicing causes frontotemporal dementia" J Neurochem 74:490-500.*
Hebert et al. 2012 "MicroRNAs and the regulation of tau metabolism" IJAD 2012:1-6.*
Qiagen "RNAiFect Transfection Reagent" product description accessed Aug. 20, 2014 from www.qiagen.com.*
Santacruz et al. 2005 "Tau suppression in a neurodegenerative mouse model improves memory function" Science 309:476-481 plus supplementary data.*
Acharya, et al., "Progress in Neuroprotective Strategies for Preventing Epilepsy", Prog Neurobiol, 2008, 84(4), 363-404.
Alonso et al., "Interaction of tau isoforms with Alzheimer's disease abnormally hyperphosphorylated tau and in vitro phosphorylation into the disease-like protein", J Biol Chem., Oct. 12, 2001 276(41), 37967-73.
Auld and Robitaille, "Glial Cells and Neurotransmission: an Inclusive View of Synaptic Function", Neuron, 2003, 40, 389-400.
Brandt, et al., "Tau Alteration and Neuronal Degeneration in Tauopathies: Mechanisms and Models", Biochimica et Biophysica Acta, 2005, 1739, 331-354.
Centeno et al. "Role of the JNK Pathway in NMDA-Mediated Excitotoxicity of Cortical Neurons", Cell Death and Differentiation, 2007, 14(2), 240-53.

(Continued)

*Primary Examiner* — Jeffrey Stucker
*Assistant Examiner* — Adam M Weidner
(74) *Attorney, Agent, or Firm* — Bozicevic, Field & Francis LLP; Paula A. Borden

(57) ABSTRACT

Agents that reduce the level of a tau gene product in a cell, e.g., in a neuron, include antisense nucleic acids. For example, antisense nucleic acids can be used to down-regulate expression of a tau gene in a cell (e.g., in a neuron). The antisense sequence is complementary to the mRNA of the targeted gene (e.g., tau), and inhibits expression of the targeted gene products. Suitable oligonucleotides can be chemically modified from the native phosphodiester structure, in order to increase their intracellular stability and binding affinity. A number of such modifications have been described in the literature, which modifications alter the chemistry of the backbone, sugars, or heterocyclic bases.

16 Claims, 28 Drawing Sheets

(56) References Cited

OTHER PUBLICATIONS

Chen, et al., "Advances in the Pathophysiology of Status Epilepticus", Acta. Neurol. Scand., 2007, 115, Suppl. 186, 7-15.
Churcher, I., "Tau Therapeutic Strategies for the Treatment of Alzheimer's Disease", Current Topics in Medicinal Chemistry, 2006, 6, 579-595.
Costello, et al., "Treatment of Acute Seizures and Status Epilepticus", Journal of Intensive Care Medicine, 2007, 22(6), 319-347.
Couchie et al. "Primary structure of high molecular weight tau present in the peripheral nervous system." Proc. Natl. Acad. Sci. USA, May 15, 1992 89(10), 4378-4381.
Couratier P et al: "NMDA antagonist blockade of AT8 tau immunoreactive changes in neuronal cultures", Fundamental and Clinical Pharmacology, vol. 10, No. 4, 1996, pp. 344-349, ISSN: 0767-3981.
Cross et al. "Synaptic Reorganization in Subiculum and CA3 After Early-Life Status Epilepticus in the Kainic Acid Rat Model", Epilepsy Res., 2007, 73(2), 156-65.
Dehmelt, et al., "The MAP2/Tau Family of Microtubule-Associated Proteins", Genome Biology, 2006, 6(1), 204-204.
Dickey, Current Alzheimer Res., 2005, 2, 231-238.
Dickey et al., "Pharmacologic reductions of total tau levels; implications for the role of microtubule dynamics in regulating tau expression", Mol. Neurodegener., 2006, 1(6), Published online Jul. 26, 2006 doi: 10.1186/1750-1326-1-6.
Feinstein, et al., "Inability of Tau to Properly Regulate Neuronal Microtubule Dynamics: a loss-of-function mechanism by which tau might mediate neuronal cell death", Biochimica et Biophysica Acta, 2005, 1739, 268-279.
Gluck et al., "CNS Oxidative Stress Associated with the Kainic Acid Rodent Model of Experimental Epilepsy", Epilepsy Research, 2000, 39, 63-71.
Goedert, et al., "Tau Protein, the Paired Helical Filament and Alzheimer's Disease", Journal of Alzheimer's Disease, 2006, 9, 195-207.
Himmelstein, et al., "Tau as a Therapeutic Target in Neurodegenerative Disease", Pharmacol Ther., 2012, 136(1), 32 pages.
Jakes et al. Identification of 3- and 4-repeat tau isoforms within the PHF in Alzheimer's disease. EMBO J. Oct. 1991;10(10):2725-9.
Kwan, et al., "Emerging Drugs for Epilepsy", Expert Opin. Emerging Drugs, 2007, 12(3), 407-422.
Leschik et al., "Inverse and Distinct Modulation of Tau-Dependent Neurodegeneration by Presenilin 1 and Amyloid-Beta in Cultured Cortical Neurons: Evidence that Tau Phosphorylation is the Limiting Factor in Amyloid-Beta-Induced Cell Death", Journal of Neutochemistry, 2007, 101(5), 1303-15.
MacKay et al., "Evaluation of the Mouse tgtp6.3 taugfp Transgene as a Lineage Marker in Chimeras", J. Anat., 2005, 206, 79-92.
Maddalena et al., "Biochemical diagnosis of Alzheimer disease by measuring the cerebrospinal fluid ratio of phosphorylated tau protein to beta-amyloid peptide42", Arch Neurol, Sep. 2003, 60(9), 1202-1206.
Mark, Robert J et al: "Anticonvulsants attenuate amyloid beta-peptide neurotoxicity, Ca-2+ deregulation, and cytoskeletal pathology", Neurobiology of Aging, vol. 16, No. 2, 1995, pp. 187-198, ISSN: 0197-4580.
McNamara, et al., "Molecular Signaling Mechanisms Underlying Epileptogenesis", Oct. 10, 2006, Science's STKE, 22 pages.
Miller et al., "Glial Cell Inclusions and the Pathogenesis of Neurodegenerative Diseases", Neuron Glia Biol., 2004, 1, 13-21.

Perucca, et al., "Development of New Antiepileptic Drugs: Challenges, Incentives, and Recent Advantages", 2007, Lancet Neurol., 6, 793-804.
Pizzi, et al., "Antisense strategy unravels tau proteins as molecular risk factors for glutamate-induced neurodegeneration", Cellular and Molecular Neurobiology, Oct. 1994, 14(5), 569-578.
Pizzi, et al., "A Tau antisense oligonucleotide decreases neurone sensitivity to excitotoxic injury", Neuroreport (Jun. 1993), 4(6), 823-826.
Pizzi Marina et al: "Inhibition of Glutamate-induced Neurotoxicity by a Tau Antisense Oligonucleotide in Primary Culture of Rat Cerebellar Granule Cells", European Journal of Neuroscience, vol. 7, No. 7, 1995, pp. 1603-1613, ISSN: 0953-816X.
Rapoport et al., "Tau is essential to beta-amyloid-induced neurotoxicity", Proc. Natl. Acad. Sci. USA, Apr. 30, 2002 99(9), 6364-9.
Roberson, et al., "Amyloid-Beta/Fyn-Induced Synaptic, Network, and Cognitive Impairments Depend on Tau Levels in Multiple Mouse Models of Alzheimer's Disease", J Neurosci, 2011, 31(2), 28 pages.
Robert, et al., "Tau and Tauopathies", Neurol. India, 2007, 55(1), 12 pages.
Robertson et al., "Reducing Tau Prevents a Beta-Induced Cognitive Impairment in a Mouse Model of Alzheimer Disease", Neurology, 2006, 66(2), suppl.2, 280.
Robertson et al., "Reducing Tau Prevents a Beta-Induced Premature Mortality and Cognitive Deficits Despite Amyloid Plaques and Neuritic Dystrophy", Annals of Neurology, 2006, 60, suppl. 10, S6-S7.
Roder, et al., "Microtubule-Associated Protein Tau as a Therapautic Target in Neurodegenerative Disease", Expert Opin. Ther. Targets, 2007, 11(4), 435-442.
Scharfman, et al., "The Neurobiology of Epilepsy", Curr. Neurol. Neurosci. Rep., 2007, 7(4), 348-354.
Stefan, et al., "Emerging Drugs for Epilepsy and Other Treatment Options", European Journal of Neurology, 2007, 14, 1154-1161.
Uberti, Daniela et al, "Priming of cultured neurons with sabeluzole results in long-lasting inhibition of neurotoxin-induced tau expression and cell death", Synapse (New York), vol. 26, No. 2, 1997, pp. 95-103, ISSN: 0887-4476.
Van Gool et al., "Disease- and treatment-related elevation of the neurodegenerative marker tau in children with hematological malignancies", Leukemia, Dec. 2000, 14(12), 2076-84.
Kenski; et al., "siRNA-optimized Modifications for Enhanced In Vivo Activity.", Mol Ther Nucleic Acids (Jan. 2012), 1: e5.
Miller; et al., "Targeting Alzheimer's disease genes with RNA interference: an efficient strategy for silencing mutant alleles.", Nucleic Acids Res. (Jan. 2004), 32(2):661-8.
Faught et al. "Epidemiology and drug treatment of epilepsy in elderly people" Drugs Aging, 1999, vol. 15, No. 4, pp. 255-269.
Mendez and Lim "Seizures in elderly patients with dementia: epidemiology and management" Drugs Aging, 2003, vol. 20, No. 11, pp. 791-803.
Rickey et al. "Epilepsy Drugs useful to treat Alzheimer's, studies find" Published by the University of Rochester at www.rochester.edu, 1998.
Sanna et al. "A role for Src kinase in spontaneous epileptiform activity in the CA3 region of the hippocampus" PNAS, 2000, vol. 97, No. 15, pp. 8653-8657.
Santacruz et al. "Tau suppression in a neurodegeneration mouse model improves memory function" Science, 2005, vol. 309, p. 476.
Small "Neural network dysfunction in Alzheimer's disease: a drug development perspective" Drug News Perspect, 2007, vol. 20, No. 9, pp. 557-563 (abstract only).

* cited by examiner

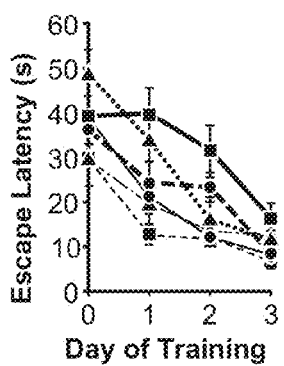
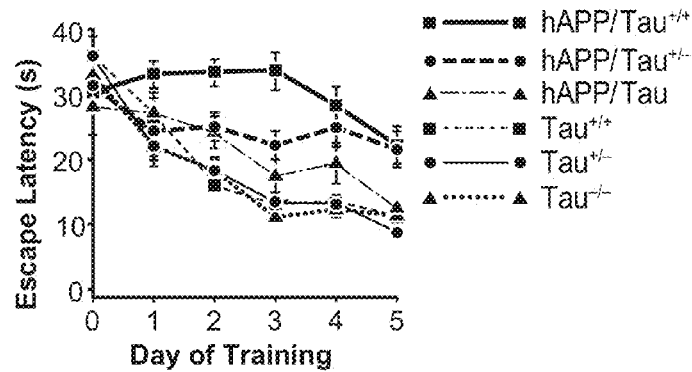
FIG. 1A  FIG. 1B
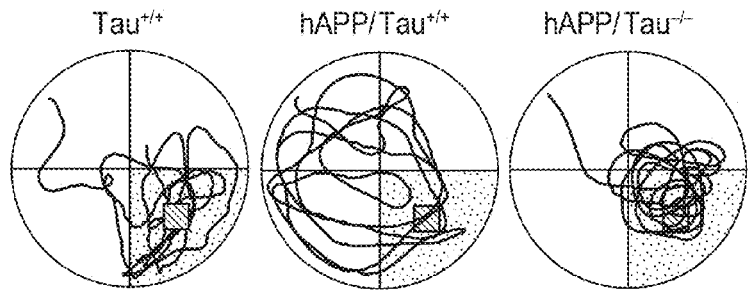
FIG. 1C
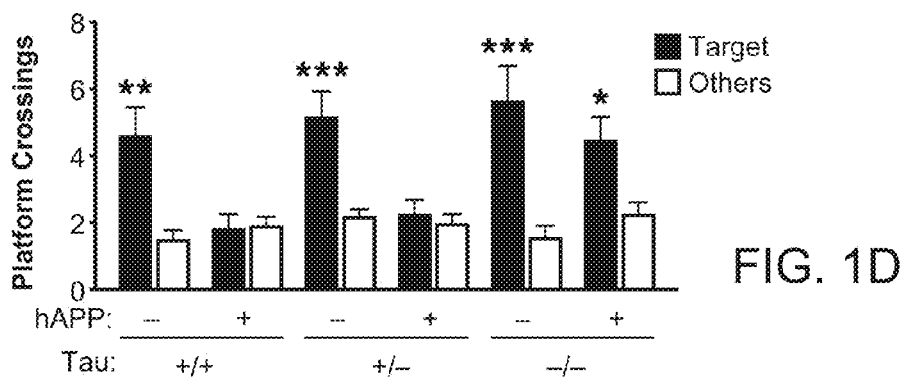
FIG. 1D
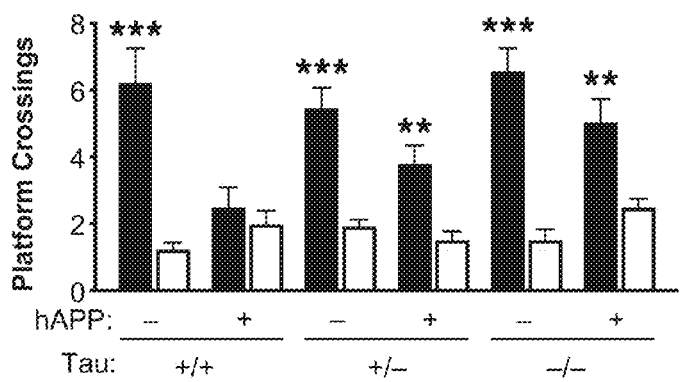
FIG. 1E

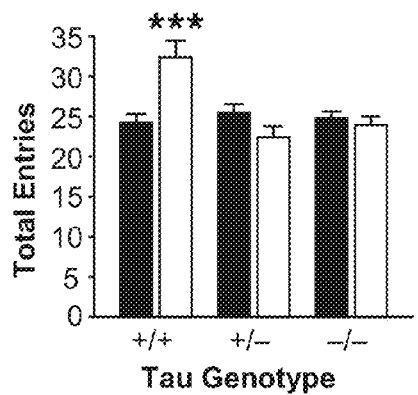 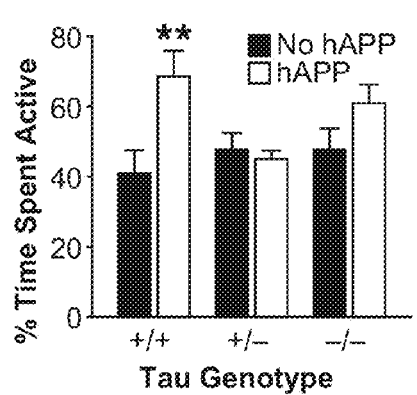
FIG. 2A  FIG. 2B
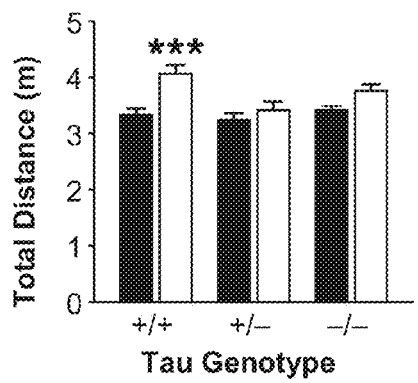 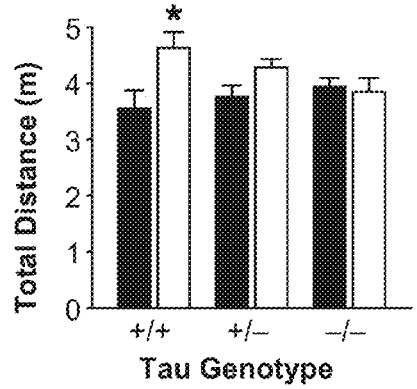
FIG. 2C  FIG. 2D
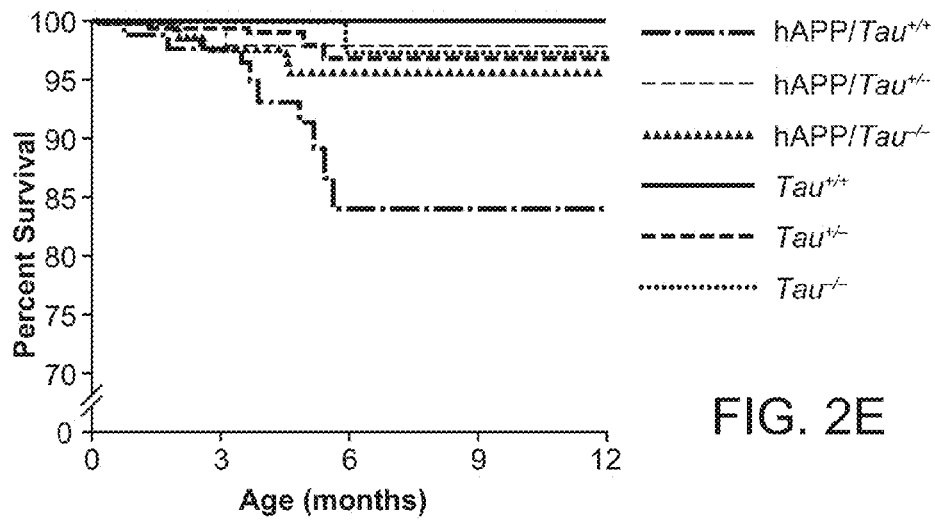
FIG. 2E

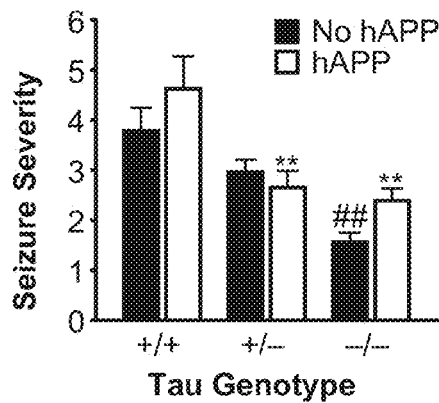 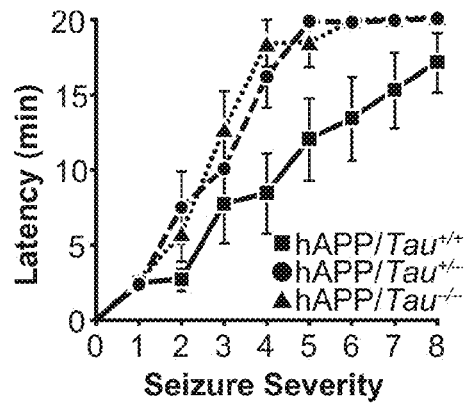
FIG. 4A  FIG. 4B
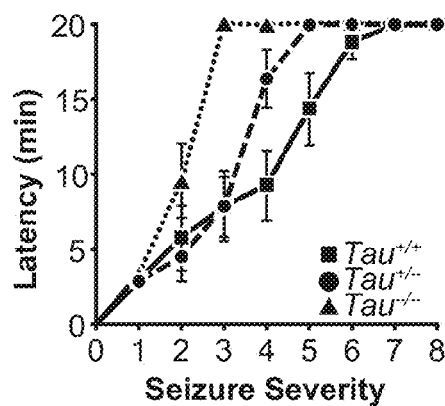 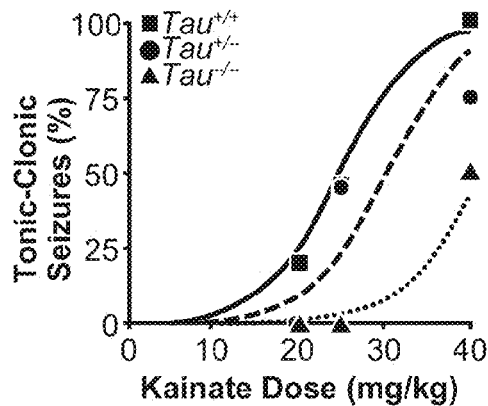
FIG. 4C  FIG. 4D

```
  1 maeprqefev medhagtygl gdrkdqggyt mhqdqegdtd aglkesplqt ptedgseepg
 61 setsdakstp taedvtaplv degapgkqaa aqphteipeg ttaeeagigd tpsledeaag
121 hvtqepesgk vvqegflrep gppglshqlm sgmpgapllp egpreatrqp sgtgpedteg
181 grhapellkh qllgdlhqeg pplkgaggke rpgskeevde drdvdesspq dsppskaspa
241 qdgrppqtaa reatsipgfp aegaiplpvd flskvsteip asepdgpsvg rakgqdaple
301 ftfhveitpn vqkeqahsee hlgraafpga pgegpeargp slgedtkead lpepsekqpa
361 aaprgkpvsr vpqlkarmvs kskdgtgsdd kkaktstrss aktlknrpcl spklptpgss
421 dpliqpsspa vcpeppsspk hvssvtsrtg ssgakemklk gadgktkiat prgaappgqk
481 gqanatripa ktppapktpp ssgeppksgd rsgysspgsp gtpgsrsrtp slptpptrep
541 kkvavvrtpp kspssaksrl qtapvpmpdl knvkskigst enlkhqpggg kvqiinkkld
601 lsnvqskcgs kdnikhvpgg gsvqivykpv dlskvtskcg slgnihhkpg ggqvevksek
661 ldfkdrvqsk igsldnithv pgggnkkiet hkltfrenak aktdhgaeiv ykspvvsgdt
721 sprhlsnvss tgsidmvdsp qlatladevs aslakqgl (SEQ ID NO:1)
```

FIG. 6A

```
   1 atggctgagc cccgccagga gttcgaagtg atggaagatc acgctgggac gtacgggttg
  61 ggggacagga aagatcaggg gggctacacc atgcaccaag accaagaggg tgacacggac
 121 gctggcctga agaatctcc cctgcagacc cccactgagg acggatctga ggaaccgggc
 181 tctgaaacct ctgatgctaa gagcactcca acagcggaag atgtgacagc acccttagtg
 241 gatgagggag ctcccggcaa gcaggctgcc gcgcagcccc acacggagat cccagaagga
 301 accacagctg aagaagcagg cattggagac accccagcc tggaagacga agctgctggt
 361 cacgtgaccc aagagcctga aagtggtaag gtggtccagg aaggcttcct ccgagagcca
 421 ggcccccag gtctgagcca ccagctcatg tccggcatgc ctgggctcc ctcctgcct
 481 gagggcccca gagaggccac acgccaacct tcgggacag gacctgagga cacagagggc
 541 ggccgccacg cccctgagct gctcaagcac cagcttctag gagacctgca ccaggagggg
 601 ccgccgctga aggggcaggg gggcaaagag aggccgggga gcaaggagga ggtggatgaa
 661 gaccgcgacg tcgatgagtc ctccccccaa gactcccctc cctccaaggc ctccccagcc
 721 caagatgggc ggcctcccca gacagccgcc agagaagcca ccagcatccc aggcttccca
 781 gcggagggtg ccatccccct ccctgtggat ttcctctcca agtttccac agagatccca
 841 gcctcagagc ccgacgggcc cagtgtaggg cgggccaaag gcaggatgc cccctggag
 901 ttcacgtttc acgtggaaat cacacccaac gtgcagaagg agcaggcgca ctcggaggag
 961 catttgggaa gggctgcatt tccaggggcc cctggagagg ggccagaggc ccggggcccc
1021 tctttgggag aggacacaaa agaggctgac cttccagagc cctctgaaaa gcagcctgct
1081 gctgctccgc ggggaagcc cgtcagccgg gtccctcaac tcaaagctcg catggtcagt
1141 aaaagcaaag acgggactgg aagcgatgac aaaaaagcca agacatccac acgttcctct
1201 gctaaaacct tgaaaaatag gccttgcctt agcccaaac tccccactcc tggtagctca
1261 gaccctctga tccaaccctc cagccctgct gtgtgccag gccaccttc ctctcctaaa
1321 cacgtctctt ctgtcacttc ccgaactggc agttctggag caaaggagat gaaactcaag
1381 ggggctgatg gtaaaacgaa gatcgccaca ccgcggggag cagcccctcc aggccagaag
1441 ggccaggcca acgccaccag gattccagca aaaacccgc ccgctccaaa gacaccaccc
1501 agctctggtg aacctccaaa atcaggggat cgcagcggct acagcagccc cggctcccca
1561 ggcactccg gcagccgctc ccgcaccacc tcccttccaa ccccacccac ccggagccc
1621 aagaaggtgg cagtgctccg tactccacc aagtcgccgt cttccgccaa ggccgcctg
1681 cagacagccc ccgtgcccat gccagacctg aagaatgtca agtccaagat cggctccact
1741 gagaacctga agcaccagcc gggaggcggg aagtgcaga taattaataa gaagctggat
1801 cttagcaacg tccagtccaa gtgtggctca aaggataata tcaaacacgt cccgggaggc
1861 ggcagtgtgc aaatagtcta caaaccagtt gacctgagca aggtgacctc caagtgtggc
1921 tcattaggca acatccatca taaccagga ggtggccagg tggaagtaaa atctgagaag
1981 cttgacttca aggacagagt ccagtcgaag attgggtccc tggacaatat caccacgtc
2041 cctggcggag gaaataaaaa gattgaaacc cacaagctga ccttccgcga gaacgccaaa
2101 gccaagacag accacggggc ggagatcgtg tacaagtcgc cagtggtgtc tgggacacg
2161 tctccacggc atctcagcaa tgtctcctcc accggcagca tcgacatggt agactcgccc
2221 cagctcgcca cgctagctga cgaggtgtct gcctcctgg ccaagcaggg tttgtga
```
(SEQ ID NO:2)

FIG. 6B

```
  1 maeprqefev medhagtygl gdrkdqggyt mhqdqegdtd aglkesplqt ptedgseepg
 61 setsdakstp taedvtaplv degapgkqaa aqphteipeg ttaeeagigd tpsledeaag
121 hvtqarmvsk skdgtgsddk kakgadgktk iatprgaapp gqkgqanatr ipaktppapk
181 tppssgeppk sgdrsgyssp gspgtpgsrs rtpslptppt repkkvavvr tppkspssak
241 srlqtapvpm pdlknvkski gstenlkhqp gggkvqiink kldlsnvqsk cgskdnikhv
301 pgggsvqivy kpvdlskvts kcgslgnihh kpgggqvevk sekldfkdrv qskigsldni
361 thvpgggnkk iethkltfre nakaktdhga eivykspvvs gdtsprhlsn vsstgsidmv
421 dspqlatlad evsaslakqg l (SEQ ID NO:3)
```

FIG. 6C

```
   1 atggctgagc cccgccagga gttcgaagtg atggaagatc acgctgggac gtacgggttg
  61 ggggacagga aagatcaggg gggctacacc atgcaccaag accaagaggg tgacacggac
 121 gctggcctga aagaatctcc cctgcagacc cccactgagg acggatctga ggaaccgggc
 181 tctgaaacct ctgatgctaa gagcactcca acagcggaag atgtgacagc acccttagtg
 241 gatgagggag ctcccggcaa gcaggctgcc gcgcagcccc acacggagat cccagaagga
 301 accacagctg aagaagcagg cattggagac accccagcc tggaagacga agctgctggt
 361 cacgtgaccc aagctcgcat ggtcagtaaa agcaaagacg ggactggaag cgatgacaaa
 421 aaagccaagg gggctgatgg taaaacgaag atcgccacac cgcggggagc agcccctcca
 481 ggccagaagg gccaggccaa cgccaccagg attccagcaa aaacccgcc cgctccaaag
 541 acaccaccca gctctggtga acctccaaaa tcaggggatc gcagcggcta cagcagcccc
 601 ggctccccag gcactcccgg cagccgctcc cgcaccccgt cccttccaac cccacccacc
 661 cgggagccca agaaggtggc agtggtccgt actccaccca gtcgccgtc ttccgccaag
 721 agccgcctgc agacagcccc cgtgccatg ccagacctga gaatgtcaa gtccaagatc
 781 ggctccactg agaacctgaa gcaccagccg ggaggcggga aggtgcagat aattaataag
 841 aagctggatc ttagcaacgt ccagtccaag tgtggctcaa aggataatat caaacacgtc
 901 ccgggaggcg gcagtgtgca aatagtctac aaaccagttg acctgagcaa ggtgacctcc
 961 aagtgtggct cattaggcaa catccatcat aaaccaggag gtggccaggt ggaagtaaaa
1021 tctgagaagc ttgacttcaa ggacagagtc cagtcgaaga ttgggtccct ggacaatatc
1081 acccacgtcc ctggcggagg aaataaaaag attgaaaccc acaagctgac cttccgcgag
1141 aacgccaaag ccaagacaga ccacggggcg gagatcgtgt acaagtcgcc agtggtgtct
1201 ggggacacgt ctccacggca tctcagcaat gtctcctcca ccggcagcat cgacatggta
1261 gactcgcccc agctcgccac gctagctgac gaggtgtctg cctccctggc caagcagggt
1321 ttgtga (SEQ ID NO:4)
```

FIG. 6D

```
  1 maeprqefev medhagtygl gdrkdqggyt mhqdqegdtd aglkaeeagi gdtpsledea
 61 aghvtqarmv skskdgtgsd dkkakgadgk tkiatprgaa ppgqkgqana tripaktppa
121 pktppssgep pksgdrsgys spgspgtpgs rsrtpslptp ptrepkkvav vrtppkspss
181 aksrlqtapv pmpdlknvks kigstenlkh qpgggkvqii nkkldlsnvq skcgskdnik
241 hvpgggsvqi vykpvdlskv tskcgslgni hhkpgggqve vksekldfkd rvqskigsld
301 nithvpgggn kkiethkltf renakaktdh gaeivykspv vsgdtsprhl snvsstgsid
361 mvdspqlatl adevsaslak qgl (SEQ ID NO:5)
```

FIG. 6E

```
   1 atggctgagc ccgccagga gttcgaagtg atggaagatc acgctgggac gtacgggttg
  61 ggggacagga aagatcaggg gggctacacc atgcaccaag accaagaggg tgacacggac
 121 gctggcctga aagctgaaga agcaggcatt ggagacaccc ccagcctgga agacgaagct
 181 gctggtcacg tgacccaagc tcgcatggtc agtaaaagca aagacgggac tggaagcgat
 241 gacaaaaaag ccaaggggc tgatggtaaa acgaagatcg ccacaccgcg gggagcagcc
 301 cctccaggcc agaagggcca ggccaacgcc accaggattc cagcaaaaac cccgcccgct
 361 ccaaagacac cacccagctc tggtgaacct ccaaaatcag gggatcgcag cggctacagc
 421 agccccggct ccccaggcac tccggcagc cgctcccgca cccgtccct tccaacccca
 481 cccacccggg agcccaagaa ggtggcagtg gtccgtactc cacccaagtc gccgtcttcc
 541 gccaagagcc gcctgcagac agcccccgtg cccatgccag acctgaagaa tgtcaagtcc
 601 aagatcggct ccactgagaa cctgaagcac cagccgggag gcgggaaggt gcagataatt
 661 aataagaagc tggatcttag caacgtccag tccaagtgtg gctcaaagga taatatcaaa
 721 cacgtcccgg gaggcggcag tgtgcaaata gtctacaaac cagttgacct gagcaaggtg
 781 acctccaagt gtggctcatt aggcaacatc catcataaac caggaggtgg ccaggtggaa
 841 gtaaaatctg agaagcttga cttcaaggac agagtccagt cgaagattgg gtccctggac
 901 aatatcaccc acgtccctgg cggaggaaat aaaaagattg aaacccacaa gctgaccttc
 961 cgcgagaacg ccaaagccaa gacagaccac ggggcggaga tcgtgtacaa gtcgccagtg
1021 gtgtctgggg acacgtctcc acggcatctc agcaatgtct cctccaccgg cagcatcgac
1081 atggtagact cgccccagct cgccacgcta gctgacgagg tgtctgcctc cctggccaag
1141 cagggtttgt ga (SEQ ID NO:6)
```

FIG. 6F

```
  1 maeprqefev medhagtygl gdrkdqggyt mhqdqegdtd aglkaeeagi gdtpsledea
 61 aghvtqarmv skskdgtgsd dkkakgadgk tkiatprgaa ppgqkgqana tripaktppa
121 pktppssgep pksgdrsgys spgspgtpgs rsrtpslptp ptrepkkvav vrtppkspss
181 aksrlqtapv pmpdlknvks kigstenlkh qpgggkvqiv ykpvdlskvt skcgslgnih
241 hkpgggqvev ksekldfkdr vqskigsldn ithvpgggnk kiethkltfr enakaktdhg
301 aeivykspvv sqdtsprhls nvsstgsidm vdspqlatla devsaslakq gl
```
(SEQ ID NO:7)

FIG. 6G

```
   1 atggctgagc cccgccagga gttcgaagtg atggaagatc acgctgggac gtacgggttg
  61 ggggacagga aagatcaggg gggctacacc atgcaccaag accaagaggg tgacacggac
 121 gctggcctga agctgaaga agcaggcatt ggagacaccc ccagcctgga agacgaagct
 181 gctggtcacg tgacccaagc tcgcatggtc agtaaaagca aagacgggac tggaagcgat
 241 gacaaaaaag ccaaggggc tgatggtaaa acgaagatcg ccacaccgcg gggagcagcc
 301 cctccaggcc agaagggcca ggccaacgcc accaggattc agcaaaaaac cccgcccgct
 361 ccaaagacac cacccagctc tggtgaacct ccaaaatcag gggatcgcag cggctacagc
 421 agccccggct ccccaggcac tccggcagc cgctcccgca cccgtccct tccaaccccca
 481 cccacccggg agccaagaa ggtggcagtg gtccgtactc cacccaagtc gccgtcttcc
 541 gccaagagcc gcctgcagac agcccccgtg cccatgccag acctgaagaa tgtcaagtcc
 601 aagatcggct ccactgagaa cctgaagcac cagccgggag gcgggaaggt gcaaatagtc
 661 tacaaaccag ttgacctgag caaggtgacc tccaagtgtg gctcattagg caacatccat
 721 cataaaccag gaggtggcca ggtggaagta aaatctgaga agcttgactt caaggacaga
 781 gtccagtcga agattgggtc cctggacaat atcacccacg tccctggcgg aggaaataaa
 841 aagattgaaa cccacaagct gaccttccgc gagaacgcca agccaagac agaccacggg
 901 gcggagatcg tgtacaagtc gccagtggtg tctggggaca cgtctccacg gcatctcagc
 961 aatgtctcct ccaccggcag catcgacatg gtagactcgc ccagctcgc cacgctagct
1021 gacgaggtgt ctgcctccct ggccaagcag ggtttgtga (SEQ ID NO:8)
```

FIG. 6H

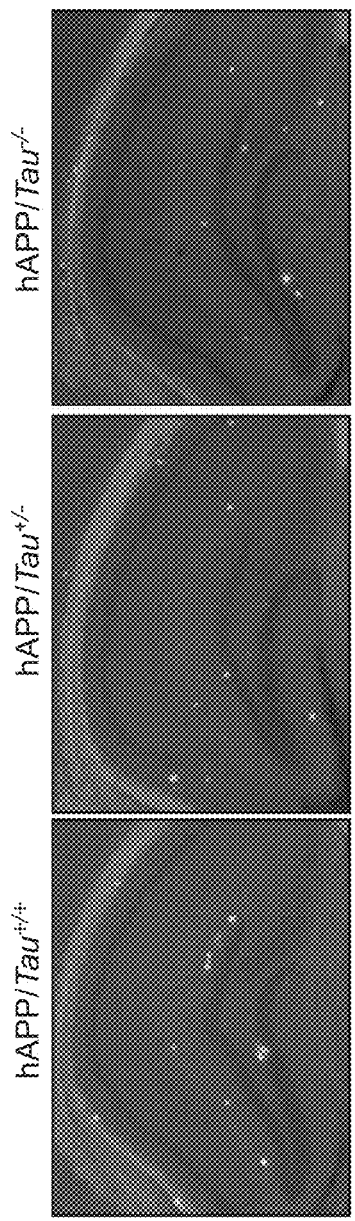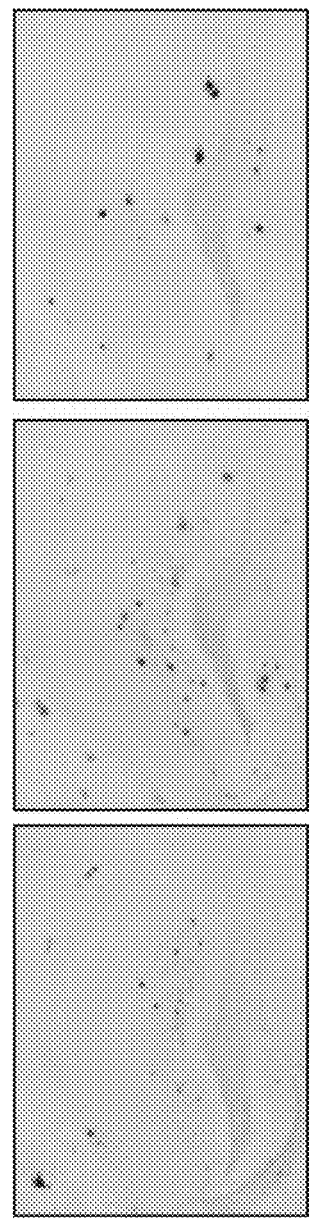
FIG. 14A  FIG. 14B  FIG. 14C  FIG. 14D
FIG. 14E  FIG. 14F  FIG. 14G  FIG. 14H

AGENTS THAT REDUCE NEURONAL OVEREXCITATION

CROSS REFERENCE

This application is a divisional of U.S. patent application Ser. No. 13/082,170, filed Apr. 7, 2011, which is a divisional of U.S. patent application Ser. No. 12/098,328, filed Apr. 4, 2008, which claims the benefit of U.S. Provisional Patent Application No. 60/922,082, filed Apr. 5, 2007, each of which application applications is incorporated herein by reference in its entirety.

STATEMENT REGARDING FEDERALLY SPONSORED RESEARCH

This invention was made with Government support under grant nos. AG022074, AG11385, and NS054811 awarded by the National Institutes of Health. The Government has certain rights in this invention.

BACKGROUND

Neuronal overexcitation is believed to underlie a wide variety of neurological conditions. Seizures are a common manifestation of neuronal overexcitation, and epilepsy is one of the most prevalent neurological conditions. Seizures also occur as a feature of many other neurological diseases. Excitotoxicity, a pathophysiological process characterized by neuronal overexcitation resulting in cellular and/or neuronal network dysfunction or death, is believed to play a role in Alzheimer's disease, Parkinson's disease, amyotrophic lateral sclerosis, Huntington's disease, stroke, and other neurological conditions.

Current drugs used to reduce excitotoxicity have been only marginally effective. In addition, use of such drugs is associated with adverse side effects. For example, excitotoxicity drugs can adversely affect normal neuronal function.

Tau is a microtubule-binding protein. Tau becomes hyperphosphorylated and undergoes other posttranslational modifications in Alzheimer's disease, aggregating into neurofibrillary tangles. Tau is a family of six proteins derived from a single gene by alternative mRNA splicing. The human brain tau isoforms range from 352 to 441 amino acids. The tau isoforms contain three or four tubulin binding domains of 31 or 32 amino acids, each in the C-terminal half, and two, one, or no inserts of 29 amino acids each in the N-terminal portion of the molecule. All of the six isoforms have been reported to be present in a hyperphosphorylated state in paired helical filaments associated with tauopathies such as Alzheimer's disease.

LITERATURE

U.S. Patent Publication No. 2004/0241854; Rapoport et al. (2002) *Proc. Natl. Acad. Sci. USA* 99:6364-6469; Dickey et al. (2006) *Mol. Neurodegener.* 1:6.

SUMMARY OF THE INVENTION

The present invention provides methods of identifying candidate agents for treating excitotoxicity-related disorders. The present invention further provides methods for treating excitotoxicity-related disorders.

BRIEF DESCRIPTION OF THE DRAWINGS

FIGS. 1A-E depict the effect of tau on water maze deficits in hAPP mice.

FIGS. 2A-E depict the effect of tau on behavioral abnormalities and premature mortality in hAPP mice.

FIG. 4A-D depict the effect of tau on excitotoxin-induced seizures.

FIGS. 6A-H depict nucleotide and amino acid sequences of various human tau isoforms.

FIGS. 14A-H depict results showing that tau reduction does not affect plaque load in young mice.

DEFINITIONS

Figure 3B:
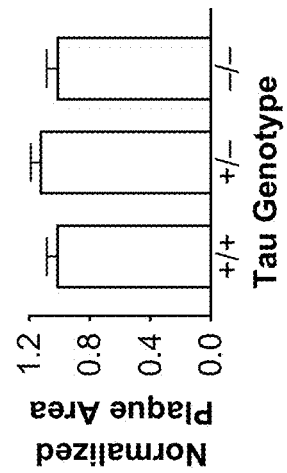
FIGS. 3A-D depict the effect of tau on Aβ plaque deposition, neuritic dystrophy, or aberrant sprouting.

The term "excitotoxicity," as used herein, refers to a pathophysiological process characterized by neuronal overexcitation, resulting in cellular dysfunction and/or neuronal network dysfunction and/or cell death.

By "nucleic acid" herein is meant either DNA or RNA, or molecules which contain both deoxy- and ribonucleotides. The nucleic acids include genomic DNA, cDNA and oligonucleotides including sense and anti-sense nucleic acids. Also siNAs, such as siRNAs, are included. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence can be at least about 18 residues long, or at least about 30 residues long, or can extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

Where a nucleic acid is said to hybridize to a recited nucleic acid sequence, hybridization is under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, or at least about 90% as stringent as the above specific stringent conditions. Other stringent hybridization conditions are known in the art and may also be employed to identify nucleic acids of this particular embodiment of the invention.

Similarly, "polypeptide" and "protein" as used interchangeably herein, and can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived.

As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of an polypeptide. Polypeptides useful in the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, non-human primate, or equine, from any source whether natural, synthetic, semi-synthetic or recombinant. In some embodiments, polypeptides comprising a sequence of a human polypeptide are of particular interest.

A "variant" of a polypeptide is defined as an amino acid sequence that is altered by one or more amino acids (e.g., by deletion, addition, insertion and/or substitution). Generally, "addition" refers to nucleotide or amino acid residues added to an end of the molecule, while "insertion" refers to nucleotide or amino acid residues between residues of a naturally-occurring molecule. The variant can have "conservative" changes, wherein a substituted amino acid has similar structural or chemical properties, e.g., replacement of leucine with isoleucine. In some instances, a variant can have "nonconservative" changes, e.g., replacement of a glycine with a tryptophan. Similar minor variations can also include amino acid deletions or insertions, or both. Guidance in determining which and how many amino acid residues may be substituted, added, inserted or deleted without abolishing biological or immunological activity can be found using computer programs well known in the art, for example, DNAStar software.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, e.g., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject," "host," "individual," and "patient" are used interchangeably herein to refer to a member or members of any mammalian or non-mammalian species that may have a need for the pharmaceutical methods, compositions and treatments described herein. Subjects and patients thus include, without limitation, humans, non-human primates, canine, feline, ungulate (e.g., equine, bovine, swine (e.g., pig)), avian, and other mammalian subjects. Humans are of particular interest.

"Mammal" means a member or members of any mammalian species, and includes, by way of example, canines; felines; equines; bovines; ovines; rodentia, etc. and primates, particularly humans. Non-human animal models, e.g., mammals, e.g. non-human primates, murines (rats, mice), lagomorpha, etc. may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

The term "biological sample" encompasses a variety of sample types obtained from an organism. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a tau gene product" includes a plurality of such gene products and reference to "the siRNA" includes reference to one or more siRNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of identifying candidate agents for treating excitotoxicity-related disorders. The present invention further provides methods of reducing excitotoxicity, and of treating excitotoxicity-related disorders.

Screening Methods

The present invention provides methods of identifying candidate agents for treating excitotoxicity-related disorders. Both in vitro and in vivo methods are provided.

In Vitro Methods

The in vitro methods generally involve contacting a cell that produces a tau gene product with a test agent in vitro; and determining the effect, if any, of the test agent on the level of the tau gene product in the cell. A test agent that reduces the level of the tau gene product in the cell is considered a candidate agent for the treatment of an excitotoxicity-related disorder. In some embodiments, a subject screening method is carried out in vitro, e.g., the cell is contacted with a test agent in vitro, and the determining step is carried out in vitro.

For example, a test agent that reduces the level of the tau gene product in the cell by at least about 10%, at least about 15%, at least about 20%, at least about 25%, at least about 30%, at least about 40%, at least about 50%, at least about 60%, at least about 70%, at least about 80%, or at least about 90%, or more, compared to the level of the tau gene product in the absence of the test agent, is considered a candidate agent for the treatment of an excitotoxicity-related disorder.

In some embodiments, a test agent that reduces the level of a tau mRNA in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of tau mRNA in the cell in the absence of the test agent, is considered a candidate agent for the treatment of an excitotoxicity-related disorder.

In some embodiments, a test agent that reduces the level of a tau polypeptide in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of tau polypeptide in the cell in the absence of the test agent, is considered a candidate agent for the treatment of an excitotoxicity-related disorder.

In some embodiments, a test agent that reduces the level of a non-hyperphosphorylated tau polypeptide in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of non-hyperphosphorylated tau polypeptide in the cell in the absence of the test agent, is considered a candidate agent for the treatment of an excitotoxicity-related disorder.

In some embodiments, a test agent that reduces the level of a non-aggregated (e.g., soluble) tau polypeptide in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of non-aggregated (e.g., soluble) tau polypeptide in the cell in the absence of the test agent, is considered a candidate agent for the treatment of an excitotoxicity-related disorder.

Tau gene products include tau polypeptides and tau nucleic acids (e.g., tau mRNA, a cDNA copy of a tau mRNA, and the like). In some embodiments, a subject method identifies agents that reduce the level of a tau polypeptide, independent of the phosphorylation state of the tau polypeptide, and independent of the aggregation state ("solubility state") of the tau polypeptide, e.g., the method identifies agents that reduce the level of both hyperphosphorylated tau and tau that is not hyperphosphorylated, and identifies agents that reduce the level of aggregated tau and non-aggregated (e.g., soluble) tau. In other embodiments, a subject method specifically identifies agents that reduce the level non-hyperphosphorylated tau, and agents that reduce the level of non-aggregated (e.g., soluble) tau. For example, in some embodiments, a subject method does not identify agents that reduce the level or activity of a kinase that phosphorylates tau.

In some embodiments, a test agent that reduces the level of a tau gene product also alters (e.g., increases or decreases) one or more of: 1) a downstream effect of tau; 2) interaction of tau with a molecule other than tau (e.g., a fyn kinase); 3) one or more physiological functions of tau, where physiological functions of tau include: a) stabilization of microtubules; b) regulation of intracellular transport and trafficking (e.g., regulation of axonal transport, regulation of dendritic transport, trafficking of organelles, and the like); and c) promoting neurite outgrowth. A reduction in the level of a tau gene product may protect newborn neurons (e.g., dentate gyrus (DG) neurons) against Aβ-induced deficits and can improve integration of such newborn neurons into the DG neuronal network. Thus, in some embodiments, a test agent that reduces the level of a tau gene product also improves integration of newborn neurons into the dentate gyrus (DG) circuitry and/or protects newborn DG neurons against Aβ-induced deficits.

A "tau polypeptide" refers to a polypeptide that binds microtubules, e.g., that binds β-tubulin; and has structural and/or amino acid sequences features as discussed in detail herein. A "tau polypeptide" refers to any tau isoform found in the central nervous system (CNS; see, e.g., Goedert and Jakes (1990) *The EMBO J.* 9:4225-4230) or in the peripheral nervous system (PNS; see, e.g., Couchie et al. (1992) *Proc. Natl. Acad. Sci. USA* 89:4378). Human tau isoforms are depicted schematically in FIG. 5. Tau polypeptides are known in the art, and amino acid sequences of a variety of tau proteins are known. See, e.g., GenBank Accession Nos. AAC04277, NP_058519, AAC04279, NP_005901, NP_058518, NP_058525, and AAH98281. Nucleotide sequences encoding such tau proteins are known in the art. See, e.g., GenBank Accession No. NM_016835 (FIG. 6B; SEQ ID NO:2), encoding the amino acid sequence depicted in FIG. 6A (GenBank AAC04277; isoform 1); GenBank Accession No. NM_005910 (FIG. 6D; SEQ ID NO:4), encoding the amino acid sequence depicted in FIG. 6C (GenBank NM_016835; isoform 2); GenBank Accession No. NM_016834 (FIG. 6F; SEQ ID NO:6), encoding the amino acid sequence depicted in FIG. 6E (GenBank NP_058518; isoform 3); GenBank Accession No. BC098281 (FIG. 6H; SEQ ID NO:8), encoding the amino acid sequence depicted in FIG. 6G (GenBank AAH98281; isoform 4).

The term "tau polypeptide" encompasses a polypeptide comprising any known tau amino acid sequence, a fragment thereof (e.g., a microtubule-binding fragment thereof), or an ortholog thereof. The term "tau polypeptide" further encompasses a polypeptide comprising an amino acid sequence having at least about 75%, at least about 80%, at least about 85%, at least about 90%, at least about 95%, at least about 98%, or at least about 99% amino acid sequence identity to any known tau polypeptide. For example, in some embodiments, a tau polypeptide comprises an amino acid sequence having at least about 75%, at least about 80%, at least about 85%, at least about 90%, at least about 95%, at least about 98%, or at least about 99% amino acid sequence identity to the amino acid sequence depicted in one or more of FIGS. 6A (SEQ ID NO:1), 6C (SEQ ID NO:3), 6E (SEQ ID NO:5), and 6G (SEQ ID NO:7).

Tau polypeptides include polypeptides comprising an amino acid sequence of from about 50 amino acids to about 758 amino acids in length (e.g., from about 50 to about 100, from about 100 to about 200, from about 200 to about 300, from about 300 to about 400, from about 400 to about 500, from about 500 to about 600, or from about 600 to about 758 amino acids in length) having at least about 75%, at least about 80%, at least about 90%, at least about 95%, at least about 98%, or at least about 99% amino acid sequence identity to a corresponding fragment of 50 amino acids to about 758 amino acids in length (e.g., from about 50 to about 100, from about 100 to about 200, from about 200 to about 300, from about 300 to about 400, from about 400 to about 500, from about 500 to about 600, or from about 600 to about 758 contiguous amino acids of the amino acid sequence set forth in SEQ ID NO:1 (and depicted in FIG. 6A).

Tau polypeptides include polypeptides comprising an amino acid sequence of from about 50 amino acids to about 440 amino acids in length (e.g., from about 50 to about 100, from about 100 to about 150, from about 150 to about 200, from about 200 to about 250, from about 250 to about 300, from about 300 to about 350, from about 350 to about 400, or from about 400 to about 440 amino acids in length) having at least about 75%, at least about 80%, at least about 90%, at least about 95%, at least about 98%, or at least about 99% amino acid sequence identity to a corresponding fragment of 50 to about 100, from about 100 to about 150, from about 150 to about 200, from about 200 to about 250, from about 250 to about 300, from about 300 to about 350, from about 350 to about 400, or from about 400 to about 440 contiguous amino acids of the amino acid sequence set forth in SEQ ID NO:3 (and depicted in FIG. 6C).

Tau polypeptides include polypeptides comprising an amino acid sequence of from about 50 amino acids to about 380 amino acids in length (e.g., from about 50 to about 100, from about 100 to about 150, from about 150 to about 200, from about 200 to about 250, from about 250 to about 300, from about 300 to about 350, or from about 350 to about 380 amino acids in length) having at least about 75%, at least about 80%, at least about 90%, at least about 95%, at least about 98%, or at least about 99% amino acid sequence identity to a corresponding fragment of 0 to about 100, from about 100 to about 150, from about 150 to about 200, from about 200 to about 250, from about 250 to about 300, from about 300 to about 350, or from about 350 to about 380 contiguous amino acids of the amino acid sequence set forth in SEQ ID NO:5 (and depicted in FIG. 6E).

Tau polypeptides include polypeptides comprising an amino acid sequence of from about 50 amino acids to about 350 amino acids in length (e.g., from about 50 to about 100, from about 100 to about 150, from about 150 to about 200, from about 200 to about 250, from about 250 to about 300, or from about 300 to about 350 amino acids in length) having at least about 75%, at least about 80%, at least about 90%, at least about 95%, at least about 98%, or at least about 99% amino acid sequence identity to a corresponding fragment of 50 to about 100, from about 100 to about 150, from about 150 to about 200, from about 200 to about 250, from about 250 to about 300, or from about 300 to about 350 contiguous amino acids of the amino acid sequence set forth in SEQ ID NO:7 (and depicted in FIG. 6G).

Active fragments (e.g., microtubule-binding fragments) of a tau polypeptide include polypeptides comprising at least about 30, at least about 60, at least about 90, or at least about 120 contiguous amino acids of a tau polypeptide having at least about 75%, at least about 80%, at least about 85%, at least about 90%, at least about 95%, at least about 98%, or at least about 99% amino acid sequence identity to the amino acid sequence set forth in one or more of: 1) amino acids 569-693 of the amino acid sequence depicted in FIG. 6A (SEQ ID NO:1); 2) amino acids 252-376 of the amino acid sequence depicted in FIG. 6C (SEQ ID NO:3); 3) amino acids 194-318 of the amino acid sequence depicted in FIG. 6E (SEQ ID NO:5); and 4) amino acids 194-287 of the amino acid sequence depicted in FIG. 6G (SEQ ID NO:7).

Figure 5:
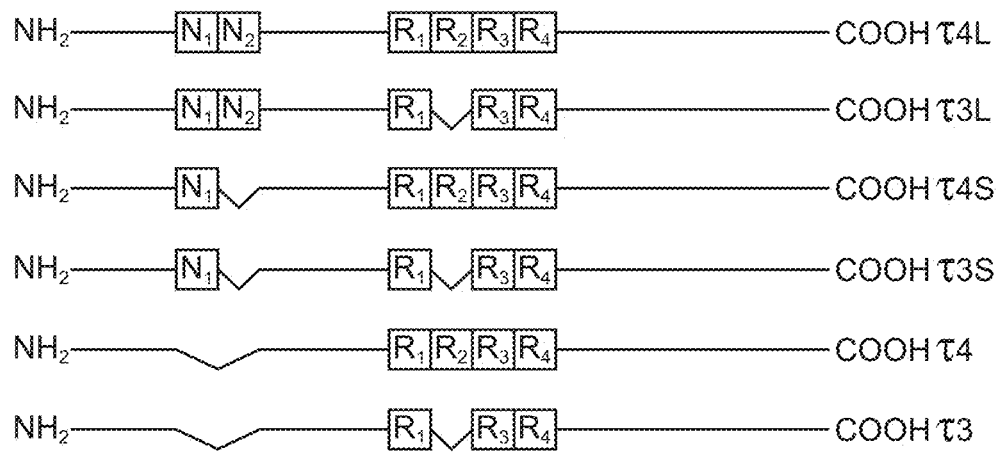
FIG. 5 presents a schematic depiction of human tau isoforms.

In some embodiments, "tau polypeptide" includes both hyperphosphorylated and non-hyperphosphorylated tau polypeptides. In other embodiments, hyperphosphorylated tau polypeptides are specifically excluded. Whether a tau polypeptide is considered to be hyperphosphorylated can be determined at the level of an individual tau polypeptide, or at the level of a population of tau polypeptides. "Hyperphosphorylated" tau also refers to a population of tau polypeptides (e.g., tau polypeptide in a cell, or in a tissue) in which the level of phosphorylation of tau is significantly higher than a normal control, e.g., the level of phosphorylation of tau is at least 20%, at least 30%, at least 40%, at least 50%, at least 60%, at least 70%, at least 80%, at least 90%, at least 100% (or 2-fold), at least 2.5-fold, at least 5-fold, at least 10-fold, at least 25-fold, at least 50-fold, or at least 100-fold, or greater than 100-fold, higher than the level of tau phosphorylation present in a population of tau polypeptides in normal individuals (e.g., individuals not having Alzheimer's disease or any other excitotoxicity-related disorder). "Non-hyperphosphorylated" tau refers to a population of tau polypeptides in which the level of phosphorylation is no more than 20% higher than a control level, e.g., a level of phosphorylation present in a population of tau polypeptides in normal individuals. Amino acid residues in tau that can be phosphorylated under physiological conditions include Ser-46, Ser-195, Ser-198, Ser-199, Ser-202, Ser-214, Ser-235, Ser-262, Ser-293, Ser-324, Ser-356, Ser-396, Ser-404, Ser-409, Thr-50, Thr-69, Thr-111, Thr-153, Thr-175, Thr-181, Thr-205, Thr-212, Thr-217, and Thr-231, where the numbering is based on the 441-amino acid form of tau (e.g., a tau isoform that includes 4 repeats and 2 insertions, as depicted in FIG. 5.

The phosphorylation state of a population of tau polypeptides can be readily determined using an immunoassay (e.g., an enzyme-linked immunosorbent assay, a protein (or "western") blot, a radioimmunoassay, immunoprecipitation, immunohistochemical staining, and the like) using one or more antibodies specific for phosphorylated tau epitopes. See, e.g., Alonso et al. (2001) J. Biol. Chem. 276:3797. For example, the following antibodies, and the amino acid residues they specifically recognize (shown in parentheses following the antibody), are suitable for use: 12E8 (Ser-P$^{262/}$ $_{356}$); M4 (THR-P$^{231}$ and Ser-P$^{235}$); PHF-1 (Ser-P$^{396/404}$); AF100 (Thr-P$^{212}$ and Ser-P$^{235}$); AF120 (Thr-P$^{181}$) and R145 (Ser-P$^{422}$). Also suitable for use is an antibody as described in, e.g., U.S. Pat. No. 6,121,003; U.S. Pat. No. 7,176,290; and U.S. Pat. No. 6,500,674.

Also included in the term "tau polypeptide" are tau fusion proteins, e.g., proteins comprising tau and a fusion partner, where suitable fusion partners include, but are not limited to, epitope tags, metal ion affinity peptides, fluorescent proteins, enzymes that yield a detectable (e.g., chromogenic, fluorescent, chemiluminescent, etc.) product. A tau fusion protein comprises a tau polypeptide fused to a heterologous polypeptide (e.g., a polypeptide other than a tau polypeptide), where the heterologous polypeptide is also referred to as a "fusion partner." In a tau fusion protein, a tau polypeptide can be fused to the N-terminus of the fusion partner, the C-terminus of the fusion partner, or internally to fusion partner. Where the fusion partner is a short (e.g., less than 50 amino acids in length) polypeptide, the fusion partner can be fused to the N-terminus of the tau polypeptide, to the C-terminus of the tau polypeptide, or at an internal site in the tau polypeptide.

Epitope tags include peptides that can be detected using an antibody (e.g., a detectably labeled antibody) that binds specifically to the peptide, e.g., to an epitope formed by the peptide. Suitable epitope tags include, but are not limited to, a glutathione-S transferase (GST) tag; an influenza hemagglutinin (HA) tag (see, e.g., Field et al., Mol. Cell. Biol., 8:2159-2165 (1988)); a c-myc tag (see, e.g., Evan et al., Molecular and Cellular Biol, 5:3610-3616 (1985)); a Herpes Simplex virus glycoprotein D (gD) tag (see, e.g., Paborsky et al., Protein Engineering, 3(6):547-553 (1990)); and a flagellin (FLAG) protein tag (e.g., a peptide comprising the amino acid sequence Asp-Tyr-Lys-Asp-Asp-Asp-Asp-Lys; SEQ ID NO:9). Suitable metal ion affinity peptides include polyhistidine peptides (e.g., (His)$_n$, where n=3-6); and the like.

Suitable enzyme fusion partners include enzymes include enzymes that act on a substrate to generate a product that generates a detectable signal (e.g., a colored product, a fluorescent product, a chemiluminescent product, etc.). Suitable enzymes include, but are not limited to, luciferase, β-galactosidase, horse radish peroxidase, alkaline phosphatase, and the like.

Suitable fusion partners include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), -galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. No. 5,292,658; U.S. Pat. No. 5,418, 155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925, 558), a GFP from species such as Renilla reniformis, Renilla mulleri, or Ptilosarcus guernyi, as described in, e.g., WO 99/49019 and Peelle et al. (2001) J. Protein Chem. 20:507-519; "humanized" recombinant GFP (hrGFP) (Stratagene); any of a variety of fluorescent and colored proteins from Anthozoan species, as described in, e.g., Matz et al. (1999) Nature Biotechnol. 17:969-973; U.S. Patent Publication No. 2002/0197676, or U.S. Patent Publication No. 2005/ 0032085; and the like.

Tau gene products include nucleic acid gene products, e.g., tau mRNA. Tau mRNAs (and corresponding cDNAs) are known in the art; and nucleotide sequences of tau mRNAs and tau cDNAs are known. See, e.g., GenBank Accession Nos. NM_016835, NM_005910, NM_016834, and BC098281. The term "tau nucleic acid gene product" encompasses a nucleic acid comprising a nucleotide sequence encoding polypeptide comprising any known tau amino acid sequence, a fragment thereof (e.g., an active fragment thereof), or an ortholog thereof. The term "tau nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to any known tau nucleic acid. For example, the term "tau nucleic acid gene product" encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to a nucleotide sequence depicted in any one of FIGS. 6A, 6C, 6E, and 6G (e.g., any one of SEQ ID NOs:1, 3, 5, and 7). Also encompassed are nucleic acids comprising nucleotide sequences encoding the above-mentioned tau fragments. Also encompassed are nucleic acids comprising nucleotide sequences encoding tau fusion proteins.

Cells that produce a tau gene product and that are suitable for use in a subject screening method include mammalian cells that normally produce a tau gene product, and mammalian cells that are genetically modified to produce a tau gene product (e.g., cells that are genetically modified with a nucleic acid comprising a nucleotide sequence encoding a tau gene product, where expression of the nucleic acid results in production of the tau gene product in the genetically modified cell).

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

By "test agent," "candidate agent," and grammatical equivalents herein, which terms are used interchangeably herein, is meant any molecule (e.g. proteins (which herein includes proteins, polypeptides, and peptides), small (i.e., 5-1000 Da, 100-750 Da, 200-500 Da, or less than 500 Da in size), or organic or inorganic molecules, polysaccharides, polynucleotides, etc.) which are to be tested for activity in reducing the level of a tau gene product in a neuronal cell.

A variety of different candidate agents may be screened by the above methods. Candidate agents encompass numerous chemical classes, e.g., small organic compounds having a molecular weight of more than 50 daltons (e.g., at least about 50 Da, at least about 100 Da, at least about 150 Da, at least about 200 Da, at least about 250 Da, or at least about 500 Da) and less than about 20,000 daltons, less than about 10,000 daltons, less than about 5,000 daltons, or less than about 2,500 daltons. For example, in some embodiments, a suitable candidate agent is an organic compound having a molecular weight in a range of from about 500 Da to about 20,000 Da, e.g., from about 500 Da to about 1000 Da, from about 1000 Da to about 2000 Da, from about 2000 Da to about 2500 Da, from about 2500 Da to about 5000 Da, from about 5000 Da to about 10,000 Da, or from about 10,000 Da to about 20,000 Da.

Candidate agents can comprise functional groups necessary for structural interaction with proteins, e.g., hydrogen bonding, and can include at least an amine, carbonyl, hydroxyl or carboxyl group, or at least two of the functional chemical groups. The candidate agents can comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In one embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate modulator prior to the assay; only candidate modulators that affect the level of a tau gene product need be identified.

In another embodiment, the candidate agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In one embodiment, candidate agents include proteins (including antibodies, antibody fragments (i.e., a fragment containing an antigen-binding region, e.g., a FAb), single chain antibodies, and the like), nucleic acids, and chemical moieties. In one embodiment, the candidate agents are naturally occurring proteins or fragments of naturally occurring proteins. Thus, for example, cellular extracts containing proteins, or random or directed digests of proteinaceous cellular extracts, may be tested. In this way libraries of prokaryotic and eukaryotic proteins may be made for screening. Other embodiments include libraries of bacterial, fungal, viral, and mammalian proteins (e.g., human proteins).

In one embodiment, the candidate agents are organic moieties. In this embodiment, as is generally described in WO 94/243 14, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As used herein, the term "determining" refers to both quantitative and qualitative determinations and as such, the term "determining" is used interchangeably herein with "assaying," "measuring," and the like.

The assay can include one or more additional reagents. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, e.g., between 4° C. and 40° C. Incubation periods are selected for optimum activity, but may also be optimized to facilitate rapid high-throughput screening. Typically between 0.1 hour and 1 hour will be sufficient.

Assays of the invention include controls, where suitable controls include a sample (e.g., a sample comprising a cell that produces a tau gene product, in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A candidate agent is assessed for any cytotoxic activity (other than anti-proliferative activity) it may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

Detecting a Level of Tau Nucleic Acid

In some embodiments, a subject screening method involves contacting a cell that produces a tau nucleic acid with a test agent, and determining the effect, if any, of the test agent on the level of the tau nucleic acid. Tau nucleic acids include tau mRNA; a cDNA copy of a tau mRNA; etc. Suitable methods for detecting the level of a tau nucleic acid in a cell include nucleic acid hybridization methods and/or nucleic acid amplification methods. For example, nucleic acid hybridization can be carried out using a nucleic acid probe that detects a tau mRNA in a cell, or a cDNA copy of a tau mRNA. Nucleic acid amplification methods can be carried out using nucleic acid primers that specifically amplify a tau mRNA (or a cDNA copy of a tau mRNA). In some embodiments, nucleic acid amplification using tau-specific primers is followed by nucleic acid hybridization using tau-specific probes.

Genetically Modified Mammalian Cells

As noted above, in some embodiments, a subject screening method will involve contacting a test agent with a mammalian cell that normally produces a tau gene product. In other embodiments, a subject screening method will involve contacting a test agent with a mammalian cell that has been genetically modified such that it produces a tau gene product. In these embodiments, an exogenous nucleic acid is introduced into a parent mammalian cell, where the exogenous nucleic acid (a "tau nucleic acid") comprises a nucleotide sequence encoding a tau gene product, generating a genetically modified mammalian cell that produces a tau gene product.

In some embodiments, a tau-encoding nucleic acid is contained within an expression vector that provides for production of a tau gene product in the genetically modified cell. The expression vector provides a transcriptional and translational initiation region, which may be inducible or constitutive, where the tau-coding region is operably linked to and under the transcriptional control of the transcriptional initiation region, and a transcriptional and translational termination region.

Any expression vector known in the art can be used to express the tau nucleic acid. An expression vector will generally include a promoter and/or other transcription control elements which are active in the cell, and appropriate termination and polyadenylation signals. Expression vectors generally have convenient restriction sites located near the promoter sequence to provide for the insertion of a nucleic acid sequence encoding a heterologous gene product (e.g., a tau gene product). A selectable marker operative in the expression host may be present.

Suitable expression vectors include, but are not limited to, viral vectors (e.g. viral vectors based on vaccinia virus; poliovirus; adenovirus (see, e.g., Li et al., Invest Opthalmol V is Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of examples: pXT1, pSG5 (Stratagene), pSVK3, pBPV, pMSG, pCMV, and pSV-LSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Non-limiting examples of suitable eukaryotic promoters (promoters functional in a eukaryotic cell) include cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the tau-encoding nucleotide sequence is operably linked to a neuron-specific control element (e.g., a promoter, an enhancer). Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; and a CMV enhancer/platelet-derived growth factor-13 promoter (see, e.g., Liu et al. (2004) *Gene Therapy* 11:52-60).

The recombinant expression vector will in some embodiments include one or more selectable markers. In addition, the expression vectors will in many embodiments contain one or more selectable marker genes to provide a phenotypic trait for selection of transformed host cells such as dihydrofolate reductase or neomycin resistance for eukaryotic cell culture.

Genetic modification of a parent mammalian cell with a tau nucleic acid, to generate a genetically modified mammalian cell, is performed using methods known in the art (see Maniatis et al., in Molecular Cloning: A Laboratory Manual, Cold Spring Harbor Laboratory, N.Y. (1982)). Exogenous DNA may be introduced into a parent cell by viral-mediated infection (retrovirus, modified herpes virus, herpes-viral, adenovirus, adeno-associated virus, and the like) or direct DNA transfection (lipofection, calcium phosphate transfection, DEAE-dextran, electroporation, and the like).

Nucleic Acid Probes

Suitable nucleic acid probes include nucleic acid probes that hybridize to and provide for detection of a tau mRNA (or cDNA). Suitable nucleic acid probes are in some embodiments in the range of between 10-50 nucleotides long, such as 10 to 50, 12 to 45, 15 to 40, 20 to 35, 25 to 30 nucleotides, and the like. For example, probes will in some embodiments be in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest in some embodiments.

A suitable probe may be coupled to a label for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Exemplary fluorescent labels include fluorescein and derivatives thereof, such as disclosed in U.S. Pat. No. 4,318, 846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Exemplary technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. In some embodiments, the probe is attached to the solid support by a linker which serves to distance the probe from the solid support. The linker is in many embodiments at least 15-30 atoms in length, or at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. In some embodiments, polymers such as functionalized polyethylene glycol are used because they do not significantly interfere with the hybridization of probe to the target oligonucleotide. In some embodiments, the linked is polyethylene glycol.

The linkages between the solid support, the linker and the probe are normally not cleaved during removal of base protecting groups under basic conditions at high temperature. Examples of suitable linkages include carbamate and amide linkages.

Examples of suitable types of solid supports for immobilization of the oligonucleotide probe include controlled pore glass, glass plates, polystyrene, avidin-coated polystyrene beads, cellulose, nylon, acrylamide gel, and activated dextran.

Nucleic Acid Primers

In some embodiments, a subject method involves amplifying a tau nucleic acid (e.g., a tau mRNA, a cDNA copy of a tau mRNA). Nucleic acid amplification methods can be carried out using nucleic acid primers that specifically amplify a tau mRNA (or a cDNA copy of a tau mRNA). In some embodiments, nucleic acid amplification using tau-specific primers is followed by nucleic acid hybridization using tau-specific probes. In general, primers provide for amplification of a tau target nucleic acid to produce a tau target nucleic acid amplification product (also referred to as an "amplicon"). Primers will in some embodiments be used in conjunction with a nucleic acid probe. 5' primers generally bind to a region to provide for amplification of the target nucleic, and in many embodiments bind to a 5' portion of the target sequence.

Target tau nucleotide sequences to which 5' and 3' primers hybridize will be separated from one another by from about 10 nucleotides to about 2277 nucleotides, e.g., from about 10 nucleotides to about 20 nucleotides, from about 20 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 100 nucleotides, from about 100 nucleotides to about 150 nucleotides, from about 150 nucleotides to about 200 nucleotides, from about 200 nucleotides to about 250 nucleotides, from about 250 nucleotides to about 300 nucleotides, from about 300 nucleotides to about 400 nucleotides, from about 400 nucleotides to about 500 nucleotides, from about 500 nucleotides to about 750 nucleotides, from about 750 nucleotides to about 1000 nucleotides, from about 1000 nucleotides to about 1500 nucleotides, from about 1500 nucleotides to about 2000 nucleotides, or from about 2000 nucleotides to about 2270 nucleotides.

The amplification product that is generated will have a length of from about 30 nucleotides to about 2270 nucleotides, e.g., from about 30 nucleotides to about 50 nucleotides, from about 50 nucleotides to about 100 nucleotides, from about 100 nucleotides to about 150 nucleotides, from about 150 nucleotides to about 200 nucleotides, from about 200 nucleotides to about 250 nucleotides, from about 250 nucleotides to about 300 nucleotides, from about 300 nucleotides to about 400 nucleotides, from about 400 nucleotides to about 500 nucleotides, from about 500 nucleotides to about 750 nucleotides, from about 750 nucleotides to about 1000 nucleotides, from about 1000 nucleotides to about 1500 nucleotides, from about 1500 nucleotides to about 2000 nucleotides, or from about 2000 nucleotides to about 2270 nucleotides.

In some embodiments, the primer sequences are in the range of between 10-75 nucleotides in length, such as 10 to 70 nucleotides, 12 to 65 nucleotides, 15 to 60 nucleotides, 20 to 55 nucleotides, 25 to 50 nucleotides, 30 to 45 nucleotides, and the like. In some embodiments, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides can be used.

In some embodiments, the first and/or the second primer comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE),6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample can then calculated where desired by comparison with the signal produced by the known standards.

Synthesis of Primers and Probes

Primers and probes described above are designed based on the sequences disclosed herein and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Detecting the Level of a Tau Polypeptide

In some embodiments, a subject method involves detecting the level of a tau polypeptide in a cell. Suitable methods for detecting the level of a tau polypeptide include immunological assays, e.g., an enzyme-linked immunosorbent assay, a radioimmunoassay, an immunoprecipitation assay, a protein ("Western") blot; assays that detect a fusion partner of a tau fusion protein; and the like.

In some embodiments, an immunological assay involves use of an antibody specific for a tau polypeptide. The anti-tau antibody can include a detectable label. An anti-tau antibody will in some embodiments be detectably labeled, e.g., with a radioisotope, an enzyme which generates a detectable product, a fluorescent protein, a chromogenic protein, and the like. An anti-tau antibody can be further conjugated to other moieties, such as members of specific binding pairs, e.g., biotin (member of biotin-avidin specific binding pair), and the like. An anti-tau antibody can also be bound to a solid support, including, but not limited to, polystyrene plates or beads, magnetic beads, test strips, membranes, and the like.

In some embodiments, the anti-tau antibody is detectably labeled, either directly or indirectly. Direct labels include radioisotopes (e.g., $^{125}$I; $^{35}$S, and the like); enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu; or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include second antibodies specific for tau-specific antibodies, wherein the second antibody is labeled as described above; and members of specific binding pairs, e.g., biotin-avidin, and the like.

In some embodiments, an anti-tau antibody comprises, covalently linked to the antibody, a protein that provides for a detectable signal. Suitable proteins include, but are not limited to, fluorescent proteins and enzymes (e.g., β-galactosidase, luciferase, horse radish peroxidase, alkaline phosphatase, etc.). Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis*, *Renilla mulleri*, or *Ptilosarcus guernyi*, as described in, e.g., WO 99/49019 and Peelle et al. (2001) *J. Protein Chem.* 20:507-519; a yellow fluorescent protein; a blue fluorescent protein; a red fluorescent protein; any of a variety of fluorescent and colored proteins from *Anthozoan* species, as described in, e.g., Matz et al. (1999) *Nature Biotechnol.* 17:969-973, U.S. Patent Publication No. 2002/0197676, or U.S. Patent Publication No. 2005/0032085; and the like.

In some embodiments, an anti-tau antibody used in a subject screening method is specific for a particular isoform of tau. In other embodiments, an anti-tau antibody used in a subject screening method cross-reacts with two or more tau isoforms. In some embodiments, an anti-tau antibody used in a subject screening method binds specifically to an epitope of a tubulin-binding repeat, e.g., the antibody binds an epitope presented by amino acid 569-693 of the amino acid sequence depicted in FIG. 6A (SEQ ID NO:1), amino acids 252-376 of the amino acid sequence depicted in FIG. 6C (SEQ ID NO:3), amino acids 194-318 of the amino acid sequence depicted in FIG. 6E (SEQ ID NO:5), or amino acids 194-287 of the amino acid sequence depicted in FIG. 6G (SEQ ID NO:7).

Tau polypeptide levels can also be measured in a genetically modified mammalian cell harboring a recombinant construct comprising a nucleotide sequence that encodes a tau fusion protein, where the fusion partner provides for a detectable signal or can otherwise be detected. For example, where the fusion partner provides an immunologically recognizable epitope (an "epitope tag"), an antibody specific for an epitope of the fusion partner can be used to detect and quantitate the level of tau. In some embodiments, the fusion partner provides for a detectable signal, and in these embodiments, the detection method is chosen based on the type of signal generated by the fusion partner. For example, where the fusion partner is a fluorescent protein, fluorescence is measured. Suitable fluorescent proteins include those mentioned above.

A candidate agent can be further analyzed in an in vivo, non-human animal model of an excitotoxic disorder. For example, a candidate agent can be administered to a tau$^{+/+}$ mouse that has been treated with an excitotoxin; and the effect, if any, of the candidate agent on the number and/or severity and/or time of onset of seizures can be measured. Excitotoxins that are suitable for use include, but are not limited to, kainate, pentylenetetrazole, and the like.

In some embodiments, a candidate agent is one that reduces the number and/or severity and/or time of onset of seizures in a non-human animal model by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared with the number and/or severity and/or time of onset of seizures in the non-human animal that has not been treated with the candidate agent.

In Vivo Methods

In some embodiments, a subject method is carried out in vivo, e.g., a test agent is administered to a non-human animal model of an excitotoxic disorder; and the effect, if any, of the test agent on a level of a tau gene product is determined. For example, a test agent is administered to a non-human animal model of an excitotoxicity-related disorder; and the effect, if any, of the test agent on the level of a tau gene product. In some embodiments, the method further comprises carrying out an assay for a readout for the excitotoxicity-related disorder. Readouts for an excitotoxicity-related disorder include, but are not limited to, a) the number and/or severity and/or time of onset of seizures; b) a behavioral deficit associated with an excitotoxicity-related disorder; and c) an abnormal level of a calcium-responsive gene product associated with an excitotoxicity-related disorder.

Suitable non-human animal models include rodents, e.g., rats and mice, that have a $tau^{+/-}$ or a $tau^{+/+}$ genotype. In some embodiments, the non-human animal model is a wild-type non-human animal; and an excitotoxin is administered to the animal. Excitotoxins that are suitable for use include, but are not limited to, kainate, pentylenetetrazole, and the like. In other embodiments, the non-human animal model is a non-human animal model of Alzheimer's disease. Non-human animal models of Alzheimer's disease are known in the art (see, e.g., U.S. Pat. Nos. 6,046,381, 6,175,057, 6,300,540, 6,455,757, 6,586,656, and 7,081,561); and a number of such animals are commercially available (e.g., from Jackson Laboratories). In other embodiments, the non-human animal model is a non-human animal model of Parkinson's disease. Non-human animal models of Parkinson's disease include the 6-OHDA (6-hydroxydopamine) model; a model as described in U.S. Patent Publication No. 2003/0056231; and the like. In other embodiments, the non-human animal model is a non-human animal model of multiple sclerosis. Examples of suitable non-human animal models also include those described in the Example, e.g., a J20 mouse; a J9 mouse; a J9/FYN mouse (e.g., $hAPP_{low}$/FYN mouse); and a TASD mouse. In some embodiments, the non-human animal model is a non-human animal model of traumatic head injury.

Whether a test agent level of a tau gene product is reduced can be determined as described above, e.g., the level of a tau gene product in a biological sample from the animal can be determined, as described above.

As noted above, in some embodiments, a readout for an excitotoxicity-related disorder is assayed, where readouts include, e.g., a) the number and/or severity and/or time of onset of seizures; b) a behavioral deficit associated with an excitotoxicity-related disorder; and c) an abnormal level of a calcium-responsive gene product associated with an excitotoxicity-related disorder. Behavioral deficits include learning deficits, memory deficits, fear reactions, and the like. Behavioral deficits can be assayed using any of a variety of well-known methods, e.g., an elevated plus maze test; a Morris water maze test; a passive avoidance test; and the like.

Calcium-responsive gene products (also referred to as "calcium-dependent gene products") that are suitable for detecting include, e.g., calcium-dependent gene products that are lower in an individual (e.g., in the dentate gyrus of the individual) having a excitotoxicity-related neurological disorder, including, e.g., calbindin, p-ERK, α-actinin II, and c-Fos; and calcium-dependent gene products that are higher in an individual (e.g., in the dentate gyrus of the individual) having a excitotoxicity-related neurological disorder, including, e.g., neuropeptide Y (NPY). See, e.g., Palop et al. (2003) *Proc. Natl. Acad. Sci. USA* 100:9572.

Treatment Methods

Methods of treating an excitotoxicity-related disorder are provided. The methods generally involve administering to an individual in need thereof an effective amount of an agent that reduces a level of a tau gene product in a neuron in the individual.

A suitable agent includes an agent that reduces the degree, frequency, or severity of at least one symptom or parameter of an excitotoxicity-related disorder by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the degree, frequency, or severity of the parameter in an individual not treated with the agent.

For example, in some embodiments, a suitable agent is an agent that reduces the number of seizures and/or that reduces the severity of seizures and/or delays the onset of seizures in an individual by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the number of seizures, severity of seizures, or time of onset of seizures in the individual not treated with the agent.

For example, in some embodiments, a suitable agent is an agent that improves a behavioral parameter (e.g., memory, cognition, learning) in an individual by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the behavioral in the individual not treated with the agent.

Agents that Reduce a Level of a Tau Gene Product

Agents that reduce a level of a tau gene product include agents that reduce the level of a tau mRNA and/or a tau polypeptide in a cell. In some embodiments, an agent that reduces the level of a tau gene product in a cell is an agent that, when contacted with a cell, reduces the level of a tau and/or a tau polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the level of the tau gene product in the cell in the absence of the agent. For example, a suitable agent includes an agent that reduces the level of a tau gene product by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the level of the tau gene product in the neuron without administration of the agent.

Suitable agents that reduce the level of a tau gene product in a cell in an individual (e.g., that reduce the level of a tau gene product in a neuron in an individual) include agents that reduce the level of a wild-type tau gene product. In some embodiments, a suitable agent is one that selectively reduces the level of a wild-type tau gene product.

In some embodiments, a suitable agent reduces the level of a tau polypeptide in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of tau polypeptide in the cell without treatment with the agent.

In some embodiments, a suitable agent reduces the level of a non-hyperphosphorylated tau polypeptide in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of non-hyperphosphorylated tau polypeptide in the cell without treatment with the agent.

In some embodiments, a suitable agent reduces the level of a non-hyperphosphorylated tau polypeptide in a tissue (e.g., a brain tissue) by at least about 10%, at least about 15%, at least about 20%, at least about 25%, at least about 30%, at least about 40%, at least about 50%, at least about 60%, at least about 70%, at least about 80%, or at least about 90%, or more, compared to the level of non-hyperphosphorylated tau polypeptide in the tissue without treatment with the agent.

In some embodiments, a suitable agent reduces the level of a non-aggregated (e.g., soluble) tau polypeptide in a cell (e.g., in a neuronal cell) by at least about 10%, at least about 15%, at least about 20%, at least about 25%, at least about 30%, at least about 40%, at least about 50%, at least about 60%, at least about 70%, at least about 80%, or at least about 90%, or more, compared to the level of non-aggregated (e.g., soluble) tau polypeptide in the cell without treatment with the agent.

In some embodiments, an agent that reduces the level of a tau gene product also alters (e.g., increases or decreases) one or more of: 1) a downstream effect of tau; 2) interaction of tau with a molecule other than tau (e.g., a fyn kinase); 3) one or more physiological functions of tau, where physiological functions of tau include: a) stabilization of microtubules; b) regulation of intracellular transport and trafficking (e.g., regulation of axonal transport, regulation of dendrite transport, trafficking of organelles, and the like); and c) promoting neurite outgrowth. A reduction in the level of a tau gene product may protect newborn neurons (e.g., dentate gyrus (DG) neurons) against Aβ-induced deficits and can improve integration of such newborn neurons into the DG neuronal network. Thus, in some embodiments, an agent that reduces the level of a tau gene product also improves integration of newborn neurons into the dentate gyrus (DG) circuitry and/or protects newborn DG neurons against Aβ-induced deficits.

A suitable agent reduces the level of a tau gene product, e.g., a tau mRNA, a tau polypeptide (e.g., a non-hyperphosphorylated tau polypeptide, a non-aggregated tau polypeptide). Agents that reduce the level or activity of a kinase that phosphorylates tau are in some embodiments specifically excluded. In addition, agents that reduce tau aggregation, or that target aggregated tau, are in some embodiments specifically excluded.

Antisense Nucleic Acids

Agents that reduce the level of a tau gene product in a cell, e.g., in a neuron, include antisense nucleic acids. For example, antisense nucleic acids can be used to down-regulate expression of a tau gene in a cell (e.g., in a neuron). The anti-sense reagent may be an antisense oligonucleotide (ODN), e.g., a synthetic ODN having chemical modifications from native nucleic acids, or nucleic acid constructs that express such anti-sense molecules as RNA. The antisense sequence is complementary to the mRNA of the targeted gene (e.g., tau), and inhibits expression of the targeted gene products. Antisense molecules inhibit gene expression through various mechanisms, e.g. by reducing the amount of mRNA available for translation, through activation of RNAse H, or steric hindrance. One or a combination of antisense nucleic acids may be administered, where a combination may comprise multiple different sequences.

Antisense nucleic acids can be produced by expression of all or a part of the target gene sequence (e.g., tau) in an appropriate vector, where the transcriptional initiation is oriented such that an antisense strand is produced as an RNA molecule. Alternatively, the antisense nucleic acid is a synthetic oligonucleotide. Antisense nucleic acids can be at least about 7, at least about 12, or at least about 20 nucleotides in length, and not more than about 500, not more than about 50, or not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides can be chemically synthesized by methods known in the art (see Wagner et al. (1993), supra, and Milligan et al., supra.) Suitable oligonucleotides can be chemically modified from the native phosphodiester structure, in order to increase their intracellular stability and binding affinity. A number of such modifications have been described in the literature, which modifications alter the chemistry of the backbone, sugars, or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Interfering Nucleic Acids

Suitable agents that reduce the level of a tau gene product in a cell include interfering nucleic acids, e.g., interfering RNA molecules. In one embodiment, reduction of a tau gene product level is accomplished through RNA interference (RNAi) by contacting a cell with a small nucleic acid molecule, such as a short interfering nucleic acid (siNA), a short interfering RNA (siRNA), a double-stranded RNA (dsRNA), a micro-RNA (miRNA), or a short hairpin RNA (shRNA) molecule, or modulation of expression of a small interfering RNA (siRNA) so as to provide for decreased levels of a tau gene product.

Interfering nucleic acids can be designed based on the nucleotide sequence of a tau-encoding nucleotide sequence. For example, in some embodiments, a tau-encoding nucleotide sequence as set forth in one or more of SEQ ID NOs:2, 4, 6, and 8 is used to design an interfering nucleic acid.

The term "short interfering nucleic acid," "siNA," "short interfering RNA," "siRNA," "short interfering nucleic acid molecule," "short interfering oligonucleotide molecule," or "chemically-modified short interfering nucleic acid molecule" as used herein refers to any nucleic acid molecule capable of inhibiting or down regulating gene expression, for example by mediating RNA interference "RNAi" or gene silencing in a sequence-specific manner. Design of RNAi molecules when given a target gene is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6):509-16; Xie et al. Drug Discov Today. 2006 January; 11(1-2):67-73; Grunweller et al. Curr Med. Chem. 2005; 12(26):3143-61; and Pekaraik et al. Brain Res Bull. 2005 Dec. 15; 68(1-2):115-20. Epub 2005 Sep. 9.

Methods for design and production of siRNAs to a desired target are known in the art, and their application to tau genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Non limiting examples of target sites for design of siNA molecules for tau include the following:

```
Target Region 1:
5'-AATCACACCCAACGTGCAGAA-3'
(SEQ ID NO: 10; corresponding to nucleotides 918-938 of the
nucleotide sequence depicted in FIG. 6B and set forth in
SEQ ID NO: 2);

Target Region 2:
5'-AACTGGCAGTTCTGGAGCAAA-3'
(SEQ ID NO: 11; corresponding to nucleotides 1344-1364 of the
nucleotide sequence depicted in FIG. 6B and set forth in
SEQ ID NO: 2);

Target Region 3:
5'-gacctg aagaatgtca agtccaagat cggctccact gagaacctga agcaccagcc gggaggcggg aaggtgcaga taattaataa gaagctg-3'
(SEQ ID NO: 12; corresponding to nucleotides 1705-1797 of the
nucleotide sequence depicted in FIG. 6B and set forth in
SEQ ID NO: 2);

Target Region 4:
5'-gat cttagcaacg tccagtccaa gtgtggctca aaggataata tcaaacacgt cccgggaggc ggcagtgtgc aaatagtcta caaaccagtt-3'
(SEQ ID NO: 13; corresponding to nucleotides 1798-1890 of the
nucleotide sequence depicted in FIG. 6B and set forth in
SEQ ID NO: 2);

Target Region 5:
5'-gacctgagca aggtgacctc caagtgtggc tcattaggca acatccatca taaaccagga ggtggccagg tggaagtaaa atctgagaag ctt-3'
(SEQ ID NO: 14; corresponding to nucleotides 1891-1983 of the
nucleotide sequence depicted in FIG. 6B and set forth in
SEQ ID NO: 2);

Target Region 6:
5'-gacttca aggacagagt ccagtcgaag attgggtccc tggacaatat cacccacgtc cctggcggag gaaataaaaa gattgaaacc cacaagctg-3'
(SEQ ID NO: 15; corresponding to nucleotides 1984-2079 of the
nucleotide sequence depicted in FIG. 6B and set forth in
SEQ ID NO: 2);

Target Region 7:
5'-aagtcgccgt cttccgccaa gagccgcctg-3'
(SEQ ID NO: 16; corresponding to nucleotides 1651-1680 of the
nucleotide sequence depicted in FIG. 6B and set forth in
SEQ ID NO: 2);
```

```
Target Region 8:
5'-gccaagacag accacggggc ggagatcgtg-3'
(SEQ ID NO: 17; corresponding to nucleotides 2101-2130 of the
nucleotide sequence depicted in FIG. 6B and set forth in
SEQ ID NO: 2).

The following nucleotide sequences are specifically excluded:
                                                (SEQ ID NO: 18)
1) 5'-tcgaagtgatggaagatcacgc-3';

(SEQ ID NO: 19)
2) 5'-cagccgggagtcgggaaggtgc-3';

SEQ ID NO: 20)
3) 5'-acgtcctcggcggcggcagtgtgc-3';

SEQ ID NO: 21)
4) 5'-acgtctccatggcatctcagc-3';

SEQ ID NO: 22)
5) 5'-gtggccagatggaagtaaaatc-3';

SEQ ID NO: 23)
6) 5'-gtggccacatggaagtaaaatc-3';
and

SEQ ID NO: 24)
7) 5'-gtggccagatgcaagtaaaatc-3'.
```

It should be understood that the sequences provided above are the target sequences of the mRNAs encoding the target gene, and that the siRNA oligonucleotides used would comprise a sequence complementary to the target.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 base pairs to about 30 base pairs, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 nucleotides to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at both the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of tau.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Administration and Formulation of Agents

Formulation of an agent of interest for delivery to a subject, as well as method of delivery of agents (including siNA molecules, antisense nucleic acids, etc., as described above), are available in the art. These include formulations and delivery methods to effect systemic delivery of an agent, as well as formulation and delivery methods to effect local delivery of an agent (e.g., to effect to a particular organ or compartment (e.g., to effect delivery to the central nervous system (CNS), etc.)). Agents can be formulated to include a delivery vehicle for administration to a subject, carriers and diluents and their salts, and/or can be present in pharmaceutically acceptable formulations.

Suitable formulations at least in part depend upon the use or the route of entry, for example parenteral, oral, or transdermal. The term "parenteral" as used herein includes percutaneous, subcutaneous, intravascular (e.g., intravenous), intramuscular, or intrathecal injection, or infusion techniques, and the like. Formulations include pharmaceutically acceptable salts of an agent of interest, e.g., acid addition salts.

In one embodiment, compounds are administered to a subject by systemic administration in a pharmaceutically acceptable composition or formulation. By "systemic administration" is meant in vivo systemic absorption or accumulation of drugs in the blood stream to facilitate distribution through the body. Systemic administration routes include, e.g., intravenous, subcutaneous, portal vein, intraperitoneal, inhalation, oral, intrapulmonary, and intramuscular.

Formulations of agents can also be administered orally, topically, parenterally, by inhalation or spray, or rectally in dosage unit formulations containing pharmaceutically acceptable carriers, adjuvants and/or vehicles. Pharmaceutically acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated herein by reference. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom at least to some extent) of a disease state. The pharmaceutically effective dose depends on the type of disease, the composition used, the route of administration, the type of subject being treated, subject-dependent characteristics under consideration, concurrent medication, and other factors that those skilled in the medical arts will recognize. Generally, an amount between 0.1 mg/kg and 100 mg/kg body weight/day of active ingredients is administered.

Local injection into a tissue defining a biological compartment (e.g., brain, ventricles, intrathecal space, spinal cord, synovial space, and the like) is also of interest.

Where pulmonary delivery is desired, agents can be administered by, e.g., inhalation of an aerosol or spray dried formulation administered by an inhalation device (e.g., nebulizer, insufflator, metered dose inhaler, and the like), providing uptake of the agent into pulmonary tissues. Solid particulate compositions containing respirable dry particles of micronized compositions containing a compound of interest (e.g., nucleic acid) can be prepared by standard techniques. A solid particulate composition can optionally contain a dispersant which serves to facilitate the formation of an aerosol. A suitable dispersant is lactose, which can be blended with the agent in any suitable ratio, such as a 1 to 1 ratio by weight. The active ingredient typically in about 0.1 to 100 w/w of the formulation. The agent can be delivered as a suspension or solution formulation, and may involve use of a liquified propellant, e.g., a chlorofluorocarbon compound such as dichlorodifluoromethane, trichlorofluoromethane, dichlorotetrafluoroethane and mixtures thereof. Aerosol formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, for example US 2004/0037780, and U.S. Pat. No. 6,592,904; U.S. Pat. No. 6,582,728; U.S. Pat. No. 6,565,885, each of which are incorporated herein by reference.

Formulations and methods of delivery of agents to hematopoietic cells, including monocytes and lymphocytes, are known in the art, see, e.g., Hartmann et al., 1998, J. Phamacol. Exp. Ther., 285(2), 920-928; Kronenwett et al., 1998, Blood, 91(3), 852-862; Filion and Phillips, 1997, Biochim. Biophys. Acta., 1329(2), 345-356; Ma and Wei, 1996, Leuk. Res., 20(11/12), 925-930; and Bongartz et al., 1994, Nucleic Acids Research, 22(22), 4681-8. Such methods, as described above, include the use of free compound (e.g., oligonucleotide), cationic lipid formulations, liposome formulations including pH sensitive liposomes and immunoliposomes, and bioconjugates including oligonucleotides conjugated to fusogenic peptides, for delivery of compounds into hematopoietic cells.

Formulations and methods of delivery of agents to the skin or mucosa are known in the art. Such delivery systems include, e.g., aqueous and nonaqueous gels, creams, multiple emulsions, microemulsions, liposomes, ointments, aqueous and nonaqueous solutions, lotions, patches, suppositories, and tablets, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Delivery to the central nervous system (CNS) and/or peripheral nervous system can be accomplished by, for example, local administration of nucleic acids to nerve cells. Conventional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Other approaches can include the use of various transport and carrier systems, for example though the use of conjugates and biodegradable polymers. See also, U.S. Pat. No. 6,180,613; WO 04/013280, describing delivery of nucleic acid molecules to the CNS, which are incorporated herein by reference.

Oral administration can be accomplished using pharmaceutical compositions containing an agent of interest formulated as tablets, lozenges, aqueous or oily suspensions, dispersible powders or granules, emulsion, hard or soft capsules, or syrups or elixirs. Such oral compositions can contain one or more such sweetening agents, flavoring agents, coloring agents or preservative agents in order to provide pharmaceutically elegant and palatable preparations. Tablets, which can be coated or uncoated, can be formulated to contain the active ingredient in admixture with non-toxic pharmaceutically acceptable excipients, e.g., inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. Where a coating is used, the coating delays disintegration and absorption in the gastrointestinal tract and thereby provides a sustained action over a longer period.

Where the formulation is an aqueous suspension, such can contain the active agent in a mixture with a suitable excipient(s). Such excipients can be, as appropriate, suspending agents (e.g., sodium carboxymethylcellulose, methylcellulose, hydropropyl-methylcellulose, sodium alginate, polyvinylpyrrolidone, gum tragacanth and gum acacia); dispersing or wetting agents; preservatives; coloring agents; and/or flavoring agents.

Suppositories, e.g., for rectal administration of agents, can be prepared by mixing the agent with a suitable non-irritating excipient that is solid at ordinary temperatures but liquid at the rectal temperature and will therefore melt in the rectum to release the drug. Such materials include cocoa butter and polyethylene glycols.

Dosage levels can be readily determined by the ordinarily skilled clinician, and can be modified as required, e.g., as required to modify a subject's response to therapy. In general dosage levels are on the order of from about 0.1 mg to about 140 mg per kilogram of body weight per day. The amount of active ingredient that can be combined with the carrier materials to produce a single dosage form varies depending upon the host treated and the particular mode of administration. Dosage unit forms generally contain between from about 1 mg to about 500 mg of an active ingredient.

The agents can be administered to a subject in combination with other therapeutic compounds, e.g., so as to increase the overall therapeutic effect.

Of particular interest are siNAs, as described above. Exemplary formulations and methods for the delivery of nucleic acid molecules are known in the art. For example, nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. U.S. 2002130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalacto-samine (PEI-PEG-triGAL) derivatives. In one embodiment, the nucleic acid molecules of the invention are formulated as described in U.S. Patent Application Publication No. 20030077829, incorporated by reference herein in its entirety.

In one embodiment, a siNA molecule is complexed with membrane disruptive agents such as those described in US 2001/0007666, incorporated by reference herein in its entirety. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety. In one embodiment, a siNA molecule is complexed with delivery systems as described in US 2003/077829, WO 00/03683 and WO 02/087541, each incorporated herein by reference.

Alternatively, certain siNA molecules of the instant invention can be expressed within cells from eukaryotic promoters (e.g., promoters that are functional in a eukaryotic cell) (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45. Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856.

Where the siNA is an RNA molecule, the siNA can be expressed from transcription units inserted into a vector. The recombinant vectors can be DNA plasmids, non-viral vectors or viral vectors. siNA expressing viral vectors can be constructed based on, but not limited to, adeno-associated virus, retrovirus, adenovirus, or alphavirus. The recombinant vectors capable of expressing the siNA molecules can be delivered as described above, and provide for transient or stable expression. For example, such vectors can include: 1) a transcription initiation region; 2) optionally, a transcription termination region; and 3) a nucleic acid sequence encoding at least one strand of an siNA molecule, wherein the sequence is operably linked to the initiation region and the termination region in a manner that allows expression and/or delivery of the siNA molecule.

In some embodiments, an active agent is formulated for crossing the blood-brain barrier. The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the CNS may require the use of drug delivery strategies. Delivery of therapeutic agents to the CNS can be achieved by several methods.

One method relies on neurosurgical techniques. In the case of gravely ill patients such as those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991) *J. Cereb. Blood Flow Metab.* 11:638-643; and Gennuso et al. (1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, α-cyclodextrin, β-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Nall. Acad. Sci. USA* 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

In some embodiments, multiple doses of an active agent are administered. The frequency of administration of an active agent can vary depending on any of a variety of factors, e.g., severity of the symptoms, etc. For example, in some embodiments, an active agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an active agent r, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, a subject method involves administration of two or more different agents. For example, in some embodiments, a subject method involves administration of an agent that reduces the level of a tau gene product in a neuron in an individual; and administration of at least a second agent. For example, in the treatment of Alzheimer's disease, a subject method can involve administering combined effective amounts of an agent that reduces the level of a tau gene product in a neuron; and an agent selected from Aricept® (donepezil HCl), Exiba® (memantine HCl), Exelon™ (rivastigmine), galantamine, and Reminyl™ (extended release galantamine hydrobromide). An agent that reduces the level of a tau gene product can be administered in the same formulation as the second agent, or in a different formulation from the second agent. An agent that reduces the level of a tau gene product can be administered in the same or a different dosing regimen as the second agent.

The methods are useful for treating a variety of neurotoxicity-related disorders, including, but not limited to, Alzheimer's disease, Parkinson's disease, seizures, multiple sclerosis, epilepsy, amyotrophic lateral sclerosis, and Huntington's disease. The methods are also useful for treating traumatic head injury.

Subjects Suitable for Treatment

Individuals suitable for treatment with a subject method include, but are not limited to, individuals who have been diagnosed with a neurotoxicity-related disorder; individuals who have been treated for a neurotoxicity-related disorder, but who have failed to respond to the treatment; and individuals who have been treated for a neurotoxicity-related disorder, and who have relapsed. Suitable subjects include individuals who have experienced head injury.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Effect of Tau Reduction on Excitotoxic Seizure

Materials and Methods

Mice.

The J20 line (1), which expresses an hAPP minigene with the Swedish (K670M/N671L) and Indiana (V717F) familial Alzheimer's disease (AD) mutations under control of the PDGF promoter, was crossed with Tau$^{-/-}$ mice (2). Studies were conducted on sibling offspring from hAPP/Tau$^{+/-}$× Tau$^{+/-}$ matings. Both males and females were used, except for the water maze, where only males were tested. A total of 454 mice (66-83 per genotype), analyzed in seven separate cohorts, were tested in behavioral and/or neuropathological experiments.

Mice expressing lower levels of hAPP (hAPP$_{low}$, line J9) and mice expressing a transgene for the murine Src-family tyrosine kinase FYN (line N8) were crossed to tau knockout mice. hAPPlow/Tau$^{-/-}$ mice and FYN/Tau$^{-/-}$ mice were crossed to produce bigenic (and nontransgenic control) mice on a tau-deficient background, and these mice were compared with bigenic (and nontransgenic control) mice produced from a cross of hAPPlow and FYN transgenic mice with normal tau levels (Tau$^{+/+}$).

All mice were on an inbred C57BL/6J background. Mice were kept on a 12-hr light/12-hr dark cycle and with ad libitum access to food and water. The studies were approved by the Institutional Animal Care and Use Committee of the University of California, San Francisco, and conducted in compliance with the National Institutes of Health's "Guide for the Care and Use of Laboratory Animals." All experiments were performed by examiners blinded to the genotypes or treatments of the mice.

Water Maze.

The water maze pool (diameter, 122 cm) contained opaque water (18° C.) with a 14-cm-square platform submerged 2 cm below the surface. For cued training sessions, a black-and-white striped mast was mounted above the platform. Mice were trained to locate the platform over 6 sessions (2 per day, 4 hours apart) each with 2 trials (15 min apart). The platform location was changed for each session. Hidden platform training began 3 days later and included 10 sessions (2 per day, 4 hours apart) each with 3 trials (15 min apart). Platform location remained constant in hidden platform sessions and entry points were changed semirandomly between trials. Before beginning the fourth day of hidden platform training, a 60-s probe trial was performed during which the platform was removed. The entry point for probe trials was in the quadrant opposite the target quadrant. An additional probe trial was conducted 72 h after the fifth day of hidden platform training. Performance was monitored with an EthoVision video-tracking system (Noldus Information Technology, Wageningen, The Netherlands).

Y Maze.

The Y-maze was constructed of black plastic walls 10 cm high. It consisted of three compartments (10 cm×10 cm) connected with 4 cm×5 cm passages. The mouse was placed in one of the compartments and allowed to move freely for 6 min. An arm entry was manually recorded when all four paws entered the compartment. After testing of each mouse, the maze was thoroughly cleaned to standardize odors.

New Cage Exploration.

Mice were placed in a clean, empty cage for 5 min under normal room light and allowed to explore. Every 5 sec, an examiner recorded whether the mouse was active (e.g., walking, jumping, or rearing) or mostly inactive (e.g., sniffing or still).

Plus Maze.

Plus maze testing was performed as described (3). Briefly, after habituation to dim lighting in the testing room for 30 min, mice were individually placed at the center of the apparatus (Hamilton-Kinder, Poway, Calif.) and allowed to explore for 10 min. The time spent and distance moved in each of the arms were determined by infrared beam breaks. After testing of each mouse, the apparatus was thoroughly cleaned to standardize odors.

Immunoblotting.

Hippocampi were homogenized in RIPA buffer including protease and phosphatase inhibitors, sonicated briefly, and spun for 10 min at 15,000×g. Protein concentrations were determined with the Coomassie Plus system (Pierce). Prior to sample loading, 2% sodium chloride and 5% β-mercaptoethanol were added, samples were heated to 100° C. for 10 minutes, incubated on ice for 30 minutes, and centrifuged for 15 minutes at 12,000×g at 4° C., as described (4). Sample buffer was added to the heat-stable supernatant and loaded on Novex gels (Invitrogen). Antibodies used were monoclonal non-phosphoselective anti-tau clone 5E2 (1:1000; Upstate Biotechnology), monoclonal anti-hAPP clone 8E5 (1:1000; Peter Seubert, Elan Pharmaceuticals), monoclonal anti-phospho-tau Thr181 clone AT270 (1:3000; Innogenetics, Gent, Belgium), monoclonal anti-phospho-tau Ser202 clone CP13 (1:40, Peter Davies, Albert Einstein College of Medicine), monoclonal anti-phospho-tau Thr231 clone CP9 (1:25, Peter Davies), monoclonal anti-phospho-tau Ser262 clone 12E8 (1:4000, Peter Seubert), monoclonal anti-phospho-tau Ser396/404 clone PHF1 (1:100, Peter Davies), or monoclonal anti-tubulin clone B-5-1-2 (Sigma, St. Louis, Mo.). Blots were quantified with ImageQuant 5.2 (Molecular Dynamics).

Protein fractionation and Aβ*56 detection in hAPP mice were performed as described (5). Briefly, total protein (100 µg) from the RIPA soluble fraction was separated on 10.5-20% Tricine gels and transferred to nitrocellulose membrane (0.2 µm pore size, Bio-Rad). Biotinylated 6E10 antibody (1:1000; Signet, Dedham, Mass.) and ExtrAvidin (1:5000; Sigma) were used for immunoblotting.

Aβ ELISA.

Guanidine-solubilized hippocampal homogenates were assayed as described (6). The $A\beta_{1-42}$ ELISA used antibodies 21F12 and 3D6. The $A\beta_{1-x}$ ELISA used antibodies 266 and 3D6.

Histopathology.

Immunohistochemistry was performed as described (7) on floating 30-μm sliding microtome sections. Aβ deposits were stained with biotinylated monoclonal antibody 3D6 (1:500; Elan Pharmaceuticals, South San Francisco, Calif.) using avidin-biotin/peroxidase methods (Vector Laboratories, Burlingame, Calif.). Other assays used unconjugated primary antibodies, including monoclonal anti-GAP43 clone GAP-7B10 (1:400; Sigma), CP13, and PHF1, with a biotinylated secondary antibody. Images were acquired with a digital microscope (Axiocam, Carl Zeiss). Percent area and densitometric quantifications were performed using the Bioquant software package (BIOQUANT Image Analysis Corporation).

For double labelling of amyloid plaques and dystrophic neurites, floating sections were stained with monoclonal anti-hAPP antibody 8E5 (1:1000, Peter Seubert, Elan Pharmaceuticals), mounted on glass slides, and stained with 0.015% thioflavin-S. Images were collected with a confocal microscope (Biorad).

Calbindin immunostaining was performed with rabbit anti-calbindin (1:15,000; Swant, Bellinzona, Switzerland), and NPY was stained with rabbit anti-neuropeptide Y (1:8,000; ImmunoStar, Hudson, Wis.).

Aβ Treatment of Primary Neuron Cultures.

Cortices were isolated from Sprague-Dawley rat pups (Charles River Laboratories, Wilmington, Mass.) on postnatal day 0-1. Cells were plated at 160,000 cells/ml in plating medium containing Dulbecco's modified Eagle's medium, 10% fetal bovine serum, 0.5 mM Glutamax, 100 units/ml penicillin, and 100 μg/ml streptomycin. Fibrillar Aβ was prepared as previously described (8) by incubating 100 μM Aβ in 10 mM HCl for 24 h at 37° C. Cells were treated with 20 μM fibrillar Aβ after 5 days in culture and harvested after 48 hr treatment.

Excitotoxicity Assessment.

Drugs were dissolved in PBS and delivered by intraperitoneal injection. Pentylenetetrazole (PTZ, Sigma, St. Louis, Mo.) was used at a concentration of 5 mg/ml and a dose of 40 mg/kg. Kainate (Tocris, Ellisville, Mo.) was used at a concentration of 2 mg/ml and doses ranging from 20-40 mg/kg. For mice given PTZ, each mouse was placed in a cage and observed for 20 min after administration, with video recording. An investigator blinded to genotype analyzed the videotapes to quantify the time course and severity of seizures according to published scales (9, 10). Seizures severity scores were: 0=normal behavior; 1=immobility; 2=generalized spasm, tremble, or twitch; 3=tail extension; 4=forelimb clonus; 5=generalized clonic activity; 6=bouncing or running seizures; 7=full tonic extension; 8=death. For mice given KA, each mouse was placed in a cage and observed for 3 hours after administration. An investigator blinded to genotype quantified the time course and severity of seizures according to published scales (11); the percentage of mice attaining stage 6 (generalized tonic-clonic seizures) is presented.

CCI and Wire Hang Test.

For the controlled cortical impact (CCI) testing, male mice, $Tau^{+/+}$ and $Tau^{-/-}$ (n=22 for each genotype) were used. Mice underwent pre-testing on a wire hang test shortly before CCI to ensure groups were balanced for baseline performance. For each group, 12 mice had CCI and 10 had sham surgery. Mice were tested again on the wire hang 1, 4, 7, 9, 14, and 29 days after CCI. Briefly, mice were placed on a wire suspended about 18 inches above the benchtop between to wooden rods. Mice were placed on the rod and videotaped. An observer blinded to genotype and treatment scored the performance on a scale of 1-5 (Hall et al. (1988) J Neurosurg 68:456-461). One month after injury, mice underwent testing for seizure thresholds as described above.

Statistical Analysis.

A value of P<0.05 was considered significant. Error bars represent standard error of the mean. Survival data (FIG. 2E) was analyzed with Kaplan-Meier statistics and post-hoc log rank tests. Fisher's exact test was used to analyze occurrence of fatal status epilepticus after PTZ injection. Logistic regression was used to generate and compare dose-response curves for the proportion of mice seizing after KA administration (FIG. 4D). For other experiments, genotype differences were analyzed by ANOVA (repeated measures where indicated), using the Tukey test for post-hoc comparisons.

Results

Deposits of amyloid-β peptide (Aβ) and tau are the pathological hallmarks of Alzheimer's disease (AD). Treatments aimed at Aβ production, clearance, and aggregation are all in clinical trials. However, interest in tau as a target has been muted, partly because tau pathology seems to occur downstream of Aβ (1-4). Also, tau is posttranslationally modified in AD (5-8), and debate continues about which modifications to target. Reducing overall tau levels is an alternative approach (9). Tau haplotypes driving slightly higher tau expression increase AD risk (10). The effect of reducing endogenous tau expression on cognitive deficits in transgenic mice expressing human amyloid precursor protein (hAPP) with familial AD mutations that increase Aβ production was determined.

hAPP mice (11) were crossed with $Tau^{-/-}$ mice (12) and the effects of hAPP/Aβ in mice with two ($hAPP/Tau^{+/+}$), one ($hAPP/Tau^{+/-}$), or no ($hAPP/Tau^{-/-}$) endogenous tau alleles, compared to $Tau^{+/+}$, $Tau^{+/-}$, and $Tau^{-/-}$ mice without hAPP, were examined. Tau reduction did not affect hippocampal hAPP expression, and conversely, hAPP did not affect hippocampal tau levels. The six genotypes showed no differences in weight, general health, basic reflexes, sensory responses, or gross motor function.

To test learning and memory, the Morris water maze was used. In the cued version, mice learn to find the target platform using a conspicuous marker placed directly above it. At 4-7 months of age, $Tau^{+/+}$, $Tau^{+/-}$, and $Tau^{-/-}$ mice learned quickly, but as expected (13, 14), $hAPP/Tau^{+/+}$ mice took longer to master this task (FIG. 1A; P<0.001). In contrast, $hAPP/Tau^{+/-}$ and $hAPP/Tau^{-/-}$ mice performed at control levels.

The more difficult hidden platform version of the water maze demands spatial learning. Mice without hAPP learned this task over 3 days of training regardless of tau genotype, whereas $hAPP/Tau^{+/+}$ mice showed no evidence of learning until days 4-5 (P<0.001; FIG. 1B). Notably, $hAPP/Tau^{+/-}$ mice were less impaired than $hAPP/Tau^{+/+}$ mice (P<0.02), and $hAPP/Tau^{-/-}$ mice did not differ from controls without hAPP (FIG. 1B). Probe trials, in which the platform was removed and mice were given 60 sec to explore the pool, confirmed the beneficial effect of tau reduction (FIG. 1C-E). In an initial probe trial 24 h after three days of training, $hAPP/Tau^{+/+}$ mice had no apparent spatial memory of the platform location, crossing the target platform location no more than they crossed equivalent areas in non-target quadrants (FIG. 1D). However, $hAPP/Tau^{-/-}$ mice, like mice without hAPP, did cross the target platform location more often (P<0.01, FIG. 1D). After two additional days of training, hAPP/Tau$^{+/-}$ mice also had more target than non-target crossings (P<0.01), while hAPP/Tau$^{+/+}$ mice still showed no spatial learning and memory (FIG. 1E). Thus, tau reduction gene dose-dependently ameliorates hAPP/Aβ-induced water maze learning and memory deficits.

FIG. 1. Tau reduction prevented water maze deficits in hAPP mice (n=7-11 mice per genotype, age 4-7 months). (A) Cued platform learning curves. Day "0" indicates performance on the first trial, and subsequent points represent average of all daily trials. Performance differed by genotype (RMANOVA: P<0.001; hAPP×Tau interaction, P=0.058). In post-hoc comparisons, only hAPP/Tau$^{+/+}$differed from groups without hAPP(P<0.001). (B) Hidden platform learning curves differed by genotype (RMANOVA: P<0.001; hAPP×Tau interaction, P<0.02). In post-hoc comparisons, hAPP/Tau$^{+/+}$differed from all groups without hAPP (P<0.001); hAPP/Tau$^{+/-}$ differed from hAPP/Tau$^{+/+}$(P<0.02) and groups without hAPP(P<0.01); hAPP/Tau$^{-/-}$ differed from hAPP/Tau$^{+/+}$(P<0.001) but not from any group without hAPP. (C-D) Probe trial 24-hr after completion of 3 days of hidden platform training. (C) Representative path tracings. (D) Number of target platform crossings vs. crossings of the equivalent area in the other three quadrants differed by genotype (target crossing×genotype interaction, P<0.001). In post-hoc comparisons, all genotypes except hAPP/Tau$^{+/+}$ and hAPP/Tau$^{+/-}$ exhibited preference for the target location over equivalent areas in the other three quadrants (*P<0.05; P<0.01; *P<0.001). (E) Probe trial 72-hr after completion of 5 days of hidden platform training. Target platform preference differed by genotype (target crossing×genotype interaction, P<0.001; target crossing×hAPP×tau interaction, P<0.05). In post-hoc comparisons, all genotypes except hAPP/Tau$^{+/+}$exhibited preference for the target location (P<0.01; *P<0.001).

Increased exploratory locomotor activity is seen after entorhinal cortex lesions and may reflect deficits in spatial information processing (15); hAPP mice show similar hyperactivity (14). hAPP/Tau$^{+/+}$mice were hyperactive in the Y maze (P<0.001; FIG. 2A), a new cage (P<0.05; FIG. 2B), and the elevated plus maze (P<0.001; FIG. 2C). In contrast, these abnormalities were not seen in hAPP/Tau$^{+/-}$ and hAPP/Tau$^{-/-}$ mice (FIG. 2A-C). To determine if the benefits afforded by tau reduction were sustained, we examined older mice. Hyperactivity persisted in hAPP/Tau$^{+/+}$mice and remained absent in hAPP/Tau$^{-/-}$ mice at 12-16 months (P<0.05; FIG. 2D).

Premature death of unclear etiology is also observed in hAPP mice (P<0.005; FIG. 2E; ref. 16, 17). Again, both hAPP/Tau$^{-/-}$ and hAPP/Tau$^{+/-}$ mice were protected from this early mortality. Thus, tau reduction prevented major Aβ-dependent adverse effects in hAPP mice. Several plausible mechanisms by which tau reduction might exert protective effects were examined; and an unexpected role for tau was discovered.

FIG. 2. Tau reduction prevented behavioral abnormalities and premature mortality in hAPP mice. (A) Total arm entries during a 6-min exploration of the Y maze (n=49-58 mice per genotype; age 4-7 months; ANOVA: genotype effect, P<0.0001; hAPP×Tau interaction, P<0.0001; ***P<0.001 vs groups without hAPP). (B) Percent of time spent active during a 5-min exploration of a new cage (n=7-14 mice per genotype; age 4-7 months; ANOVA: genotype effect, P<0.01; hAPP×Tau interaction, P<0.05; *P<0.05 vs groups without hAPP). (C) Total distance travelled in both open and closed arms during a 10-min exploration of the elevated plus maze (n=49-59 mice per genotype; age 4-7 months; ANOVA: genotype effect, P<0.0001; hAPP×Tau interaction, P<0.05; ***P<0.001 vs groups without hAPP). (D) Total distance travelled during exploration of elevated plus maze (n=6-13 mice per genotype; age 12-16 months; ANOVA: hAPP effect, P<0.01; hAPP×Tau interaction, P=0.079; *P<0.05 vs. groups without hAPP). (E) Kaplan-Meier survival curves showing effect of tau reduction on premature mortality in hAPP mice. All genotyped mice in the colony (n=887) were included in the analysis. By log-rank comparison, only hAPP/Tau$^{+/+}$ mice differed from all other groups (P<0.005).

Figure 3D:
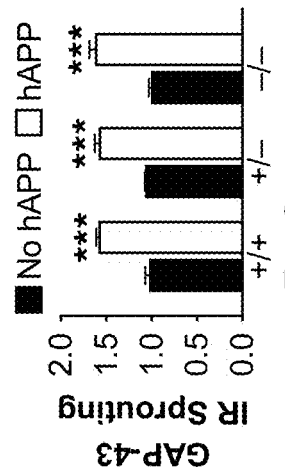
Figure 3A:
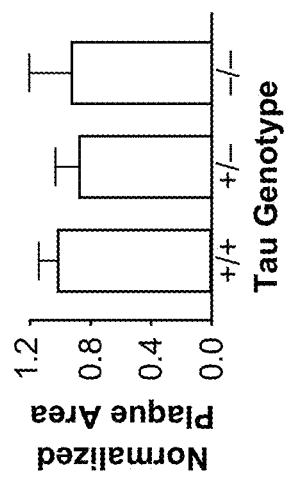

The possibility that tau reduction simply altered Aβ levels or aggregation was ruled out. Tau reduction did not alter hAPP expression, soluble Aβ$_{1-x}$ or Aβ$_{1-42}$ levels, or the Aβ$_{1-42}$/Aβ$_{1-x}$ ratio. In addition, hAPP/Tau$^{+/+}$, hAPP/Tau$^{+/-}$, and hAPP/Tau$^{-/-}$ mice had similar plaque load at 4-7 months and 14-18 months (FIG. 3A-B). It was also found no effect of tau reduction on levels of Aβ*56, a specific Aβ assembly linked to memory deficits (18). Thus, the beneficial effects of reducing tau were observed without detectable changes in Aβ burden, suggesting that tau reduction uncouples Aβ from downstream pathogenic mechanisms.

Next, abnormal forms of tau that might act as downstream effectors of Aβ in hAPP/Tau$^{+/+}$mice were looked for. Major AD-related phosphorylation sites in human tau are conserved in murine tau, including those phosphorylated by proline-directed kinases, such as GSK-3β and cdk5, or by microtubule affinity-regulating kinase (MARK). Changes in murine tau phosphorylation at these sites are easily detected, for example after brief hypothermia (ref. 19). However, in hippocampal homogenates of 4-7-month-old hAPP/Tau$^{+/+}$ mice, no changes were found in tau phosphorylation at proline-directed kinase sites, including Thr181, Ser202, Thr231, and Ser396/404, or at the primary site for MARK, Ser262. Generation of neurotoxic tau fragments has also been implicated as a mechanism of Aβ toxicity (20). Tau-deficient primary neurons are resistant to Aβ-induced degeneration (3, 21), apparently because Aβ toxicity in vitro involves production of a 17-kD tau fragment (20). The presence of a 17-kD tau fragment in lysates of Aβ-treated primary neurons was confirmed; however, no abnormal tau proteolysis was found in hippocampal homogenates from hAPP mice, suggesting that the neuroprotective effects of tau reduction in the two systems are mechanistically different. The relative lack of modified tau also distinguishes our model from transgenic lines overexpressing tau with mutations that cause frontotemporal dementia, but not AD, in humans (2, 4, 22). In this study, reduction of endogenous, wildtype tau protected hAPP mice against Aβ-dependent cognitive impairments, and this did not involve the elimination of a large pool of tau with typical AD-associated modifications. These experiments did not rule out the possibility that other types of tau modification, or a small pool of modified tau in a restricted subcellular compartment or cellular population, may play a role downstream of Aβ.

Figure 3C:
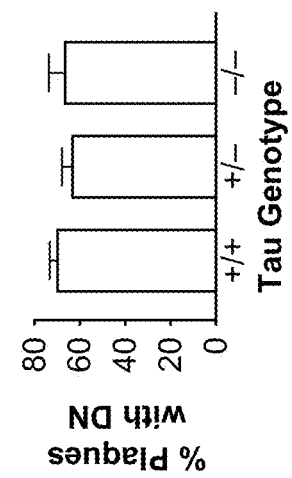

To begin addressing this possibility, brain sections from Tau$^{+/+}$and hAPP/Tau$^{+/+}$ mice were stained with phospho-tau antibodies. Little difference overall was seen between Tau$^{+/+}$ and hAPP/Tau$^{+/+}$ mice in phospho-tau immunoreactivity, but did observe scattered phospho-tau-positive punctae in dystrophic neurites surrounding amyloid plaques. The question was asked whether the benefits of tau reduction in hAPP mice could relate to prevention of neuritic dystrophy, which may contribute to AD-related cognitive decline (23). Despite the differences in their behavior, hAPP/Tau$^{+/+}$, hAPP/Tau$^{+/-}$, and hAPP/Tau$^{-/-}$ mice had similar amounts of neuritic dystrophy (FIG. 3C). Thus, tau is not required for the formation of plaque-associated dystrophic neurites. Given that tau reduction prevented behavioral deficits but not neuritic dystrophy, these may represent parallel, rather than causally linked, disease manifestations, or tau reduction may act downstream of neuritic dystrophy.

Tau has a well-characterized role in axonal outgrowth (12), so it was tested whether tau reduction prevented the aberrant sprouting of hippocampal axons observed in AD (24) and hAPP mice (17). Similar degrees of sprouting were observed, regardless of tau genotype (FIG. 3D). Thus, while tau reduction affected important outcome measures related to Aβ-induced neuronal dysfunction, not all effects of Aβ were blocked.

FIG. 3. Tau reduction did not change Aβ plaque deposition, neuritic dystrophy, or aberrant sprouting. (A) Thioflavin-S staining of hippocampal amyloid plaques in hAPP mice. Percent of hippocampal area covered by plaques was normalized to the mean value in hAPP/Tau$^{+/+}$ mice (n=6-11 mice per genotype; age 14-18 months). (B) Immunostaining of hippocampal Aβ deposits in hAPP mice. Percent of hippocampal area covered by plaques was normalized to the mean value in hAPP/Tau$^{+/+}$ mice (n=6-11 mice per genotype; age 14-18 months). (C) Double-labelling of hippocampus for dystrophic neurites (antibody 8E5, red) and amyloid plaques (thioflavin-S, green) in hAPP mice aged 14-18 months, with quantification of dystrophic neurites expressed as percent of thioflavin-S positive plaques with surrounding neuritic dystrophy (n=9-11 mice per genotype). (D) GAP43 immunostaining of aberrant axonal sprouting in the molecular layer of the dentate gyrus (oml, outer molecular layer; mml, middle molecular layer; iml, inner molecular layer; dgc, dentate granule cells). Bracket highlights GAP43-positive sprouting in the outer molecular layer of hAPP mice. Sprouting was quantified by densitometry and normalized (n=7-14 mice per genotype; age 4-7 months; ***P<0.001 vs groups without hAPP).

Excitotoxicity is implicated in the pathogenesis of AD (25, 26). Consistent with the increased incidence of seizures in AD patients (27), TgCRND8 hAPP mice are more susceptible to the GABA$_A$ receptor antagonist pentylenetetrazole (PTZ) (28). Using a similar paradigm, we found that hAPP/Tau$^{+/+}$ mice were also abnormally sensitive to PTZ, with 20% suffering fatal status epilepticus at a dose non-lethal to mice without hAPP (P<0.05). Tau reduction prevented this effect, as no hAPP/Tau$^{+/-}$ or hAPP/Tau$^{-/-}$ mice died. Seizures in hAPP/Tau$^{+/-}$ and hAPP/Tau$^{-/-}$ mice were less severe and occurred at longer latencies than in hAPP/Tau$^{+/+}$ mice (P<0.01; FIG. 4A-B).

Tau reduction also increased resistance to PTZ in hAPP-nontransgenic mice, lowering seizure severity and delaying seizure onset (P<0.01; FIG. 4A,C). To confirm that tau reduction could reduce aberrant neuronal overexcitation, mice were challenged with excitotoxic doses of the glutamate receptor agonist kainate. As expected, intraperitoneal injection of kainate dose-dependently induced seizures in Tau$^{+/+}$ mice (FIG. 4D). In contrast, Tau$^{+/-}$ and Tau$^{-/-}$ mice were resistant to kainate across a range of doses (P<0.05; FIG. 4D). Thus, tau modulates sensitivity to excitotoxins and may be involved in regulating neuronal activity. The excitoprotective effect of tau reduction in mice without hAPP is more likely related to a physiological function of tau than to the removal of a pathological form of the protein. Sensitization of neurons to Aβ by physiological forms of tau could explain why tau reduction is effective in hAPP/Tau$^{+/+}$ mice despite their lack of obvious tau modifications.

FIG. 4. Tau reduction increased resistance to excitotoxin-induced seizures. (A) Tau reduction lowered seizure severity after a single i.p. injection of PTZ (40 mg/kg; n=10-11 mice per genotype; age 4-7 months; ANOVA: Tau effect, P<0.0001). Seizures were less severe in hAPP/Tau$^{+/-}$ and hAPP/Tau$^{-/-}$ mice than in hAPP/Tau$^{+/+}$ mice (**P<0.01 vs. hAPP/Tau$^{+/+}$). Seizures were also less severe in Tau$^{-/-}$ mice than in Tau$^{+/+}$ mice ($^{\#\#}$P<0.01 vs. Tau$^{+/+}$). (B-C) Latency to reach each stage of seizure severity after PTZ administration. (B) PTZ-induced seizures occurred more rapidly in hAPP/Tau$^{+/+}$ mice than hAPP/Tau$^{+/-}$ and hAPP/Tau$^{-/-}$ mice (RMANOVA: P<0.01). (C) Tau reduction also slowed the onset of PTZ-induced seizures in mice without hAPP (RMANOVA: P<0.001). (D) After a single i.p. injection of kainate at the doses indicated, occurrence of generalized tonic-clonic seizures was scored. Tau reduction lowered susceptibility to kainate, shifting dose-response curves to the right (n=19-24 mice per genotype; age 2-5 months; Logistic regression: P<0.05).

No adverse effects of tau reduction on health or cognition in mice were found; and the fact that even partial tau reduction robustly protected mice from Aβ and excitotoxic agents highlights its benefits in reducing neuronal overexcitation.

Figure 7A:
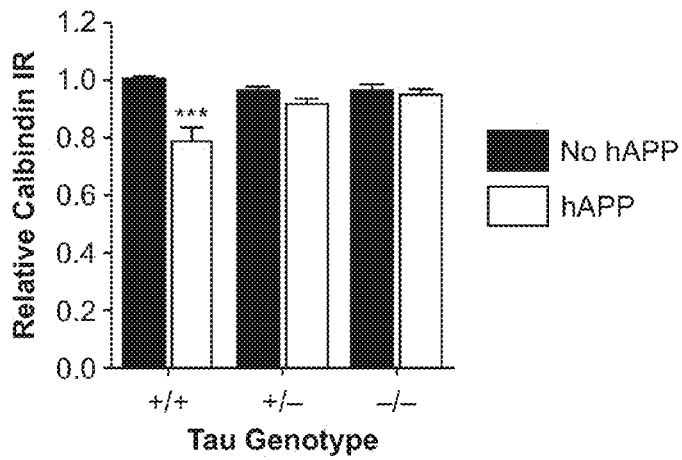
FIGS. 7A-C depict the effect of tau on hAPP/Aβ-induced changes in calbindin and NPY.
Figure 7B:
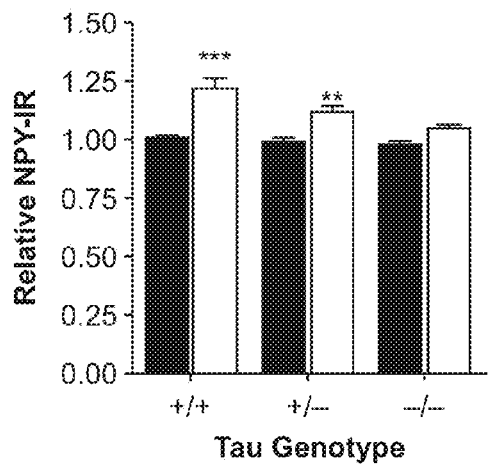
Figure 7C:
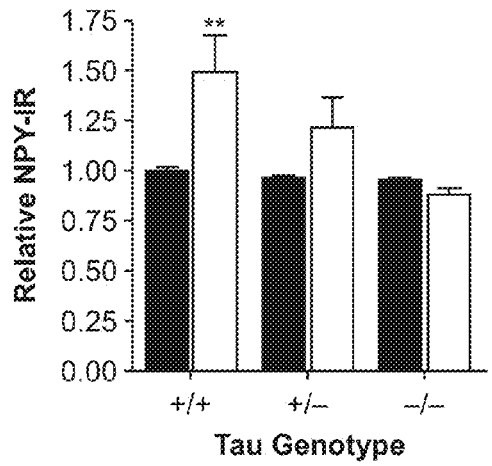

The effects of tau reduction on network excitability were examined. Neuronal network dysfunction, with imbalance between excitatory and inhibitory circuits, may contribute to AD-related cognitive impairment (Palop et al., 2006) and is found in multiple AD mouse models. One feature of such network dysfunction is depletion of calbindin in dentate granule cells, a neuroprotective response to overexcitation (Nägerl et al., 2000) that occurs in both AD patients and hAPP mice (Palop et al., 2003). It was predicted that if tau reduction blocks the overexcitation in J20 mice, then compensatory upregulation of inhibitory circuits would be unnecessary, and would also be prevented. The expected calbindin depletion in hAPP/Tau$^{+/+}$ mice (P<0.001; FIG. 7A-C) was observed, but there were no changes in calbindin in hAPP/Tau$^{+/-}$ and hAPP/Tau$^{-/-}$ mice, providing evidence that tau reduction ameliorates Aβ-induced network dysfunction. Many lines of hAPP mice also develop ectopic expression of neuropeptide Y (NPY) in the dentate gyrus. Like calbindin depletion, aberrant NPY expression is a form of plasticity associated with compensating for neuronal overexcitation (Vezzani et al., 1999). High levels of ectopic NPY in the dentate gyrus and mossy fibers of hAPP/Tau$^{+/+}$ mice were observed, but less in hAPP/Tau$^{+/-}$ mice and none in hAPP/Tau$^{-/-}$ mice (FIG. 7A-C). The absence of compensatory changes in calbindin and NPY with tau reduction further supports the hypothesis that tau reduction prevents excitotoxic network dysfunction.

FIG. 7A-C. Tau reduction prevents hAPP/Aβ-induced changes in calbindin and NPY. hAPPJ20 mice were crossed with Tau$^{-/-}$ mice for two generations to produce sibling offspring with varying levels of tau expression (columns) and hAPP (rows). Brain sections from mice age 4-7 months were immunostained for calbindin or NPY and immunoreactivity was quantified by densitometry. Calbindin depletion in the dentate gyrus was observed in hAPPJ20/Tau$^{+/+}$ mice, but not in hAPPJ20/Tau$^{+/-}$ or hAPPJ20/Tau$^{-/-}$ mice (quantification in the molecular layer of the dentate gyrus; N=25-40 mice per genotype; hAPP×Tau interaction, P<0.0001; *P<0.001 vs. groups without hAPP.) Increased NPY expression was prominent in hAPPJ20/Tau$^{+/+}$ mice, subtle in hAPPJ20/Tau$^{+/-}$ mice, and absent in hAPPJ20/Tau$^{-/-}$ mice (N=9-13 mice per genotype). Similar patterns of NPY immunoreactivity were seen in the dentate gyrus molecular layer (hAPP×Tau interaction, P<0.02; *P<0.001, P<0.01 vs. groups without hAPP) and the mossy fibers (hAPP×Tau interaction, P<0.02; P<0.01 vs. groups without hAPP).

Figure 8:
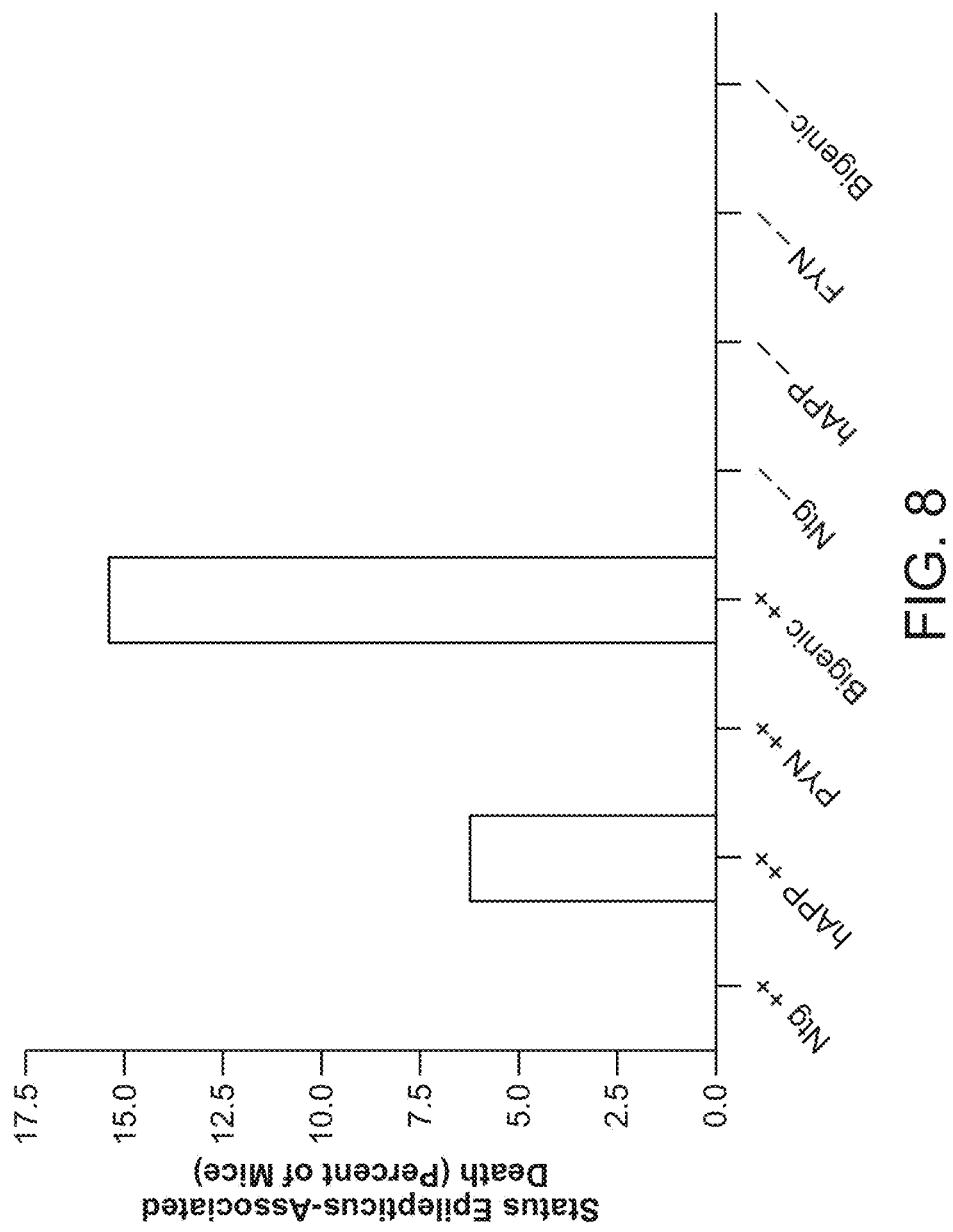
FIG. 8 depicts the effect of tau reduction on neuronal function in hAPP$_{low}$/FYN bigenic mice.

FIG. 8. Tau reduction prevents excitotoxicity in a separate AD mouse model, bitransgenic mice expressing low levels of Aβ and high levels of FYN tyrosine kinase. The low-expressing hAPP mice used in this experiment (J9 line) have only very subtle Aβ-induced neuronal dysfunction). However, when crossed with FYN transgenic mice to make hAPP$_{low}$/FYN bigenic mice, deficits are severe and similar to those observed in the high-expressing hAPP mice (Chin et al., 2004; Chin et al., 2005). These bigenic mice also have increased sensitivity to PTZ, with status-epilepticus-associated mortality at doses non-lethal to nontransgenic mice (P<0.02). In contrast, after tau reduction, both hAPP$_{low}$ and bigenic mice are resistant to PTZ.

Figure 9:
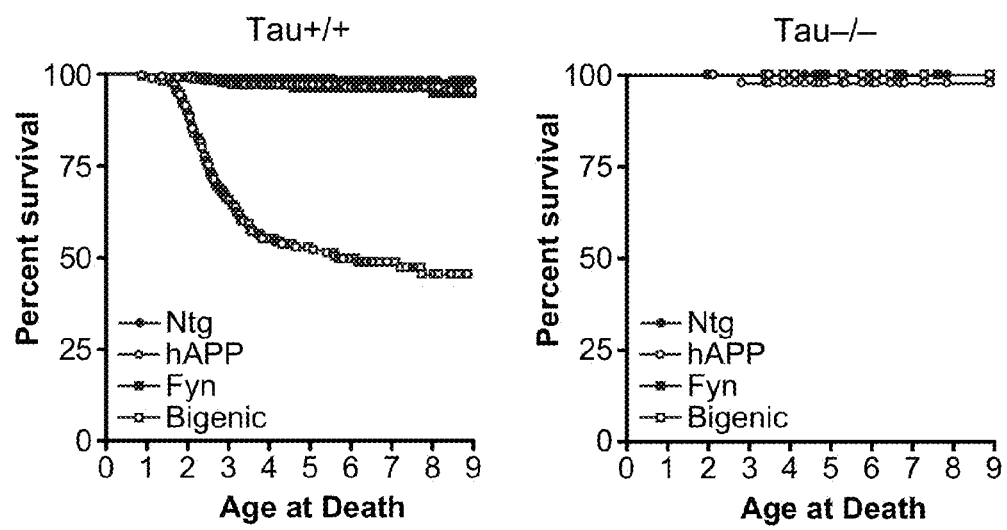
FIG. 9 depicts the effect of tau reduction on mortality in hAPPlow/FYN bigenic mice.

FIG. 9. Tau reduction blocks early mortality in hAPPlow/FYN bigenic mice. Like in other hAPP lines, the bigenic model has high levels of early mortality. In contrast, after tau reduction, bigenic mice have normal survival.

Figure 10A:
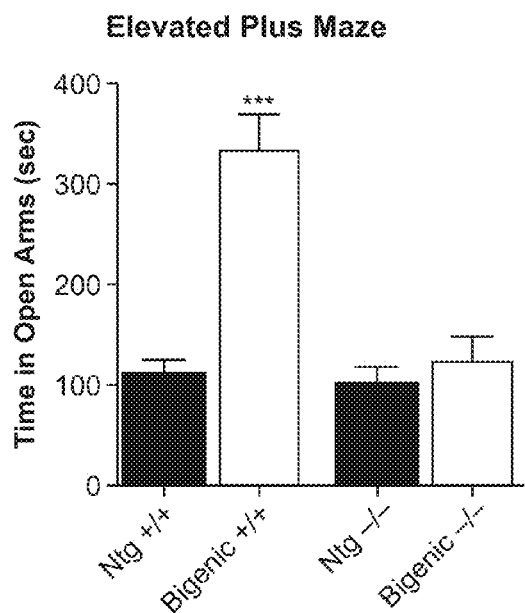
FIGS. 10A-C depict the effect of tau reduction on behavioral deficits in hAPP/FYN bigenic mice.
Figure 10B:
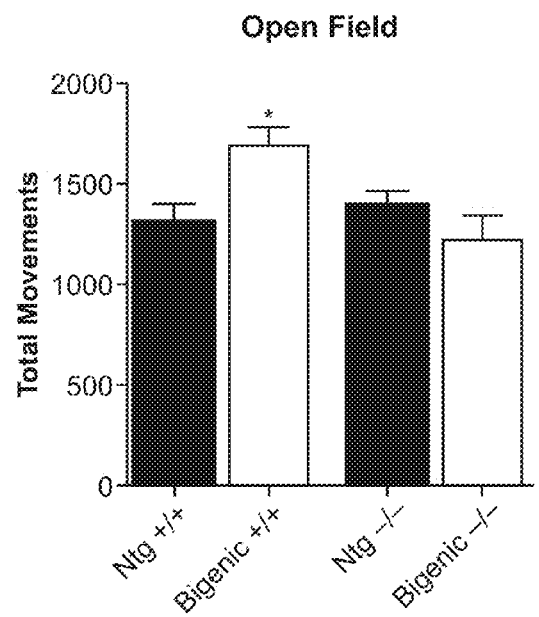
Figure 10C:
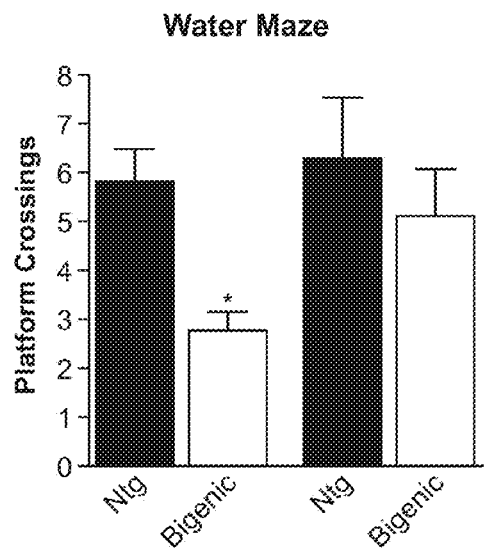

FIGS. 10A-C. Tau reduction prevents behavioral deficits in hAPP/FYN bigenic mice. (A) In the elevated plus maze, bigenic mice with normal tau expression have abnormal levels of exploration in the open arms. This abnormality is blocked by tau reduction. (B) In the open field, bigenic mice with normal tau expression are hyperactive. This abnormality is blocked by tau reduction. (C) In the Morris water maze, bigenic mice with normal tau expression exhibit poor spatial learning and memory, crossing the target platform location fewer times than nontransgenic littermates. This abnormality is blocked by tau reduction.

Figure 11:
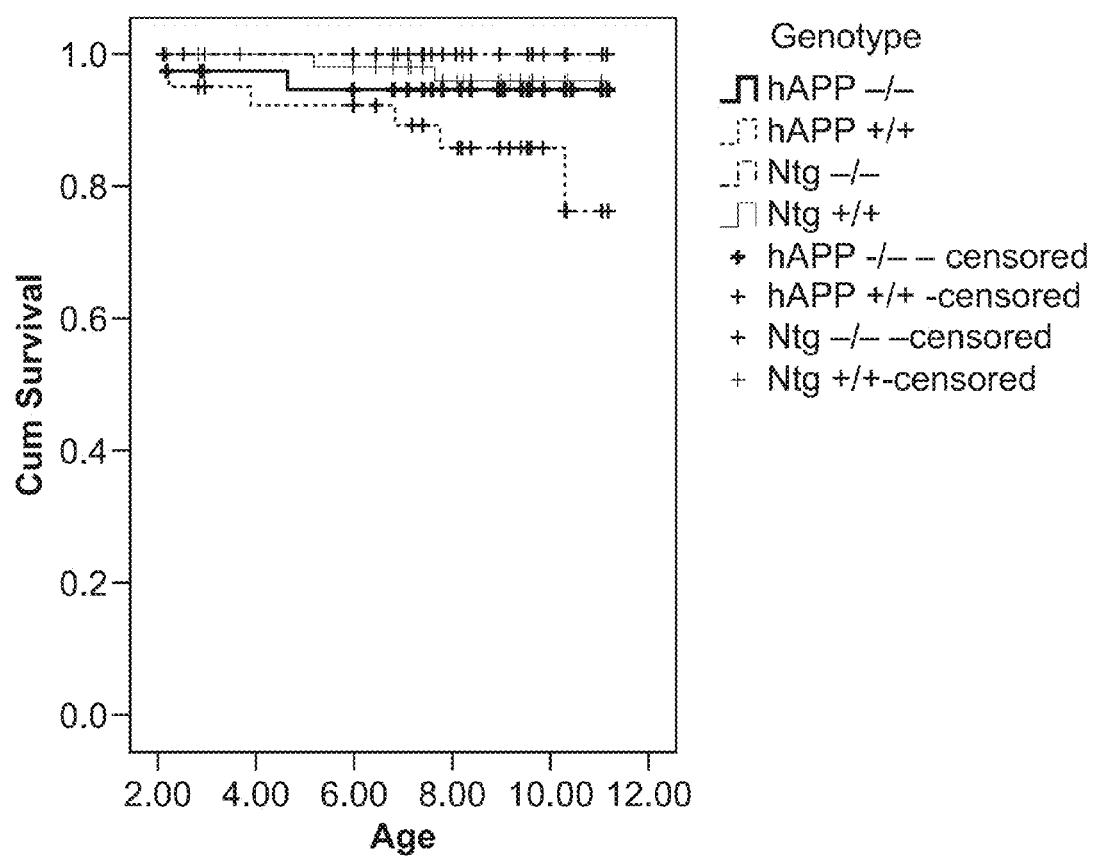
FIG. 11 depicts the effect of tau reduction on mortality in TASD mice.

FIG. 11. Tau reduction prevents early mortality in TASD mice. A distinct line of hAPP mice (TASD line) was crossed with tau knockout mice. The TASD line expresses hAPP from a different promoter (Thy1 vs. PDGF in the J20 and J9 line) and with different FAD mutations (Swedish and London vs. Swedish and Indiana in the J20 and J9 line). TASD mice with normal tau levels have increased early mortality (P<0.02), but this abnormality is not seen after tau reduction.

Figures 15A, 15B:
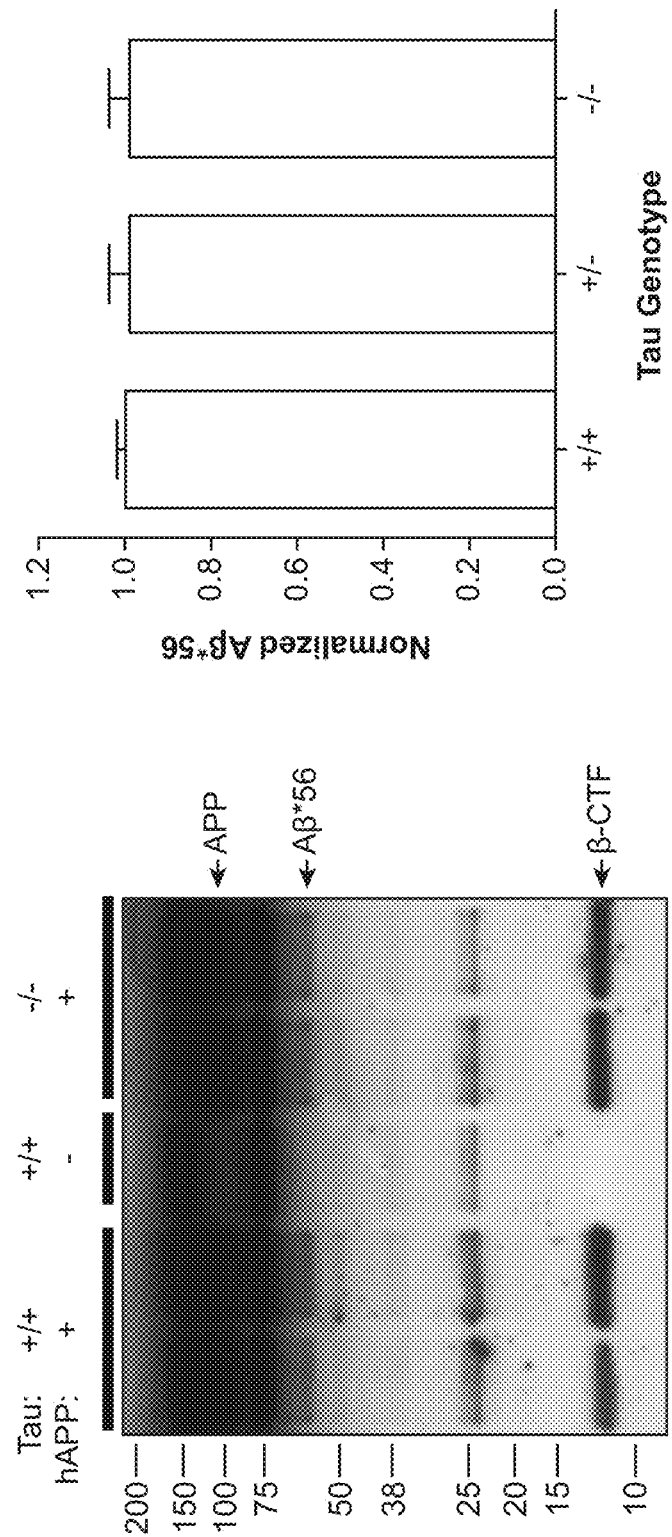
FIGS. 15A and B depict results showing that tau reduction does not affect levels of Aβ*56.

To investigate the mechanism(s) by which tau reduction prevents neuronal dysfunction in hAPP mice, the possibility that tau reduction simply altered Aβ levels or aggregation was ruled out. Tau reduction did not alter hAPP expression (FIGS. 12A-C), soluble Aβ$_{1-x}$ or Aβ$_{1-42}$ levels, or the Aβ$_{1-42}$/Aβ$_{1-x}$ ratio (FIGS. 13A-C). In addition, hAPP/Tau$^{+/+}$, hAPP/Tau$^{+/-}$, and hAPP/Tau$^{-/-}$ mice had similar plaque load at 4-7 months (FIGS. 14A-H) and 14-18 months (FIG. 3A-B). No effect of tau reduction on levels of Aβ*56, a specific Aβ assembly linked to memory deficits (Leslie et al. (2006) Nature 440:352-357), was found (FIGS. 15A and B). Thus, the beneficial effects of reducing tau were observed without detectable changes in Aβ burden, suggesting that tau reduction uncouples Aβ from downstream pathogenic mechanisms.

Figure 12A:
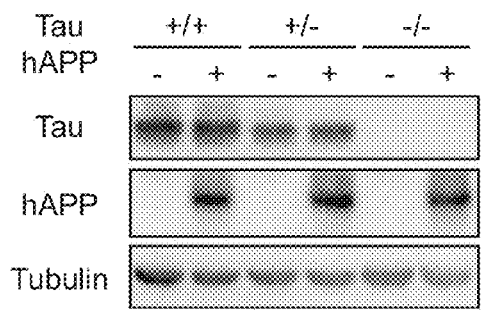
FIGS. 12A-C depict tau and hAPP levels in hippocampal homogenates from mice of various genotypes.
Figure 12B:
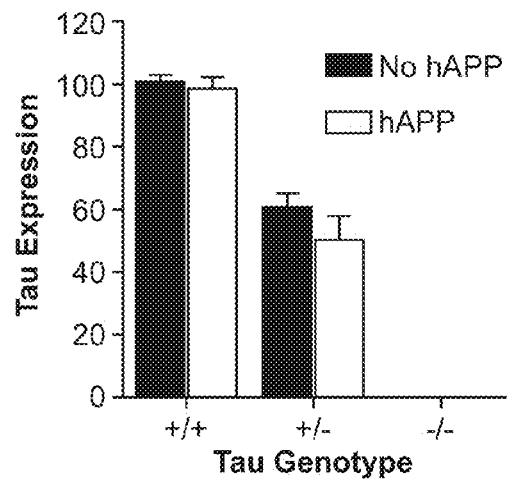
Figure 12C:
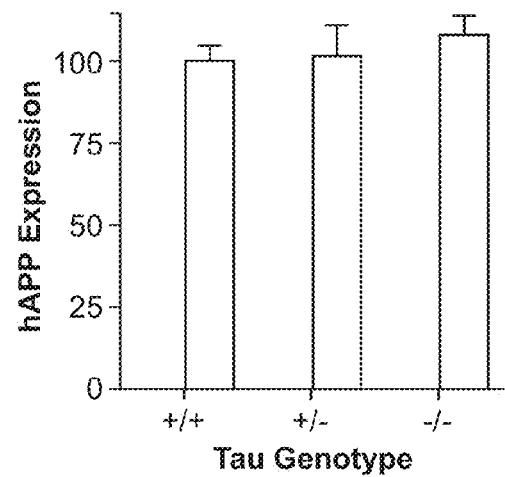
Figures 13A, 13B, 13C:
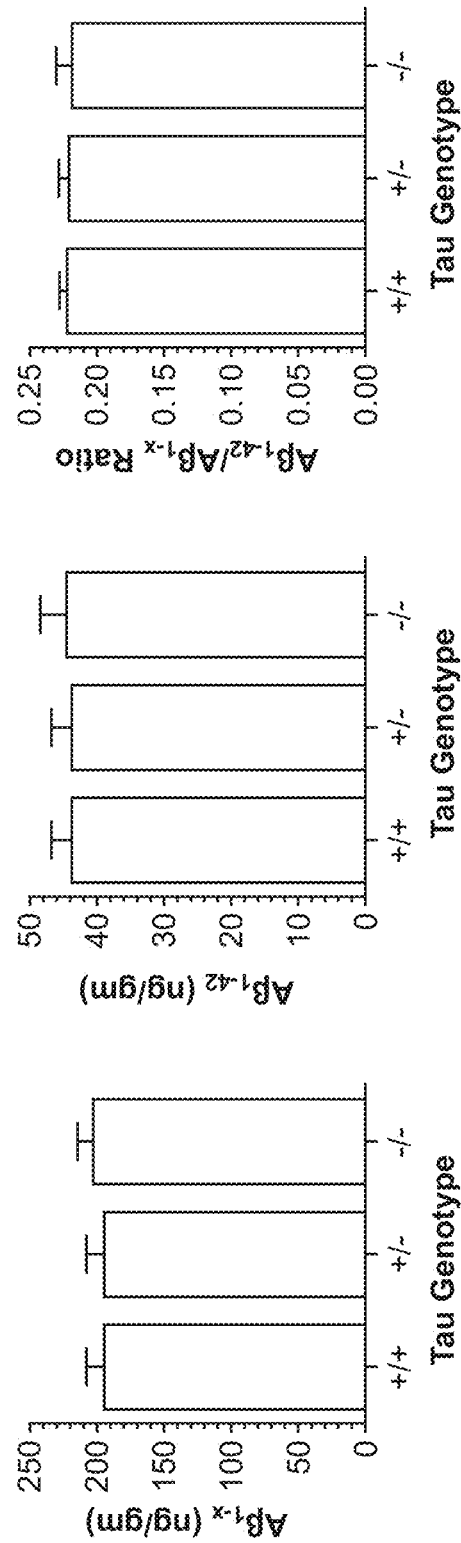
FIG. 13A-C depict results showing that tau reduction does not affect Aβ levels.

FIGS. 12A-12C. Tau and hAPP levels. (A) Immunoblots show tau and hAPP levels in hippocampal homogenates from each of the six genotypes in the study. Tubulin served as a loading control. (B) Quantification of tau levels determined by immunoblotting, expressed as percent of Tau$^{+/+}$ controls (n=4 per genotype). (C) Quantification of hAPP levels determined by immunoblotting, expressed as percent of hAPP/Tau$^{+/+}$ controls (n=4-8 per genotype).

FIGS. 13A-C. Tau reduction does not affect Aβ levels. Hippocampi from mice aged 2-3.5 months (before plaque formation) were homogenized in guanidine buffer and Aβ was measured by ELISA. Tau reduction did not affect Aβ$_{1-x}$ (A), Aβ$_{1-42}$ (B), or the ratio of Aβ$_{1-42}$ to Aβ$_{1-x}$ (C).

FIGS. 14A-H. Tau reduction does not affect plaque load in young mice. (A-C) Thioflavin-S staining of hippocampal amyloid plaques in hAPP mice. (D) Quantification of thioflavin-S staining, expressed as percent of hippocampal area covered by plaques (n=9-11 mice per genotype, age 4-7 months). (E-G) 3D6 immunostaining of hippocampal Aβ deposits in hAPP mice. (H) Quantification of Aβ deposits, expressed as percent of hippocampal area covered by plaques (n=11-13 mice per genotype, age 4-7 months).

FIGS. 15A and B. Tau reduction does not affect levels of Aβ*56. Aβ*56 was isolated from the cortex of 4-7-month-old mice. Left (FIG. 15A), representative immunoblot showing no effect of tau reduction. Right (FIG. 15B), quantification of n=6 mice per genotype.

Figure 16A:
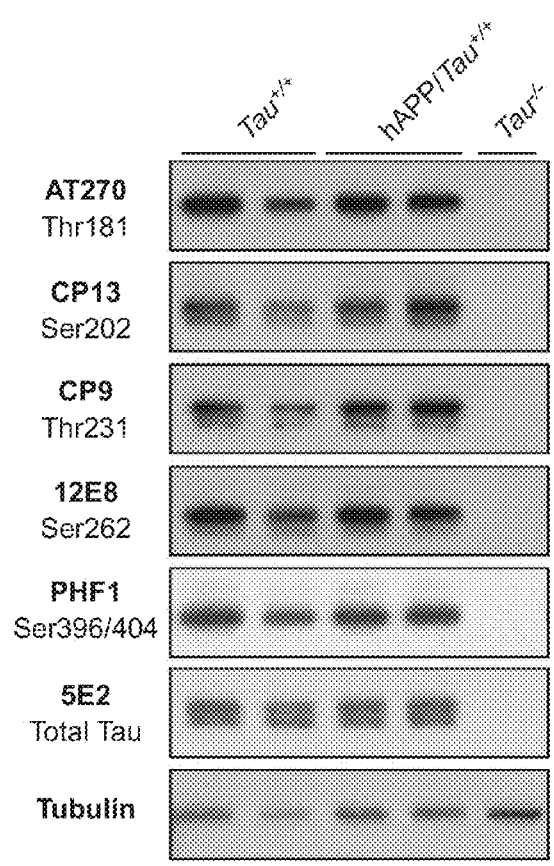
FIGS. 16A and 16B depict tau phosphorylation in hAPP/Tau$^{+/+}$ mice.
Figure 16B:
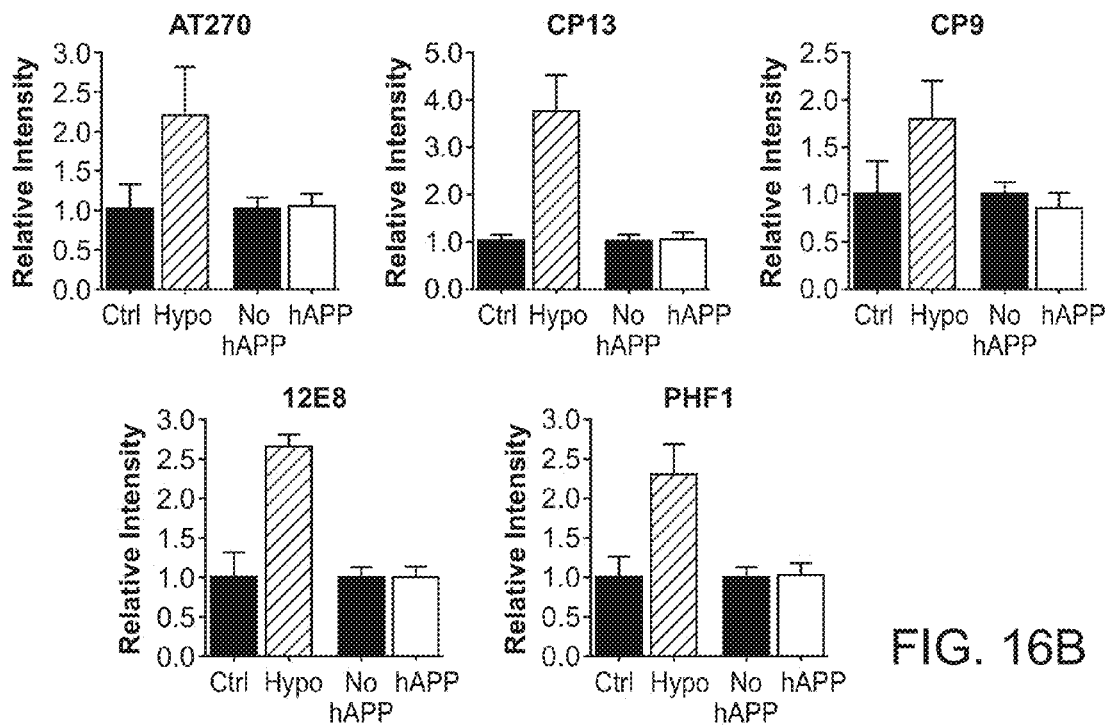

Abnormal forms of tau that might act as downstream effectors of Aβ in hAPP/Tau$^{+/+}$ mice were assessed. Major AD-related phosphorylation sites in human tau are conserved in murine tau, including those phosphorylated by proline-directed kinases, such as GSK-3β and cdk5, or by microtubule affinity-regulating kinase (MARK). Changes in murine tau phosphorylation at these sites are easily detected, for example after brief hypothermia (Planel et al. (2004) J Neurosci 24:2401-2411; FIGS. 16A and 16B). However, in hippocampal homogenates of 4-7-month-old hAPP/Tau$^{+/+}$ mice, changes in tau phosphorylation at proline-directed kinase sites, including Thr181, Ser202, Thr231, and Ser396/404, or at the primary site for MARK, Ser262, were not observed (FIGS. 16A and 16B). Generation of neurotoxic tau fragments has also been implicated as a mechanism of Aβ toxicity (Park and Ferreira (2005) J Neurosci 25:5365-5375). Tau-deficient primary neurons are resistant to Aβ-induced degeneration (Rapoport et al. (2002) Proc Natl Acad Sci USA 99:6364-6369; Liu et al. (2004) J Neurochem 88:554-563), apparently because Aβ toxicity in vitro involves production of a 17-kD tau fragment (Park and Ferreira (2005) supra). The presence of a 17-kD tau fragment in lysates of Aβ-treated primary neurons was confirmed; however, no abnormal tau proteolysis in hippocampal homogenates from hAPP mice was found (FIGS. 17A and 17B), suggesting that the neuroprotective effects of tau reduction in the two systems are mechanistically different.

FIGS. 16A and 16B. Tau phosphorylation in hAPP/Tau$^{+/+}$ mice. Hippocampal homogenates from 4-6-month-old Tau$^{+/+}$, hAPP/Tau$^{+/+}$, and Tau$^{-/-}$ mice were analyzed by immunoblotting with antibodies recognizing various tau phosphorylation sites, as indicated. Below, quantification of immunoblots (n=4 mice per group for untreated nontransgenic controls (Ctrl) and hypothermic (Hypo) nontransgenic mice, and n=12 mice per genotype for Tau$^{+/+}$ and hAPP/Tau$^{+/+}$).

Figure 17A:
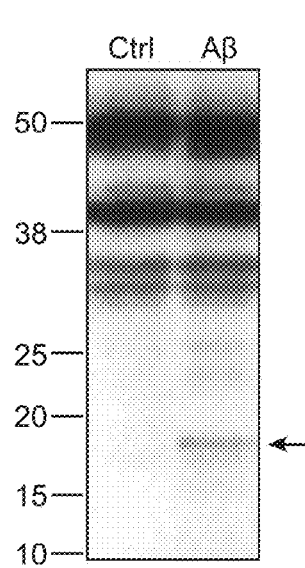
FIGS. 17A and 17B depict tau proteolysis.
Figure 17B:
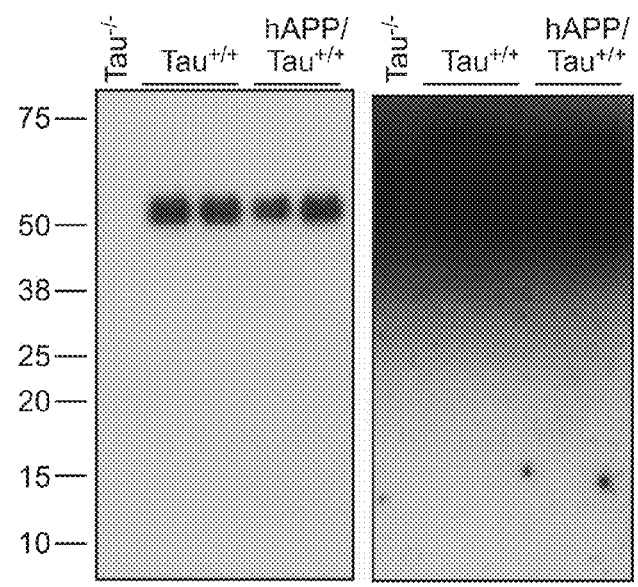

FIGS. 17A and 17B. Tau proteolysis. (A) Rat primary cortical neurons were treated for 48 h with 20 μM fibrillar Aβ and lysates were analyzed by immunoblotting with total tau antibody 5E2. The 17-kD tau fragment generated in response to Aβ treatment is indicated by the arrow. (B) Hippocampal homogenates from 4-6-month-old Tau$^{-/-}$, Tau$^{+/+}$, and hAPP/Tau$^{+/+}$ mice were analyzed by immunoblotting with total tau antibody 5E2. Overexposure of the same blot is depicted on the right, showing no detectable tau fragments.

The relative lack of modified tau also distinguishes the present model from transgenic lines overexpressing tau with mutations that cause frontotemporal dementia, but not AD, in humans (Lewis et al. (2001) Science 293:1487-1491; Oddo et al. (2004) Neuron 43:321-332; SantaCruz et al. (2005) Science 309:476-481). In the present study, reduction of endogenous, wildtype tau protected hAPP mice against Aβ-dependent cognitive impairments, and this did not involve the elimination of a large pool of tau with typical AD-associated modifications. These experiments do not rule out the possibility that other types of tau modification, or a small pool of modified tau in a restricted subcellular compartment or cellular population, may play a role downstream of Aβ.

Instead, these data support the idea that tau reduction protects hAPP mice by prevention of epileptiform activity. hAPP mice have abnormal electroencephalograms (EEGs), characterized by epileptiform spiking and nonconvulsive seizures (Palop et al. (2007) Neuron 55:697-711). Moreover, this aberrant activity results in secondary inhibitory remodelling, which attempts to suppress overactivation but is likely maladaptive in terms of hippocampal function; these inhibitory changes include calbindin depletion in dentate granule cells and aberrant expression of neuropeptide Y (NPY) in mossy fibers (Palop et al. (2007) supra). The severity of these changes correlates closely with the degree of behavioral impairment in hAPP mice (Palop et al. (2007) supra).

Figure 19:
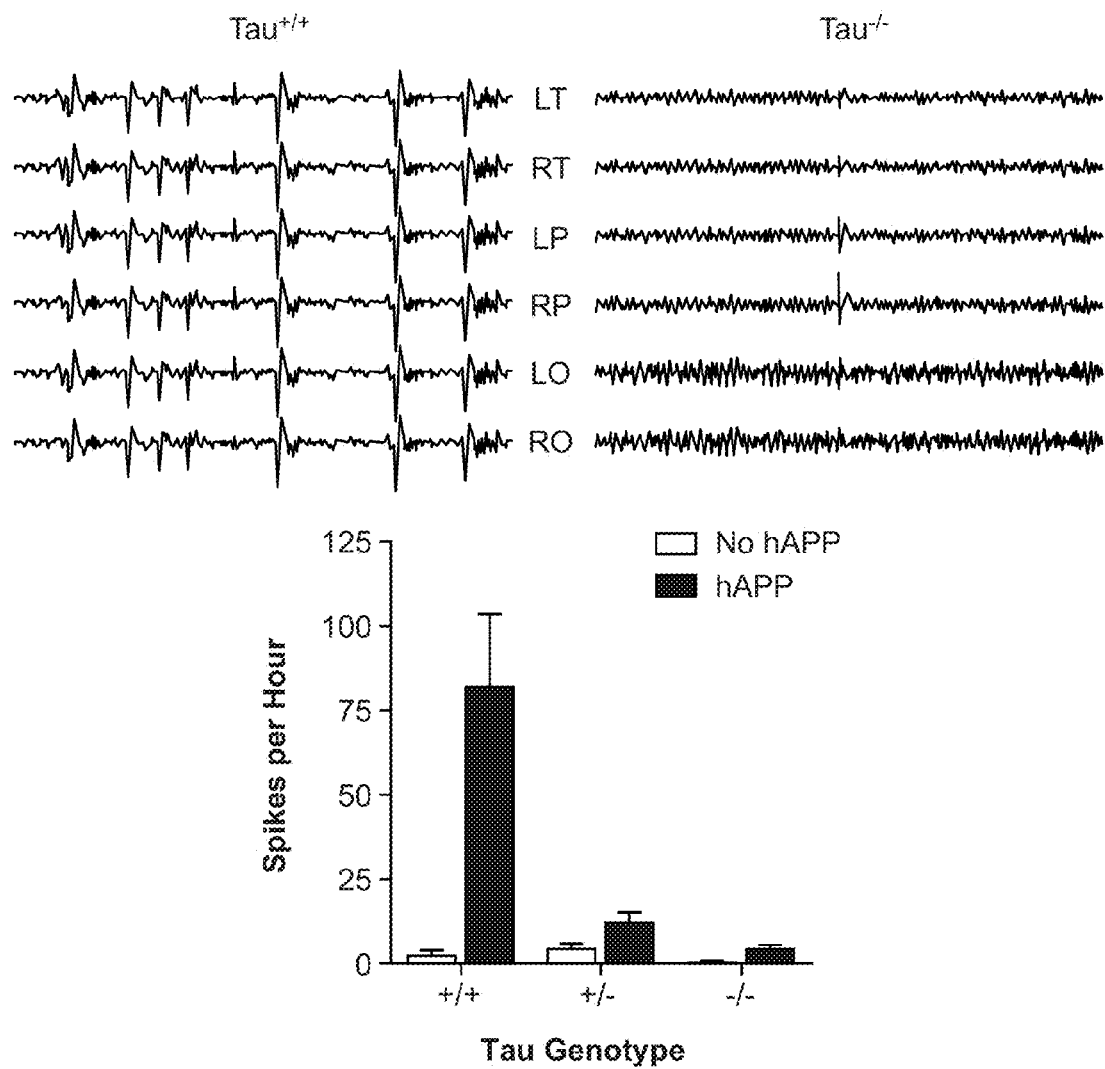
FIG. 19 depicts results showing that tau reduction blocks aberrant excitatory activity in hAPP mice.

Importantly, and consistent with the protective effect of tau reduction from pharmacologically induced seizures (FIG. 4), it was found that tau reduction also prevented the epileptiform abnormalities in hAPP mice (FIG. 19). Whereas hAPP/Tau$^{+/+}$ mice had extremely high counts of epileptiform spikes per hour, this was dramatically reduced in hAPP/Tau$^{+/-}$ mice, and normal in hAPP/Tau$^{-/-}$ mice (FIG. 19). Moreover, the compensatory inhibitory changes observed in hAPP/Tau$^{+/+}$ mice, including calbindin depletion and aberrant NPY expression, were greatly reduced in hAPP/Tau$^{+/-}$ mice and absent in hAPP/Tau$^{-/-}$ mice (FIG. 7).

FIG. 19. Tau reduction blocks aberrant excitatory activity in hAPP mice. EEG recordings from hAPP mice with normal tau levels (above left, Tau$^{+/+}$) show frequent epileptiform spikes. These abnormalities were not seen in hAPP mice without tau (above right, Tau$^{-/-}$). Quantification of epileptiform spike frequency (bottom) demonstrates that the epileptiform abnormalities seen in hAPP/Tau$^{+/+}$ mice were not seen in either hAPP/Tau$^{+/-}$ or hAPP/Tau$^{-/-}$ mice Whether the protective effects of tau reduction would be seen in another AD mouse model was assessed. Mice that express low levels of the hAPP transgene, and thus low levels of Aβ, do not have severe AD-like behavioral deficits. However, when these mice are crossed with mice expressing a transgene for the FYN tyrosine kinase, the resulting bigenic hAPP$_{low}$/FYN mice do have robust impairments. The hAPPlow and FYN mice were crossed onto a tau knockout background and repeated the cross, so that bigenic (hAPP$_{low}$/FYN) mice could be compared with normal tau levels (Tau$^{+/+}$) with bigenic mice lacking tau (Tau$^{-/-}$). It was found that tau reduction blocked behavioral abnormalities in these mice, including water maze learning and memory deficits and abnormal exploratory activity (FIG. 8) and early mortality (FIG. 9). The hAPP$_{low}$/FYN bigenic mice display the same types of epileptiform abnormalities and compensatory inhibitory remodelling (calbindin depletion and aberrant NPY expression) that are seen in the higher expressing hAPP mice (Palop et al. (2007) supra). It was also found that the inhibitory changes seen in bigenic mice with normal tau levels were blocked by tau reduction (FIG. 18), providing further evidence that tau reduction protects this line by similar mechanisms to those seen in the other hAPP mice.

Figure 18:
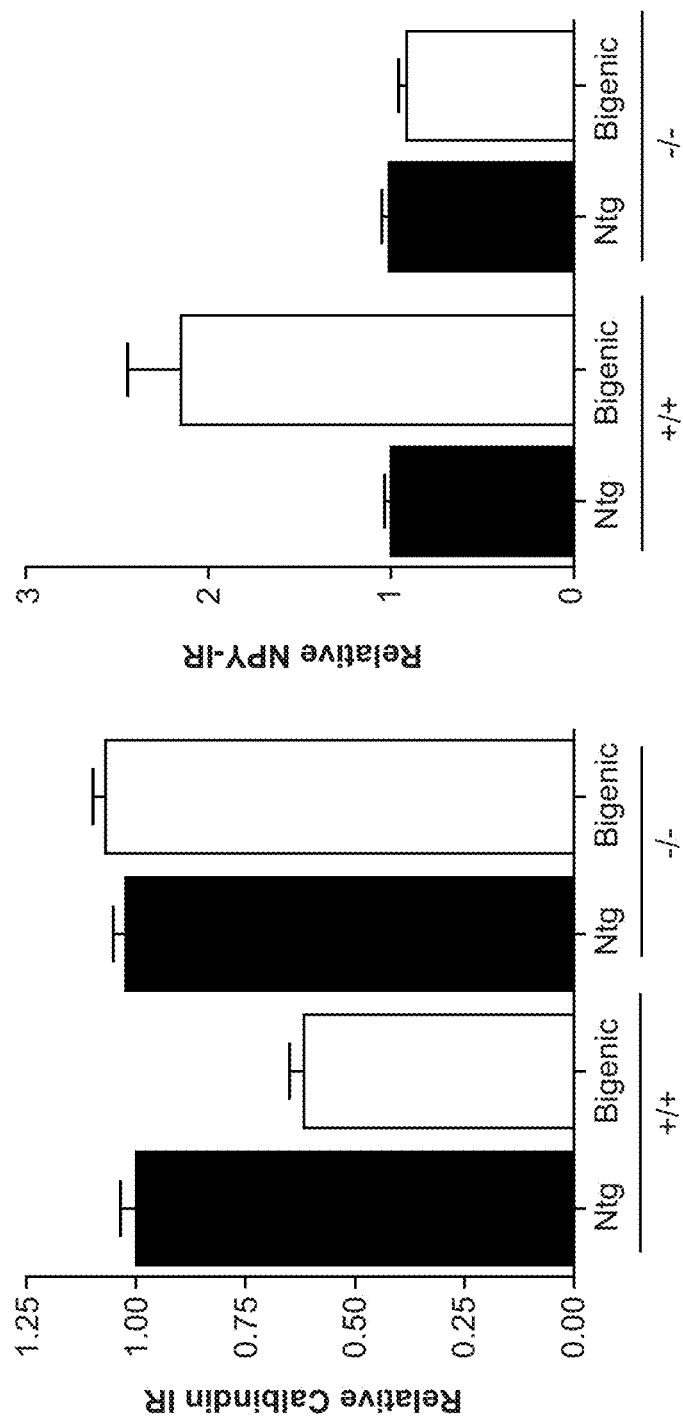
FIG. 18 depicts results showing that tau reduction blocks inhibitory remodeling in hAPP-J9/FYN bigenic mice.

FIG. 18. Tau reduction blocks inhibitory remodelling in hAPP-J9/FYN bigenic mice. Calbindin and NPY were immunohistochemically stained in sections from nontransgenic and bigenic mice expressing either normal tau levels (+/+) or on a tau-deficient background (−/−). Inhibitory changes seen in bigenic mice with normal tau levels (calbindin depletion and aberrant increases in NPY-positive sprouting) were absent in bigenic mice without tau.

Figure 20:
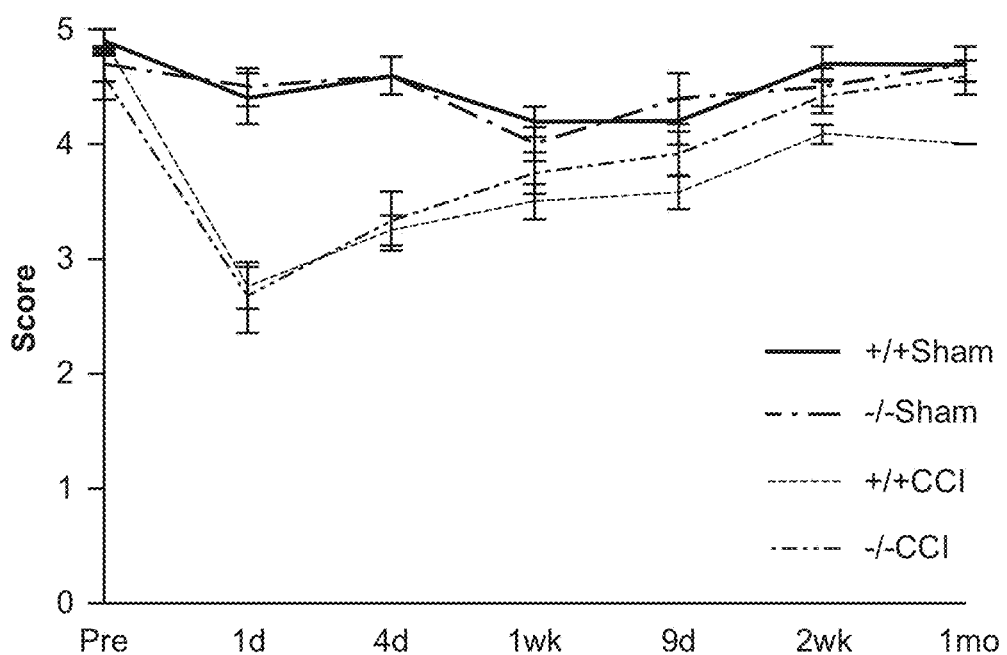
FIG. 20 depicts results showing that tau reduction improves recovery after head injury.
Figure 21:
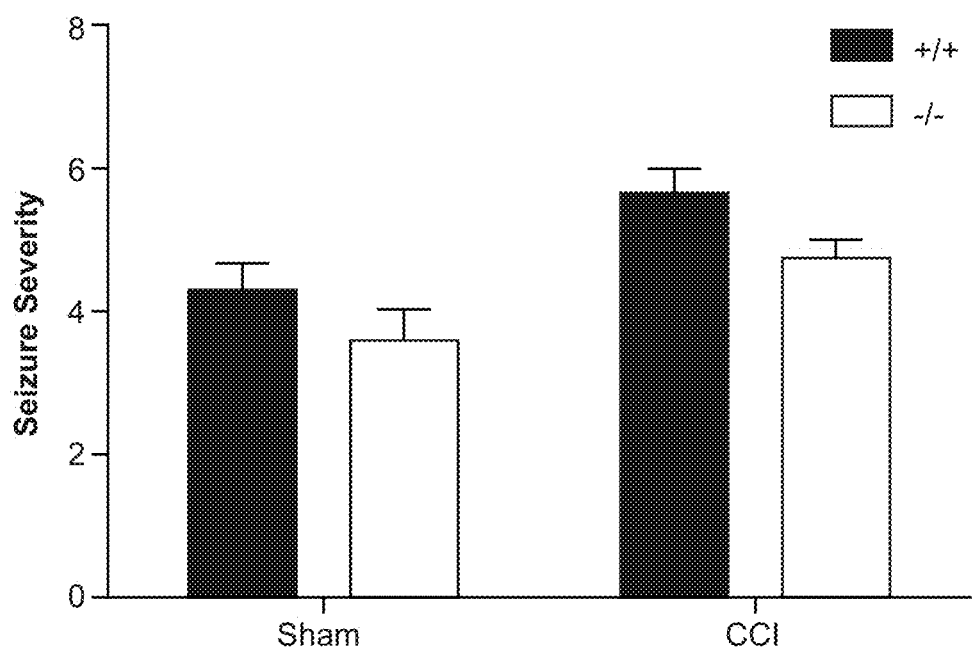
FIG. 21 depicts results showing that tau reduction ameliorates seizures after head injury.

The studies of the protective effects of tau reduction were extended to a model of traumatic brain injury. Head injuries can also induce both epileptiform activity and cognitive impairments. Whether Tau$^{-/-}$ mice might be protected relative to Tau$^{+/+}$ mice was tested. Male mice of each genotype (n=12) were subjected to the controlled cortical impact (CCI) model of traumatic brain injury, with control groups from both genotypes undergoing sham surgery. CCI produced initial impairments on the wire hang test of motor function that were equivalent in Tau$^{+/+}$ and Tau$^{-/-}$ mice (FIG. 20). However, over time, recovery was improved in the Tau$^{-/-}$ mice, which returned to normal performance at one month post-injury while Tau$^{+/+}$ mice had residual deficits (p<0.005). Epileptiform activity may contribute to the pathophysiology in this model, as CCI increased susceptibility to seizures induced by PTZ (FIG. 21). Again, it was found a protective effect of tau reduction; seizure severity in Tau$^{-/-}$ mice undergoing CCI was not significantly different from sham-operated Tau$^{+/+}$ mice (FIG. 21).

FIG. 20. Tau reduction improves recovery after head injury. Both Tau$^{+/+}$ and Tau$^{-/-}$ mice underwent either head injury by controlled cortical impact (CCI) or a sham operation with no head injury. The time course of resulting deficits was assessed by a wire hang test, where "5" was normal performance and "0" was severe impairment. CCI produced identical initial impairment regardless of tau genotype. However, Tau$^{-/-}$ mice recovered better; by one month after CCI, Tau$^{-/-}$ mice had returned to normal while impairment remained in the Tau$^{+/+}$ mice. Data were analyzed by a repeated measures general linear model with age, tau genotype and treatment as factors; Tau×treatment interaction, p<0.001.

FIG. 21. Tau reduction ameliorates seizures after head injury. Both Tau$^{+/+}$ and Tau$^{-/-}$ mice underwent either head injury by controlled cortical impact (CCI) or a sham operation with no head injury. One month after injury, seizures susceptibility was assessed by injection of 40 mg/kg pentylenetetrazole (PTZ). Severity of the resulting seizures was scored by video analysis. Tau reduction reduced seizure severity in both sham and CCI groups (p<0.02), such that seizures in Tau$^{-/-}$ mice that had undergone CCI were not significantly worse than seizures in sham-treated group.

REFERENCES

1. R. Tanzi, L. Bertram, Cell 120, 545 (2005).
2. J. Lewis et al., Science 293, 1487 (2001).
3. M. Rapoport, H. N. Dawson, L. I. Binder, M. P. Vitek, A. Ferreira, Proc. Natl. Acad. Sci. USA 99, 6364 (2002).
4. S. Oddo, L. Billings, J. P. Kesslak, D. H. Cribbs, F. M. LaFerla, Neuron 43, 321 (2004).
5. C. X. Gong, F. Liu, I. Grundke-Iqbal, K. Iqbal, J Neural Transm 112, 813 (2005).
6. K. Iqbal et al., Biochim Biophys Acta 1739, 198 (2005).
7. W. H. Stoothoff, G. V. Johnson, Biochim. Biophys. Acta 1739, 280 (2005).
8. I. Khlistunova et al., J Biol Chem 281, 1205 (2006).
9. C. A. Dickey et al., FASEB J. 20, 753 (2006).
10. A. J. Myers et al., Hum. Mol. Genet. 14, 2399 (2005).
11. L. Mucke et al., J. Neurosci. 20, 4050 (2000).
12. H. N. Dawson et al., J. Cell Sci. 114, 1179 (2001).
13. J. J. Palop et al., Proc. Natl. Acad. Sci. USA 100, 9572 (2003).
14. D. T. Kobayashi, K. S. Chen, Genes Brain and Behay. 4, 173 (2005).
15. O. Steward, J. Loesche, W. C. Horton, Brain Res. Bull. 2, 41 (1977).
16. K. K. Hsiao et al., Neuron 15, 1203 (1995).
17. J. Chin et al., J. Neurosci. 24, 4692 (2004).
18. S. Lesné et al., Nature 440, 352 (2006).

19. E. Planel et al., J. Neurosci. 24, 2401 (2004).
20. S. Y. Park, A. Ferreira, J. Neurosci. 25, 5365 (2005).
21. T. Liu et al., J. Neurochem. 88, 554 (2004).
22. K. SantaCruz et al., Science 309, 476 (2005).
23. R. B. Knowles et al., Proc. Natl. Acad. Sci. USA 96, 5274 (1999).
24. J. W. Geddes et al., Science 230, 1179 (1985).
25. M. P. Mattson, Nature 430, 631 (2004).
26. J. W. Olney, D. F. Wozniak, N. B. Farber, Arch. Neurol. 54, 1234 (1997).
27. J. C. Amatniek et al., Epilepsia 47, 867 (2006).
28. R. A. Del Vecchio, L. H. Gold, S. J. Novick, G. Wong, L. A. Hyde, Neurosci. Lett. 367, 164 (2004).
29. J. J. Palop, J. Chin, L. Mucke, Nature 443, 768 (2006).
30. J. R. Lupski, Nat. Genet. 38, 974 (2006).
31. F. Holsboer, Curr Opin Investig Drugs 4, 46 (2003).

Chin, J., Palop J. J., Yu G.-Q., Kojima N., Masliah E., Mucke L. 2004. Fyn kinase modulates synaptotoxicity, but not aberrant sprouting, in human amyloid precursor protein transgenic mice. J. Neurosci. 24, 4692-4697.

Chin, J., Palop J. J., Puolivali J., Massaro C., Bien-Ly N., Gerstein H., Scearce-Levie K., Masliah E., Mucke L. 2005. Fyn kinase induces synaptic and cognitive impairments in a transgenic mouse model of Alzheimer's disease. J. Neurosci. 25, 9694-9703.

Nägerl, U. V., Mody I., Jeub M., Lie A. A., Elger C. E., Beck H. 2000. Surviving granule cells of the sclerotic human hippocampus have reduced $Ca^{2+}$ influx because of a loss of calbindin-$D_{28K}$ in temporal lobe epilepsy. J. Neurosci. 20, 1831-1836.

Palop, J. J., Chin J., Mucke L. 2006. A network dysfunction perspective on neurodegenerative diseases. Nature 443, 768-773.

Palop, J. J., Jones B., Kekonius L., Chin J., Yu G.-Q., Raber J., Masliah E., Mucke L. 2003. Neuronal depletion of calcium-dependent proteins in the dentate gyrus is tightly linked to Alzheimer's disease-related cognitive deficits. Proc. Natl. Acad. Sci. USA 100, 9572-9577.

Vezzani, A., Sperk G., Colmers W. F. 1999. Neuropeptide Y: Emerging evidence for a functional role in seizure modulation. Trends Neurosci 22, 25-30.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical composition comprising:

a) a modified nucleic acid agent that specifically reduces the level of a tau gene product in a cell, and that targets a region of a tau gene selected from:

(SEQ ID NO: 13)
(i) 5'-gat cttagcaacg tccagtccaa gtgtggctca aaggataata tcaaacacgt cccgggaggc ggcagtgtgc aaatagtcta caaaccagtt-3';

(SEQ ID NO: 14)
(ii) 5'-gacctgagca aggtgacctc caagtgtggc tcattaggca acatccatca taaaccagga ggtggccagg tggaagtaaa atctgagaag ctt-3';

(SEQ ID NO: 15)
(iii) 5'-gacttca aggacagagt ccagtcgaag attgggtccc tggacaatat cacccacgtc cctggcggag gaaataaaaa gattgaaacc cacaagctg-3';

(SEQ ID NO: 16)
(iv) 5'-aagtcgccgt cttccgccaa gagccgcctg-3';

(SEQ ID NO: 17)
(v) 5'-gccaagacag accacggggc gggagatcgtg-3';

and b) a pharmaceutically acceptable excipient.

2. The composition of claim 1, wherein the pharmaceutically acceptable excipient comprises an agent that provides for crossing the blood-brain barrier.

3. The composition of claim 1, wherein the tau gene product is encoded by a wild-type tau allele.

4. The composition of claim 1, wherein the nucleic acid agent comprises at least one modification that increases stability and/or biological activity of the agent.

5. The composition of claim 1, wherein the composition further comprises a lipid.

6. The composition of claim 1, wherein the composition further comprises a biodegradable polymer.

7. The composition of claim 1, wherein the nucleic acid agent is encapsulated in a liposome.

8. The composition of claim 1, wherein the nucleic acid agent is formulated for crossing the blood-brain barrier.

9. The composition of claim 1, wherein the nucleic acid agent is an antisense nucleic acid.

10. The composition of claim 1, wherein the nucleic acid agent comprises a backbone modification.

11. The composition of claim 1, wherein the composition comprises polyethyleneimine, polyethyleneimine-polyethyleneglycol-N-acetylgalactosamine, or polyethyleneimine-polyethyleneglycol-tri-N-acetylgalactosamine.

12. The composition of claim 1, wherein the nucleic acid agent is complexed with a membrane disruptive agent.

13. The composition of claim 1, wherein the modified nucleic acid comprises a modified sugar.

14. The composition of claim 1, wherein the modified nucleic acid comprises at least one modified base.

15. The composition of claim 1, wherein the nucleic acid agent is encoded by a recombinant expression vector.

16. The composition of claim 15, wherein the nucleic acid agent is expressed by an adeno-associated virus or a retrovirus.

* * * * *

SEQUENCE LISTING

<160> NUMBER OF SEQ ID NOS: 24

<210> SEQ ID NO 1
<211> LENGTH: 758
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

```
Leu Gly Asp Leu His Gln Glu Gly Pro Pro Leu Lys Gly Ala Gly Gly
            195                 200                 205

Lys Glu Arg Pro Gly Ser Lys Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
```

```
                    610              615                 620
Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
                675                 680                 685

Glu Thr His Lys Leu Thr Phe Arg Glu Asn Ala Lys Ala Lys Thr Asp
            690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                    725                 730                 735

Val Asp Ser Pro Gln Leu Ala Thr Leu Ala Asp Glu Val Ser Ala Ser
                740                 745                 750

Leu Ala Lys Gln Gly Leu
        755

<210> SEQ ID NO 2
<211> LENGTH: 2277
<212> TYPE: DNA
<213> ORGANISM: Homo sapiens

<400> SEQUENCE: 2
atggctgagc ccgccagga gttcgaagtg atggaagatc acgctgggac gtacgggttg      60
ggggacagga agatcagggg gggctacacc atgcaccaag accaagaggg tgacacggac     120
gctggcctga agaatctccc cctgcagacc cccactgagg acggatctga ggaaccgggc     180
tctgaaacct ctgatgctaa gagcactcca acagcggaag atgtgacagc acccttagtg     240
gatgagggag ctcccggcaa gcaggctgcc gcgcagcccc acacggagat cccagaagga     300
accacagctg aagaagcagg cattggagac cccccagcc tggaagacga agctgctggt     360
cacgtgaccc aagagcctga aagtggtaag gtggtccagg aaggcttcct ccgagagcca     420 ggcccccag tctgagccca ccagctcatg tccggcatgc ctgggctcc cctcctgcct      480 gagggcccca gagaggccac acgccaacct tcggggacag gacctgagga cacagagggc     540
ggccgccacg cccctgagct gctcaagcac cagcttctag agacctgca ccaggagggg      600 ccgccgctga gggggcagg gggcaaagag aggccgggga gcaaggagga ggtggatgaa      660
gaccgcgacg tcgatgagtc ctcccccaa gactcccctc cctccaaggc ctccccagcc      720
caagatgggc ggcctcccca gacagccgcc agagaagcca ccagcatccc aggcttccca     780
gcggagggtg ccatcccct ccctgtggat tcctctcca aagtttccac agagatccca      840
gcctcagagc ccgacgggcc cagtgtaggg cgggccaaag gcaggatgc cccctggag      900 ttcacgtttc acgtggaaat cacacccaac gtgcagaagg agcaggcgca ctcggaggag     960
catttgggaa gggctgcatt tccagggc cctggagagg ggccagaggc ccggggcccc      1020
tctttgggag aggacacaaa agaggctgac cttccagagc cctctgaaaa gcagcctgct     1080
gctgctccgc gggggaagcc cgtcagccgg gtccctcaac tcaaagctcg catggtcagt     1140
aaaagcaaag acgggactgg aagcgatgac aaaaaagcca agacatccac acgttcctct     1200
gctaaaacct tgaaaaatag gccttgcctt agccccaaac tccccactcc tggtagctca     1260
```

-continued

```
gaccctctga tccaaccctc cagccctgct gtgtgcccag agccaccttc ctctcctaaa   1320
cacgtctctt ctgtcacttc ccgaactggc agttctggag caaaggagat gaaactcaag   1380
ggggctgatg gtaaaacgaa gatcgccaca ccgcggggag cagcccctcc aggccagaag   1440
ggccaggcca acgccaccag gattccagca aaaaccccgc ccgctcccaa gacaccaccc   1500
agctctggtg aacctccaaa atcaggggat cgcagcggct acagcagccc cggctcccca   1560
ggcactcccg gcagccgctc ccgcaccccg tccttccaa ccccacccac ccggagccc   1620
aagaaggtgg cagtggtccg tactccaccc aagtcgccgt cttccgccaa gagccgcctg   1680
cagacagccc ccgtgcccat gccagacctg aagaatgtca agtccaagat cggctccact   1740
gagaacctga agcaccagcc gggaggcggg aaggtgcaga taattaataa gaagctggat   1800
cttagcaacg tccagtccaa gtgtggctca aaggataata tcaaacacgt cccgggaggc   1860
ggcagtgtgc aaatagtcta caaccagtt gacctgagca aggtgacctc caagtgtggc   1920
tcattaggca acatccatca taaaccagga ggtggccagg tggaagtaaa atctgagaag   1980
cttgacttca aggacagagt ccagtcgaag attgggtccc tggacaatat cacccacgtc   2040
cctggcggag gaaataaaaa gattgaaacc cacaagctga ccttccgcga gaacgccaaa   2100
gccaagacag accacggggc ggagatcgtg tacaagtcgc cagtggtgtc tggggacacg   2160
tctccacggc atctcagcaa tgtctcctcc accggcagca tcgacatggt agactcgccc   2220
cagctcgcca cgctagctga cgaggtgtct gcctccctgg ccaagcaggg tttgtga      2277
```

<210> SEQ ID NO 3
<211> LENGTH: 441
<212> TYPE: PRT
<213> ORGANISM: Homo sapiens

<400> SEQUENCE: 3

```
Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
```

```
                195                 200                 205
Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 4
<211> LENGTH: 1326
<212> TYPE: DNA
<213> ORGANISM: Homo sapiens

<400> SEQUENCE: 4
atggctgagc cccgccagga gttcgaagtg atggaagatc acgctgggac gtacgggttg      60
ggggacagga aagatcaggg gggctacacc atgcaccaag accaagaggg tgacacggac     120
gctggcctga agaatctccc ctgcagaccc ccactgagga cggatctga ggaaccgggc      180 tctgaaacct ctgatgctaa gagcactcca cagcggaaa atgtgacagc acccttagtg      240
gatgagggag ctcccggcaa gcaggctgcc gcgcagcccc acacggagat cccagaagga     300
accacagctg aagaagcagg cattggagac cccccagcc tggaagacga agctgctggt      360
cacgtgaccc aagctcgcat ggtcagtaaa agcaaagacg ggactggaag cgatgacaaa     420
aaagccaagg gggctgatgg taaaacgaag atcgccacac gcggggagc agcccctcca      480 ggccagaagg gccaggccaa cgccaccagg attccagcaa aaaccccgcc cgctccaaag     540
acaccaccca gctctggtga acctccaaaa tcaggggatc gcagcggcta cagcagcccc     600
ggctccccag gcactcccgg cagccgctcc cgcaccccgt cccttccaac cccacccacc     660
cgggagccca gaaggtggc agtggtccgt actccaccca gtcgccgtc ttccgccaag      720
```

| | | |
|---|---|---|
| agccgcctgc agacagcccc cgtgcccatg ccagacctga gaatgtcaa gtccaagatc | 780 | |
| ggctccactg agaacctgaa gcaccagccg ggaggcggga aggtgcagat aattaataag | 840 | |
| aagctggatc ttagcaacgt ccagtccaag tgtggctcaa aggataatat caaacacgtc | 900 | |
| ccggaggcg gcagtgtgca aatagtctac aaaccagttg acctgagcaa ggtgacctcc | 960 | |
| aagtgtggct cattaggcaa catccatcat aaaccaggag gtggccaggt ggaagtaaaa | 1020 | |
| tctgagaagc ttgacttcaa ggacagagtc cagtcgaaga ttgggtccct ggacaatatc | 1080 | |
| acccacgtcc ctggcggagg aaataaaaag attgaaaccc acaagctgac cttccgcgag | 1140 | |
| aacgccaaag ccaagacaga ccacggggcg gagatcgtgt acaagtcgcc agtggtgtct | 1200 | |
| ggggacacgt ctccacggca tctcagcaat gtctcctcca ccggcagcat cgacatggta | 1260 | |
| gactcgcccc agctcgccac gctagctgac gaggtgtctg cctccctggc caagcagggt | 1320 | |
| ttgtga | 1326 | |

<210> SEQ ID NO 5
<211> LENGTH: 383
<212> TYPE: PRT
<213> ORGANISM: Homo sapiens

<400> SEQUENCE: 5

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Ala Glu Glu Ala
         35                  40                  45

Gly Ile Gly Asp Thr Pro Ser Leu Glu Asp Glu Ala Ala Gly His Val
     50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
```

```
                  260                 265                 270
Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 6
<211> LENGTH: 1152
<212> TYPE: DNA
<213> ORGANISM: Homo sapiens

<400> SEQUENCE: 6
atggctgagc cccgccagga gttcgaagtg atggaagatc acgctgggac gtacggttg     60 ggggacagga aagatcaggg gggctacacc atgcaccaag accaagaggg tgacacggac   120
gctggcctga agctgaaga agcaggcatt ggagacaccc ccagcctgga agacgaagct    180
gctggtcacg tgacccaagc tcgcatggtc agtaaaagca agacgggac tggaagcgat    240 gacaaaaaag ccaaggggc tgatggtaaa acgaagatcg ccacaccgcg ggagcagcc     300 cctccaggcc agaagggcca ggccaacgcc accaggattc agcaaaaac cccgcccgct    360 ccaaagacac cacccagctc tggtgaacct ccaaaatcag gggatcgcag cggctacagc   420
agccccggct ccccaggcac tcccggcagc cgctcccgca ccccgtccct tccaacccca   480 cccaccggg agcccaagaa ggtggcagtg gtccgtactc cacccaagtc gccgtcttcc    540
gccaagagcc gcctgcagac agcccccgtg cccatgccag acctgaagaa tgtcaagtcc   600
aagatcggct ccactgagaa cctgaagcac cagccgggag cgggaaggt gcagataatt    660 aataagaagc tggatcttag caacgtccag tccaagtgtg gctcaaagga taatatcaaa   720
cacgtcccgg gaggcggcag tgtgcaaata gtctacaaac cagttgacct gagcaaggtg   780
acctccaagt gtggctcatt aggcaacatc atcataaac caggaggtgg ccaggtggaa    840
gtaaaatctg agaagcttga cttcaaggac agagtccagt cgaagattgg gtccctggac   900 aatatcacc acgtccctgg cggaggaaat aaaaagattg aaacccacaa gctgaccttc   960
cgcgagaacg ccaaagccaa gacagaccac ggggcggaga tcgtgtacaa gtcgccagtg  1020
gtgtctgggg acacgtctcc acggcatctc agcaatgtct cctccaccgg cagcatcgac  1080
atggtagact cgccccagct cgccacgcta gctgacgagg tgtctgcctc cctggccaag  1140
cagggtttgt ga                                                      1152

<210> SEQ ID NO 7
<211> LENGTH: 352
<212> TYPE: PRT
<213> ORGANISM: Homo sapiens

<400> SEQUENCE: 7
```

```
Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Ala Glu Glu Ala
        35                  40                  45
Gly Ile Gly Asp Thr Pro Ser Leu Glu Asp Glu Ala Ala Gly His Val
    50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Pro Ser Ser Gly
        115                 120                 125
Glu Pro Pro Lys Ser Gly Asp Arg Ser Gly Tyr Ser Ser Pro Gly Ser
    130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
        195                 200                 205
Lys His Gln Pro Gly Gly Gly Lys Val Gln Ile Val Tyr Lys Pro Val
    210                 215                 220
Asp Leu Ser Lys Val Thr Ser Lys Cys Gly Ser Leu Gly Asn Ile His
225                 230                 235                 240
His Lys Pro Gly Gly Gly Gln Val Glu Val Lys Ser Glu Lys Leu Asp
                245                 250                 255
Phe Lys Asp Arg Val Gln Ser Lys Ile Gly Ser Leu Asp Asn Ile Thr
            260                 265                 270
His Val Pro Gly Gly Gly Asn Lys Lys Ile Glu Thr His Lys Leu Thr
        275                 280                 285
Phe Arg Glu Asn Ala Lys Ala Lys Thr Asp His Gly Ala Glu Ile Val
    290                 295                 300
Tyr Lys Ser Pro Val Val Ser Gly Asp Thr Ser Pro Arg His Leu Ser
305                 310                 315                 320
Asn Val Ser Ser Thr Gly Ser Ile Asp Met Val Asp Ser Pro Gln Leu
                325                 330                 335
Ala Thr Leu Ala Asp Glu Val Ser Ala Ser Leu Ala Lys Gln Gly Leu
            340                 345                 350

<210> SEQ ID NO 8
<211> LENGTH: 1059
<212> TYPE: DNA
<213> ORGANISM: Homo sapiens

<400> SEQUENCE: 8
atggctgagc ccgccagga gttcgaagtg atggaagatc acgctgggac gtacgggttg      60
ggggacagga aagatcaggg gggctacacc atgcaccaag accaagaggg tgacacggac     120
gctggcctga agctgaaga agcaggcatt ggagacaccc ccagcctgga agacgaagct      180
```

```
gctggtcacg tgacccaagc tcgcatggtc agtaaaagca aagacgggac tggaagcgat      240
gacaaaaaag ccaaggggc tgatggtaaa acgaagatcg ccacaccgcg gggagcagcc       300
cctccaggcc agaagggcca ggccaacgcc accaggattc agcaaaaac cccgcccgct       360 ccaaagacac cacccagctc tggtgaacct ccaaaatcag gggatcgcag cggctacagc      420
agccccggct ccccaggcac tcccggcagc cgctcccgca ccccgtccct tccaaccca      480 cccacccggg agcccaagaa ggtggcagtg gtccgtactc cacccaagtc gccgtcttcc     540
gccaagagcc gcctgcagac agccccgtg cccatgccag acctgaagaa tgtcaagtcc      600
aagatcggct ccactgagaa cctgaagcac agccgggag gcgggaaggt gcaaatagtc      660
tacaaaccag ttgacctgag caaggtgacc tccaagtgtg gctcattagg caacatccat    720
cataaaccag gaggtggcca ggtggaagta aaatctgaga agcttgactt caaggacaga    780
gtccagtcga agattgggtc cctggacaat atcacccacg tccctggcgg aggaaataaa    840
aagattgaaa cccacaagct gaccttccgc gagaacgcca agccaagac agaccacggg    900 gcggagatcg tgtacaagtc gccagtggtg tctggggaca cgtctccacg gcatctcagc   960
aatgtctcct ccaccggcag catcgacatg gtagactcgc cccagctcgc cacgctagct   1020
gacgaggtgt ctgcctccct ggccaagcag ggtttgtga                            1059
```

```
<210> SEQ ID NO 9
<211> LENGTH: 8
<212> TYPE: PRT
<213> ORGANISM: Artificial Sequence
<220> FEATURE:
<223> OTHER INFORMATION: synthetic epitope tag

<400> SEQUENCE: 9

Asp Tyr Lys Asp Asp Asp Asp Lys
 1               5

<210> SEQ ID NO 10
<211> LENGTH: 21
<212> TYPE: DNA
<213> ORGANISM: Homo sapiens

<400> SEQUENCE: 10
aatcacaccc aacgtgcaga a                                                21

<210> SEQ ID NO 11
<211> LENGTH: 21
<212> TYPE: DNA
<213> ORGANISM: Homo sapiens

<400> SEQUENCE: 11
aactggcagt tctggagcaa a                                                21

<210> SEQ ID NO 12
<211> LENGTH: 93
<212> TYPE: DNA
<213> ORGANISM: Homo sapiens

<400> SEQUENCE: 12
gacctgaaga atgtcaagtc caagatcggc tccactgaga acctgaagca ccagccggga     60
ggcgggaagg tgcagataat taataagaag ctg                                   93

<210> SEQ ID NO 13
<211> LENGTH: 93
```

<212> TYPE: DNA
<213> ORGANISM: Homo sapiens

<400> SEQUENCE: 13
gatcttagca acgtccagtc caagtgtggc tcaaaggata atatcaaaca cgtcccggga    60
ggcggcagtg tgcaaatagt ctacaaacca gtt                                93

<210> SEQ ID NO 14
<211> LENGTH: 93
<212> TYPE: DNA
<213> ORGANISM: Homo sapiens

<400> SEQUENCE: 14
gacctgagca aggtgacctc caagtgtggc tcattaggca acatccatca taaaccagga    60
ggtggccagg tggaagtaaa atctgagaag ctt                                93

<210> SEQ ID NO 15
<211> LENGTH: 96
<212> TYPE: DNA
<213> ORGANISM: Homo sapiens

<400> SEQUENCE: 15
gacttcaagg acagagtcca gtcgaagatt gggtccctgg acaatatcac ccacgtccct    60
ggcggaggaa ataaaaagat tgaaacccac aagctg                             96

<210> SEQ ID NO 16
<211> LENGTH: 30
<212> TYPE: DNA
<213> ORGANISM: Homo sapiens

<400> SEQUENCE: 16
aagtcgccgt cttccgccaa gagccgcctg                                    30

<210> SEQ ID NO 17
<211> LENGTH: 30
<212> TYPE: DNA
<213> ORGANISM: Homo sapiens

<400> SEQUENCE: 17
gccaagacag accacggggc ggagatcgtg                                    30

<210> SEQ ID NO 18
<211> LENGTH: 22
<212> TYPE: DNA
<213> ORGANISM: Artificial Sequence
<220> FEATURE:
<223> OTHER INFORMATION: synthetic DNA

<400> SEQUENCE: 18
tcgaagtgat ggaagatcac gc                                            22

<210> SEQ ID NO 19
<211> LENGTH: 22
<212> TYPE: DNA
<213> ORGANISM: Artificial Sequence
<220> FEATURE:
<223> OTHER INFORMATION: synthetic DNA

<400> SEQUENCE: 19
cagccgggag tcgggaaggt gc                                            22

<210> SEQ ID NO 20

-continued

```
<211> LENGTH: 24
<212> TYPE: DNA
<213> ORGANISM: Artificial Sequence
<220> FEATURE:
<223> OTHER INFORMATION: synthetic DNA

<400> SEQUENCE: 20
acgtcctcgg cggcggcagt gtgc                                              24

<210> SEQ ID NO 21
<211> LENGTH: 21
<212> TYPE: DNA
<213> ORGANISM: Artificial Sequence
<220> FEATURE:
<223> OTHER INFORMATION: synthetic DNA

<400> SEQUENCE: 21
acgtctccat ggcatctcag c                                                 21

<210> SEQ ID NO 22
<211> LENGTH: 22
<212> TYPE: DNA
<213> ORGANISM: Artificial Sequence
<220> FEATURE:
<223> OTHER INFORMATION: synthetic DNA

<400> SEQUENCE: 22
gtggccagat ggaagtaaaa tc                                                22

<210> SEQ ID NO 23
<211> LENGTH: 22
<212> TYPE: DNA
<213> ORGANISM: Artificial Sequence
<220> FEATURE:
<223> OTHER INFORMATION: synthetic DNA

<400> SEQUENCE: 23
gtggccacat ggaagtaaaa tc                                                22

<210> SEQ ID NO 24
<211> LENGTH: 22
<212> TYPE: DNA
<213> ORGANISM: Artificial Sequence
<220> FEATURE:
<223> OTHER INFORMATION: synthetic DNA

<400> SEQUENCE: 24
gtggccagat gcaagtaaaa tc                                                22
```